US010801047B2

(12) United States Patent
Lee et al.

(10) Patent No.: US 10,801,047 B2
(45) Date of Patent: Oct. 13, 2020

(54) PUTRESCINE-PRODUCING MICROORGANISM AND METHOD OF PRODUCING PUTRESCINE USING THE SAME

(71) Applicant: CJ CHEILJEDANG CORPORATION, Seoul (KR)

(72) Inventors: Kyoung Min Lee, Seoul (KR); Sung Gun Lee, Seoul (KR); Seon Hye Kim, Seoul (KR); Kyungsu Na, Seoul (KR); Hong Xian Li, Seoul (KR); Hyun-jung Bae, Seoul (KR); Young Lyeol Yang, Seoul (KR); Hye Won Um, Seoul (KR); Hyo Hyoung Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/632,084

(22) PCT Filed: Jul. 19, 2018

(86) PCT No.: PCT/KR2018/008165
§ 371 (c)(1),
(2) Date: Jan. 17, 2020

(87) PCT Pub. No.: WO2019/017706
PCT Pub. Date: Jan. 24, 2019

(65) Prior Publication Data

US 2020/0224227 A1 Jul. 16, 2020

(30) Foreign Application Priority Data

Jul. 19, 2017 (KR) ........................ 10-2017-0091628

(51) Int. Cl.
*C12P 13/00* (2006.01)

(52) U.S. Cl.
CPC .................................. *C12P 13/001* (2013.01)

(58) Field of Classification Search
CPC ...................................................... C12P 13/00
USPC .......................................................... 435/128
See application file for complete search history.

(56) References Cited

U.S. PATENT DOCUMENTS

2011/0039313 A1* 2/2011 Verseck ................ C12P 13/001 435/128
2016/0222420 A1 8/2016 Botes et al.

FOREIGN PATENT DOCUMENTS

| | | | |
|---|---|---|---|
| KR | 10-1182033 | B1 | 9/2012 |
| KR | 10-1188432 | B1 | 9/2012 |
| KR | 10-2014-0115244 | A | 9/2014 |
| KR | 10-1493585 | B1 | 2/2015 |
| KR | 10-2015-0124398 | A | 11/2015 |
| KR | 10-1735935 | B1 | 5/2017 |
| WO | 2006/005603 | A1 | 1/2006 |
| WO | 2006/065095 | A1 | 6/2006 |
| WO | 2009/125924 | A2 | 10/2009 |
| WO | 2009/125992 | A2 | 10/2009 |

OTHER PUBLICATIONS

Morris et al., "Multiple Pathways of Putrescine Biosynthesis in *Escherichia coli," The Journal of Biological Chemistry* 241(13):3129-3135, 1966.
Qian et al., "Metabolic Engineering of *Escherichia coli* for the Production of Putrescine: A Four Carbon Diamine," *Biotechnology and Bioengineering* 104(4):651-662, 2009.
Schneider et al., "Putrescine production by engineered *Corynebacterium glutamicum," Appl Microbiol Biotechnol* 88:859-868, 2010.
Schneider et al., "Biotechnological production of polyamines by Bacteria: recent achievements and future perspectives," *Appl Microbiol Biotechnol* 91:17-30, 2011.
Shin et al., "Metabolic engineering of microorganisms for the production of L-arginine and its derivatives," *Microbial Cell Factories* 13(166), 2014. (13 pages).
Smith et al., " Comparison of Biosequences," *Advances in Applied Mathematics* 2:482-489,1981.

* cited by examiner

*Primary Examiner* — Tekchand Saidha
(74) *Attorney, Agent, or Firm* — Seed IP Law Group LLP

(57) ABSTRACT

The present disclosure relates to a putrescine-producing microorganism of the genus *Corynebacterium*, and a method of producing putrescine using the same.

12 Claims, No Drawings

Specification includes a Sequence Listing.

```
                         SEQUENCE LISTING

<160> NUMBER OF SEQ ID NOS: 88

<210> SEQ ID NO 1
<211> LENGTH: 476
<212> TYPE: PRT
<213> ORGANISM: Unknown
<220> FEATURE:
<223> OTHER INFORMATION: Lactobacillus delbrueckii subsp. Bulgaricus

<400> SEQUENCE: 1

Leu Thr Glu His Tyr Leu Asn Tyr Val Asn Gly Glu Trp Arg Asp Ser
1               5                   10                  15

Ala Asp Ala Ile Glu Ile Phe Glu Pro Ala Thr Gly Lys Ser Leu Gly
            20                  25                  30

Thr Val Pro Ala Met Ser His Glu Asp Val Asp Tyr Val Met Asn Ser
        35                  40                  45

Ala Lys Lys Ala Leu Pro Ala Trp Arg Ala Leu Ser Tyr Val Glu Arg
    50                  55                  60

Ala Ala Tyr Leu Gln Lys Ala Ala Asp Ile Leu Tyr Arg Asp Ala Glu
65                  70                  75                  80

Lys Ile Gly Ser Thr Leu Ser Lys Glu Ile Ala Lys Gly Leu Lys Ser
                85                  90                  95

Ser Ile Gly Glu Val Thr Arg Thr Ala Glu Ile Val Glu Tyr Thr Ala
            100                 105                 110

Lys Val Gly Val Thr Leu Asp Gly Glu Val Met Glu Gly Gly Asn Phe
        115                 120                 125

Glu Ala Ala Ser Lys Asn Lys Leu Ala Val Val Arg Arg Glu Pro Val
    130                 135                 140

Gly Leu Val Leu Ala Ile Ser Pro Phe Asn Tyr Pro Val Asn Leu Ala
145                 150                 155                 160

Gly Ser Lys Ile Ala Pro Ala Leu Met Gly Gly Asn Val Val Ala Phe
                165                 170                 175

Lys Pro Pro Thr Gln Gly Ser Ile Ser Gly Leu Leu Leu Ala Lys Ala
            180                 185                 190

Phe Ala Glu Ala Gly Leu Pro Ala Gly Val Phe Asn Thr Ile Thr Gly
        195                 200                 205

Arg Gly Arg Val Ile Gly Asp Tyr Ile Val Glu His Pro Ala Val Asn
    210                 215                 220

Phe Ile Asn Phe Thr Gly Ser Ser Ala Val Gly Lys Asn Ile Gly Lys
225                 230                 235                 240

Leu Ala Gly Met Arg Pro Ile Met Leu Glu Leu Gly Gly Lys Asp Ala
```

```
                245                 250                 255

Ala Ile Val Leu Glu Asp Ala Asp Leu Asp Leu Thr Ala Lys Asn Ile
            260                 265                 270

Val Ala Gly Ala Phe Gly Tyr Ser Gly Gln Arg Cys Thr Ala Val Lys
        275                 280                 285

Arg Val Leu Val Met Asp Ser Val Ala Asp Glu Leu Val Glu Lys Val
    290                 295                 300

Thr Ala Leu Ala Lys Asp Leu Thr Val Gly Ile Pro Glu Glu Asp Ala
305                 310                 315                 320

Asp Ile Thr Pro Leu Ile Asp Thr Lys Ser Ala Asp Tyr Val Gln Gly
                325                 330                 335

Leu Ile Glu Glu Ala Ala Glu Lys Gly Ala Lys Pro Leu Phe Asp Phe
            340                 345                 350

Lys Arg Glu Gly Asn Leu Ile Tyr Pro Met Val Met Asp Gln Val Thr
        355                 360                 365

Thr Asp Met Arg Leu Ala Trp Glu Glu Pro Phe Gly Pro Val Leu Pro
    370                 375                 380

Phe Ile Arg Val Lys Ser Ala Asp Glu Ala Val Met Ile Ala Asn Glu
385                 390                 395                 400

Ser Glu Tyr Gly Leu Gln Ser Ser Val Phe Ser Arg Asn Phe Glu Lys
                405                 410                 415

Ala Phe Ala Ile Ala Gly Lys Leu Glu Val Gly Thr Val His Ile Asn
            420                 425                 430

Asn Lys Thr Gln Arg Gly Pro Asp Asn Phe Pro Phe Leu Gly Val Lys
        435                 440                 445

Ser Ser Gly Ala Gly Val Gln Gly Val Lys Tyr Ser Ile Gln Ala Met
    450                 455                 460

Thr Arg Val Lys Ser Val Val Phe Asn Ile Glu Asp
465                 470                 475
```

<210> SEQ ID NO 2
<211> LENGTH: 1371
<212> TYPE: DNA
<213> ORGANISM: unknown
<220> FEATURE:
<223> OTHER INFORMATION: Lactobacillus delbrueckii subsp. Bulgaricus ATCC 11842

<400> SEQUENCE: 2

```
ttgacagaac actatttaaa ctatgtcaat ggcgaatggc gggactccgc tgacgcgatt      60

gaaattttcg aaccagcaac tggcaagtcc ctgggtactg tacctgccat gtcccacgaa     120

gacgtggact acgtaatgaa cagcgccaaa aaggcccttc cagcctggcg ggccctctca     180

tacgttgaac gggccgcata cttgcaaaag gcagcggaca tcctttaccg agatgctgaa     240

aagatcggtt ctaccttgtc caaggaaatc gccaagggcc tcaagtcctc tatcggcgaa     300

gtaacccgga cggcggaaat cgttgaatac acggccaagg tcggcgtaac tttggacggg     360

gaagtcatgg agggcggcaa ctttgaagcg gcaagcaaga acaagttggc tgttgtccgc     420

cgggaaccag tcggcctggt tttggcaatt tcacccttca actacccggt taacctggcc     480

ggctcaaaga tcgcgcctgc tttgatgggc gggaacgtgg tggccttcaa gccgccgaca     540

caagggtcaa tctccggtct gcttttggcc aaggccttcg ccgaagctgg cctgccagcc     600

ggcgtcttca acaccattac cggccggggt cgggttatcg gcgactacat cgttgaacac     660

ccggcagtca acttcatcaa cttcaccggt tccagtgctg tcggcaagaa catcggcaaa     720
```

```
ctggccggga tgcggccgat tatgctggaa cttggcggca aggacgcggc catcgtcttg    780

gaagacgctg acttggacct gacggccaag aacatcgttg ccggcgcctt tggctactcc    840

ggccagcgtt gtaccgccgt taagcgggtt ctggtcatgg acagcgtggc tgacgaattg    900

gttgaaaagg tgactgcttt ggccaaggat ttgacggtcg ggataccaga agaggatgcc    960

gacatcactc ctttgatcga cactaagtct gccgactacg tacaaggctt aattgaagaa   1020

gccgcagaaa agggcgctaa gcctttgttt gacttcaagc gcgaaggcaa cctgatctac   1080

ccaatggtca tggaccaagt gacgactgac atgcgcctgg cctgggaaga accatttggg   1140

ccagtattgc cattcatccg cgtcaagtca gctgacgaag ctgtcatgat tgccaatgaa   1200

tcagaatacg gccttcaaag ctccgtcttc tcacggaact ttgaaaaagc ctttgccatt   1260

gcaggaaaat tggaagtggg cacggtccac atcaacaaca agacccaaag aggtccggac   1320

aacttcccat tcctgggcgt aaagagctca ggggcaggcg tacagggggt c            1371


<210> SEQ ID NO 3
<211> LENGTH: 48
<212> TYPE: DNA
<213> ORGANISM: Artificial Sequence
<220> FEATURE:
<223> OTHER INFORMATION: primer gapN(L)-F

<400> SEQUENCE: 3

aaggaaacac tgatatcatg acagaacact atttaaacta tgtcaatg                  48


<210> SEQ ID NO 4
<211> LENGTH: 42
<212> TYPE: DNA
<213> ORGANISM: Artificial Sequence
<220> FEATURE:
<223> OTHER INFORMATION: primer gapN(L)-R

<400> SEQUENCE: 4

gccaaaacag cctcgagtta gtcttcgatg ttgaagacaa cg                        42


<210> SEQ ID NO 5
<211> LENGTH: 36
<212> TYPE: DNA
<213> ORGANISM: Artificial Sequence
<220> FEATURE:
<223> OTHER INFORMATION: primer CJ7-F

<400> SEQUENCE: 5

ggcccactag tctcgaggcc ggcatagcct accgat                               36


<210> SEQ ID NO 6
<211> LENGTH: 24
<212> TYPE: DNA
<213> ORGANISM: Artificial Sequence
<220> FEATURE:
<223> OTHER INFORMATION: primer CJ7-R

<400> SEQUENCE: 6

gatatcagtg tttcctttcg ttgg                                            24


<210> SEQ ID NO 7
<211> LENGTH: 475
<212> TYPE: PRT
<213> ORGANISM: Unknown
<220> FEATURE:
<223> OTHER INFORMATION: Streptococcus mutans ATCC 25175

<400> SEQUENCE: 7
```

```
Leu Thr Lys Gln Tyr Lys Asn Tyr Val Asn Gly Glu Trp Lys Leu Ser
1               5                   10                  15

Glu Asn Glu Ile Lys Ile Tyr Glu Pro Ala Ser Gly Ala Glu Leu Gly
            20                  25                  30

Ser Val Pro Ala Met Ser Thr Glu Glu Val Asp Tyr Val Tyr Ala Ser
        35                  40                  45

Ala Lys Lys Ala Gln Pro Ala Trp Arg Ser Leu Ser Tyr Ile Glu Arg
    50                  55                  60

Ala Ala Tyr Leu His Lys Val Ala Asp Ile Leu Met Arg Asp Lys Glu
65                  70                  75                  80

Lys Ile Gly Ala Val Leu Ser Lys Glu Val Ala Lys Gly Tyr Lys Ser
                85                  90                  95

Ala Val Ser Glu Val Val Arg Thr Ala Glu Ile Ile Asn Tyr Ala Ala
            100                 105                 110

Glu Glu Gly Leu Arg Met Glu Gly Glu Val Leu Glu Gly Gly Ser Phe
        115                 120                 125

Glu Ala Ala Ser Lys Lys Lys Ile Ala Val Val Arg Arg Glu Pro Val
    130                 135                 140

Gly Leu Val Leu Ala Ile Ser Pro Phe Asn Tyr Pro Val Asn Leu Ala
145                 150                 155                 160

Gly Ser Lys Ile Ala Pro Ala Leu Ile Ala Gly Asn Val Ile Ala Phe
                165                 170                 175

Lys Pro Pro Thr Gln Gly Ser Ile Ser Gly Leu Leu Leu Ala Glu Ala
            180                 185                 190

Phe Ala Glu Ala Gly Leu Pro Ala Gly Val Phe Asn Thr Ile Thr Gly
        195                 200                 205

Arg Gly Ser Glu Ile Gly Asp Tyr Ile Val Glu His Gln Ala Val Asn
    210                 215                 220

Phe Ile Asn Phe Thr Gly Ser Thr Gly Ile Gly Glu Arg Ile Gly Lys
225                 230                 235                 240

Met Ala Gly Met Arg Pro Ile Met Leu Glu Leu Gly Gly Lys Asp Ser
                245                 250                 255

Ala Ile Val Leu Glu Asp Ala Asp Leu Glu Leu Thr Ala Lys Asn Ile
            260                 265                 270

Ile Ala Gly Ala Phe Gly Tyr Ser Gly Gln Arg Cys Thr Ala Val Lys
        275                 280                 285

Arg Val Leu Val Met Glu Ser Val Ala Asp Glu Leu Val Glu Lys Ile
    290                 295                 300

Arg Glu Lys Val Leu Ala Leu Thr Ile Gly Asn Pro Glu Asp Asp Ala
305                 310                 315                 320

Asp Ile Thr Pro Leu Ile Asp Thr Lys Ser Ala Asp Tyr Val Glu Gly
                325                 330                 335

Leu Ile Asn Asp Ala Asn Asp Lys Gly Ala Ala Ala Leu Thr Glu Ile
            340                 345                 350

Lys Arg Glu Gly Asn Leu Ile Cys Pro Ile Leu Phe Asp Lys Val Thr
        355                 360                 365

Thr Asp Met Arg Leu Ala Trp Glu Glu Pro Phe Gly Pro Val Leu Pro
    370                 375                 380

Ile Ile Arg Val Thr Ser Val Glu Glu Ala Ile Glu Ile Ser Asn Lys
385                 390                 395                 400

Ser Glu Tyr Gly Leu Gln Ala Ser Ile Phe Thr Asn Asp Phe Pro Arg
                405                 410                 415
```

```
Ala Phe Gly Ile Ala Glu Gln Leu Glu Val Gly Thr Val His Ile Asn
            420                 425                 430

Asn Lys Thr Gln Arg Gly Thr Asp Asn Phe Pro Phe Leu Gly Ala Lys
        435                 440                 445

Lys Ser Gly Ala Gly Ile Gln Gly Val Lys Tyr Ser Ile Glu Ala Met
    450                 455                 460

Thr Thr Val Lys Ser Val Val Phe Asp Ile Lys
465                 470                 475
```

<210> SEQ ID NO 8
<211> LENGTH: 1428
<212> TYPE: DNA
<213> ORGANISM: Unknown
<220> FEATURE:
<223> OTHER INFORMATION: Streptococcus mutans ATCC 25175

<400> SEQUENCE: 8

```
ttgacaaaac aatataaaaa ttatgtcaat ggcgagtgga agctttcaga aaatgaaatt     60

aaaatctacg aaccggccag tggagctgaa ttgggttcag ttccagcaat gagtactgaa    120

gaagtagatt atgtttatgc ttcagccaag aaagctcaac cagcttggcg atcactttca    180

tacatagaac gtgctgccta ccttcataag gtagcagata ttttgatgcg tgataaagaa    240

aaaataggtg ctgttctttc caaagaggtt gctaaaggtt ataaatcagc agtcagcgaa    300

gttgttcgta ctgcagaaat cattaattat gcagctgaag aaggccttcg tatggaaggt    360

gaagtccttg aaggcggcag ttttgaagca gccagcaaga aaaaaattgc cgttgttcgt    420

cgtgaaccag taggtcttgt attagctatt tcaccattta actaccctgt taacttggca    480

ggttcgaaaa ttgcaccggc tcttattgcg ggaaatgtta ttgcttttaa accaccgacg    540

caaggatcaa tctcagggct cttacttgct gaagcatttg ctgaagctgg acttcctgca    600

ggtgtcttta ataccattac aggtcgtggt tctgaaattg gagactatat tgtagaacat    660

caagccgtta actttatcaa tttcactggt tcaacaggaa ttggggaacg tattggcaaa    720

atggctggta tgcgtccgat tatgcttgaa ctcggtggaa aagattcagc catcgttctt    780

gaagatgcag accttgaatt gactgctaaa aatattattg caggtgcttt tggttattca    840

ggtcaacgct gtacagcagt taaacgtgtt cttgtgatgg aaagtgttgc tgatgaactg    900

gtcgaaaaaa tccgtgaaaa agttcttgca ttaacaattg gtaatccaga agacgatgca    960

gatattacac cgttgattga tacaaaatca gctgattatg tagaaggtct tattaatgat   1020

gccaatgata aaggagccgc tgcccttact gaaatcaaac gtgaaggtaa tcttatctgt   1080

ccaatcctct ttgataaggt aacgacagat atgcgtcttg cttgggaaga accatttggt   1140

cctgttcttc cgatcattcg tgtgacatct gtagaagaag ccattgaaat ttctaacaaa   1200

tcggaatatg gacttcaggc ttctatcttt acaaatgatt tcccacgcgc ttttggtatt   1260

gctgagcagc ttgaagttgg tacagttcat atcaataata agacacagcg cggtacggac   1320

aacttcccat tcttaggggc taaaaaatca ggtgcaggta ttcaaggggt aaaatattct   1380

attgaagcta tgacaactgt taaatccgtc gtatttgata tcaaataa                1428
```

<210> SEQ ID NO 9
<211> LENGTH: 45
<212> TYPE: DNA
<213> ORGANISM: Artificial Sequence
<220> FEATURE:
<223> OTHER INFORMATION: Primer gapN(S)-R

<400> SEQUENCE: 9
gccaaaacag cctcgagtta tttgatatca aatacgacgg attta 45

<210> SEQ ID NO 10
<211> LENGTH: 80
<212> TYPE: PRT
<213> ORGANISM: Corynebacterium glutamicum

<400> SEQUENCE: 10

```
Leu Thr Thr Leu Thr Leu Ser Pro Glu Leu Gln Ala Leu Thr Val Arg
1               5                   10                  15

Asn Tyr Pro Ser Asp Trp Ser Asp Val Asp Thr Lys Ala Val Asp Thr
            20                  25                  30

Val Arg Val Leu Ala Ala Asp Ala Val Glu Asn Cys Gly Ser Gly His
        35                  40                  45

Pro Gly Thr Ala Met Ser Leu Ala Pro Leu Ala Tyr Thr Leu Tyr Gln
    50                  55                  60

Arg Val Met Asn Val Asp Pro Gln Asp Thr Asn Trp Ala Gly Arg Asp
65                  70                  75                  80
```

<210> SEQ ID NO 11
<211> LENGTH: 2103
<212> TYPE: DNA
<213> ORGANISM: Corynebacterium glutamicum

<400> SEQUENCE: 11

```
ttgaccacct tgacgctgtc acctgaactt caggcgctca ctgtacgcaa ttacccctct     60
gattggtccg atgtggacac caaggctgta gacactgttc gtgtcctcgc tgcagacgct    120
gtagaaaact gtggctccgg ccacccaggc accgcaatga gcctggctcc ccttgcatac    180
accttgtacc agcgggttat gaacgtagat ccacaggaca ccaactgggc aggccgtgac    240
cgcttcgttc tttcttgtgg ccactcctct ttgacccagt acatccagct ttacttgggt    300
ggattcggcc ttgagatgga tgacctgaag gctctgcgca cctgggattc cttgacccca    360
ggacaccctg agtaccgcca caccaagggc gttgagatca ccactggccc tcttggccag    420
ggtcttgcat ctgcagttgg tatggccatg gctgctcgtc gtgagcgtgg cctattcgac    480
ccaaccgctg ctgagggcga atccccattc gaccaccaca tctacgtcat tgcttctgat    540
ggtgacctgc aggaaggtgt cacctctgag gcatcctcca tcgctggcac ccagcagctg    600
ggcaacctca tcgtgttctg ggatgacaac cgcatctcca tcgaagacaa cactgagatc    660
gctttcaacg aggacgttgt tgctcgttac aaggcttacg gctggcagac cattgaggtt    720
gaggctggcg aggacgttgc agcaatcgaa gctgcagtgg ctgaggctaa gaaggacacc    780
aagcgaccta ccttcatccg cgttcgcacc atcatcggct tcccagctcc aactatgatg    840
aacaccggtg ctgtgcacgg tgctgctctt ggcgcagctg aggttgcagc aaccaagact    900
gagcttggat tcgatcctga ggctcacttc gcgatcgacg atgaggttat cgctcacacc    960
cgctccctcg cagagcgcgc tgcacagaag aaggctgcat ggcaggtcaa gttcgatgag   1020
tgggcagctg ccaaccctga gaacaaggct ctgttcgatc gcctgaactc ccgtgagctt   1080
ccagcgggct acgctgacga gctcccaaca tgggatgcag atgagaaggg cgtcgcaact   1140
cgtaaggctt ccgaggctgc acttcaggca ctgggcaaga cccttcctga gctgtggggc   1200
ggttccgctg acctcgcagg ttccaacaac accgtgatca agggctcccc ttccttcggc   1260
cctgagtcca tctccaccga gacctggtct gctgagcctt acggccgtaa cctgcacttc   1320
ggtatccgtg agcacgctat gggatccatc ctcaacggca tttccctcca cggtggcacc   1380
```

```
cgcccatacg gcggaacctt cctcatcttc tccgactaca tgcgtcctgc agttcgtctt   1440

gcagctctca tggagaccga cgcttactac gtctggaccc acgactccat cggtctgggc   1500

gaagatggcc caacccacca gcctgttgaa accttggctg cactgcgcgc catcccaggt   1560

ctgtccgtcc tgcgtcctgc agatgcgaac gagaccgccc aggcttgggc tgcagcactt   1620

gagtacaagg aaggccctaa gggtcttgca ctgacccgcc agaacgttcc tgttctggaa   1680

ggcaccaagg agaaggctgc tgaaggcgtt cgccgcggtg gctacgtcct ggttgagggt   1740

tccaaggaaa ccccagatgt gatcctcatg ggctccggct ccgaggttca gcttgcagtt   1800

aacgctgcga aggctctgga agctgagggc gttgcagctc gcgttgtttc cgttccttgc   1860

atggattggt tccaggagca ggacgcagag tacatcgagt ccgttctgcc tgcagctgtg   1920

accgctcgtg tgtctgttga agctggcatc gcaatgcctt ggtaccgctt cttgggcacc   1980

cagggccgtg ctgtctccct tgagcacttc ggtgcttctg cggattacca gaccctgttt   2040

gagaagttcg gcatcaccac cgatgcagtc gtggcagcgg ccaaggactc cattaacggt   2100

taa                                                                 2103
```

<210> SEQ ID NO 12
<211> LENGTH: 37
<212> TYPE: DNA
<213> ORGANISM: Artificial Sequence
<220> FEATURE:
<223> OTHER INFORMATION: Primer NCgl1512_5F

<400> SEQUENCE: 12

```
ccggggatcc tctagagtag acgcttgatt ggcggac                             37
```

<210> SEQ ID NO 13
<211> LENGTH: 21
<212> TYPE: DNA
<213> ORGANISM: Artificial Sequence
<220> FEATURE:
<223> OTHER INFORMATION: Primer NCgl1512_5R

<400> SEQUENCE: 13

```
tccttcctgg gttaaaccgg g                                              21
```

<210> SEQ ID NO 14
<211> LENGTH: 39
<212> TYPE: DNA
<213> ORGANISM: Artificial Sequence
<220> FEATURE:
<223> OTHER INFORMATION: Primer NCgl1512_ATG_3F

<400> SEQUENCE: 14

```
gtttaaccca ggaaggaatg accaccttga cgctgtcac                           39
```

<210> SEQ ID NO 15
<211> LENGTH: 36
<212> TYPE: DNA
<213> ORGANISM: Artificial Sequence
<220> FEATURE:
<223> OTHER INFORMATION: Primer NCgl1512_3R

<400> SEQUENCE: 15

```
gcaggtcgac tctagagtcg aataggccac gctcac                              36
```

<210> SEQ ID NO 16
<211> LENGTH: 700
<212> TYPE: PRT

```
<213> ORGANISM: Corynebacterium glutamicum

<400> SEQUENCE: 16

Leu Thr Thr Leu Thr Leu Ser Pro Glu Leu Gln Ala Leu Thr Val Arg
1               5                   10                  15

Asn Tyr Pro Ser Asp Trp Ser Asp Val Asp Thr Lys Ala Val Asp Thr
            20                  25                  30

Val Arg Val Leu Ala Ala Asp Ala Val Glu Asn Cys Gly Ser Gly His
        35                  40                  45

Pro Gly Thr Ala Met Ser Leu Ala Pro Leu Ala Tyr Thr Leu Tyr Gln
    50                  55                  60

Arg Val Met Asn Val Asp Pro Gln Asp Thr Asp Trp Ala Gly Arg Asp
65                  70                  75                  80

Arg Phe Val Leu Ser Cys Gly His Ser Ser Leu Thr Gln Tyr Ile Gln
                85                  90                  95

Leu Tyr Leu Gly Gly Phe Gly Leu Glu Met Asp Asp Leu Lys Ala Leu
            100                 105                 110

Arg Thr Trp Asp Ser Leu Thr Pro Gly His Pro Glu Tyr Arg His Thr
        115                 120                 125

Lys Gly Val Glu Ile Thr Thr Gly Pro Leu Gly Gln Gly Leu Ala Ser
    130                 135                 140

Ala Val Gly Met Ala Met Ala Ala Arg Arg Glu Arg Gly Leu Phe Asp
145                 150                 155                 160

Pro Thr Ala Ala Glu Gly Glu Ser Pro Phe Asp His His Ile Tyr Val
                165                 170                 175

Ile Ala Ser Asp Gly Asp Leu Gln Glu Gly Val Thr Ser Glu Ala Ser
            180                 185                 190

Ser Ile Ala Gly Thr Gln Gln Leu Gly Asn Leu Ile Val Phe Trp Asp
        195                 200                 205

Asp Asn Arg Ile Ser Ile Glu Asp Asn Thr Glu Ile Ala Phe Asn Glu
    210                 215                 220

Asp Val Val Ala Arg Tyr Lys Ala Tyr Gly Trp Gln Thr Ile Glu Val
225                 230                 235                 240

Glu Ala Gly Glu Asp Val Ala Ala Ile Glu Ala Ala Val Ala Glu Ala
                245                 250                 255

Lys Lys Asp Thr Lys Arg Pro Thr Phe Ile Arg Val Arg Thr Ile Ile
            260                 265                 270

Gly Phe Pro Ala Pro Thr Met Met Asn Thr Gly Ala Val His Gly Ala
        275                 280                 285

Ala Leu Gly Ala Ala Glu Val Ala Ala Thr Lys Thr Glu Leu Gly Phe
    290                 295                 300

Asp Pro Glu Ala His Phe Ala Ile Asp Asp Glu Val Ile Ala His Thr
305                 310                 315                 320

Arg Ser Leu Ala Glu Arg Ala Ala Gln Lys Lys Ala Ala Trp Gln Val
                325                 330                 335

Lys Phe Asp Glu Trp Ala Ala Ala Asn Pro Glu Asn Lys Ala Leu Phe
            340                 345                 350

Asp Arg Leu Asn Ser Arg Glu Leu Pro Ala Gly Tyr Ala Asp Glu Leu
        355                 360                 365

Pro Thr Trp Asp Ala Asp Glu Lys Gly Val Ala Thr Arg Lys Ala Ser
    370                 375                 380

Glu Ala Ala Leu Gln Ala Leu Gly Lys Thr Leu Pro Glu Leu Trp Gly
385                 390                 395                 400
```

```
Gly Ser Ala Asp Leu Ala Gly Ser Asn Asn Thr Val Ile Lys Gly Ser
                405                 410                 415

Pro Ser Phe Gly Pro Glu Ser Ile Ser Thr Glu Thr Trp Ser Ala Glu
            420                 425                 430

Pro Tyr Gly Arg Asn Leu His Phe Gly Ile Arg Glu His Ala Met Gly
        435                 440                 445

Ser Ile Leu Asn Gly Ile Ser Leu His Gly Gly Thr Arg Pro Tyr Gly
    450                 455                 460

Gly Thr Phe Leu Ile Phe Ser Asp Tyr Met Arg Pro Ala Val Arg Leu
465                 470                 475                 480

Ala Ala Leu Met Glu Thr Asp Ala Tyr Tyr Val Trp Thr His Asp Ser
                485                 490                 495

Ile Gly Leu Gly Glu Asp Gly Pro Thr His Gln Pro Val Glu Thr Leu
            500                 505                 510

Ala Ala Leu Arg Ala Ile Pro Gly Leu Ser Val Leu Arg Pro Ala Asp
        515                 520                 525

Ala Asn Glu Thr Ala Gln Ala Trp Ala Ala Ala Leu Glu Tyr Lys Glu
    530                 535                 540

Gly Pro Lys Gly Leu Ala Leu Thr Arg Gln Asn Ile Pro Val Leu Glu
545                 550                 555                 560

Gly Thr Lys Glu Lys Ala Ala Glu Gly Val Arg Arg Gly Gly Tyr Val
                565                 570                 575

Leu Val Glu Gly Ser Lys Glu Thr Pro Asp Val Ile Leu Met Gly Ser
            580                 585                 590

Gly Ser Glu Val Gln Leu Ala Val Asn Ala Ala Lys Ala Leu Glu Ala
        595                 600                 605

Glu Gly Val Ala Ala Arg Val Val Ser Val Pro Cys Met Asp Trp Phe
    610                 615                 620

Gln Glu Gln Asp Ala Glu Tyr Ile Glu Ser Val Leu Pro Ala Ala Val
625                 630                 635                 640

Thr Ala Arg Val Ser Val Glu Ala Gly Ile Ala Met Pro Trp Tyr Arg
                645                 650                 655

Phe Leu Gly Thr Gln Gly Arg Ala Val Ser Leu Glu His Phe Gly Ala
            660                 665                 670

Ser Ala Asp Tyr Gln Thr Leu Phe Glu Lys Phe Gly Ile Thr Thr Asp
        675                 680                 685

Ala Val Val Ala Ala Ala Lys Asp Ser Ile Asn Gly
    690                 695                 700


<210> SEQ ID NO 17
<211> LENGTH: 2103
<212> TYPE: DNA
<213> ORGANISM: Corynebacterium glutamicum

<400> SEQUENCE: 17

ttgaccacct tgacgctgtc acctgaactt caggcgctca ctgtacgcaa ttacccctct      60

gattggtccg atgtggacac caaggctgta gacactgttc gtgtcctcgc tgcagacgct     120

gtagaaaact gtggctccgg ccacccaggc accgcaatga gcctggctcc ccttgcatac     180

accttgtacc agcgggttat gaacgtagat ccacaggaca ccgactgggc aggccgtgac     240

cgcttcgttc tttcttgtgg ccactcctct ttgacccagt acatccagct ttacttgggt     300

ggattcggcc ttgagatgga tgacctgaag gctctgcgca cctgggattc cttgacccca     360

ggacaccctg agtaccgcca caccaagggc gtagagatca ccactggccc tcttggccag     420
```

```
ggtcttgcat ctgcagttgg tatggccatg gctgctcgtc gtgagcgtgg cctattcgac    480

ccaaccgctg ctgagggcga atccccattc gaccaccaca tctacgtcat tgcttctgat    540

ggtgacctgc aggaaggtgt cacctctgag gcatcctcca tcgctggcac ccagcagctg    600

ggcaacctca tcgtgttctg ggatgacaac cgcatctcca tcgaagacaa cactgagatc    660

gctttcaacg aggacgttgt tgctcgttac aaggcttacg gctggcagac cattgaggtt    720

gaggctggcg aggacgttgc agcaatcgaa gctgcagtgg ctgaggctaa gaaggacacc    780

aagcgaccta ccttcatccg cgttcgcacc atcatcggct tcccagctcc aaccatgatg    840

aacaccggtg ctgtgcacgg tgctgctctt ggcgcagctg aggttgcagc aaccaagact    900

gagcttggat tcgatcctga ggctcacttc gcgatcgacg atgaggttat cgctcacacc    960

cgctccctcg cagagcgcgc tgcacagaag aaggctgcat ggcaggtcaa gttcgatgag   1020

tgggcagctg ccaaccctga gaacaaggct ctgttcgatc gcctgaactc ccgtgagctt   1080

ccagcgggct acgctgacga gctcccaaca tgggatgcag atgagaaggg cgtcgcaact   1140

cgtaaggctt ccgaggctgc acttcaggca ctgggcaaga cccttcctga gctgtggggc   1200

ggttccgctg acctcgcagg ttccaacaac accgtgatca agggctcccc ttccttcggc   1260

cctgagtcca tctccaccga gacctggtct gctgagcctt acggccgtaa cctgcacttc   1320

ggtatccgtg agcacgctat gggatccatc ctcaacggca tttccctcca cggtggcacc   1380

cgcccatacg gcggaacctt cctcatcttc tccgactaca tgcgtcctgc agttcgtctt   1440

gcagctctca tggagaccga cgcttactac gtctggaccc acgactccat cggtctgggc   1500

gaagatggcc caacccacca gcctgttgaa accttggctg cactgcgcgc catcccaggt   1560

ctgtccgtcc tgcgtcctgc agatgcgaac gagaccgccc aggcttgggc tgcagcactt   1620

gagtacaagg aaggccctaa gggtcttgca ctaacccgcc agaacattcc tgttctggaa   1680

ggcaccaagg agaaggctgc tgaaggcgtt cgccgcggtg gctacgtcct ggttgagggt   1740

tccaaggaaa ccccagatgt gatcctcatg ggctccggct ccgaggttca gcttgcagtt   1800

aacgctgcga aggctctgga agctgagggc gttgcagctc gcgttgtttc cgttccttgc   1860

atggattggt tccaggagca ggacgcagag tacatcgagt ccgttctgcc tgcagctgtg   1920

accgctcgtg tgtctgttga agctggcatc gcaatgcctt ggtaccgctt cttgggcacc   1980

cagggccgtg ctgtctccct tgagcacttc ggtgcttctg cggattacca gaccctgttt   2040

gagaagttcg gcatcaccac cgatgcagtc gtggcagcgg ccaaggactc cattaacggt   2100

taa                                                                 2103
```

```
<210> SEQ ID NO 18
<211> LENGTH: 36
<212> TYPE: DNA
<213> ORGANISM: Artificial Sequence
<220> FEATURE:
<223> OTHER INFORMATION: Primer NCgl1512-PC7-F

<400> SEQUENCE: 18

gtttaaccca ggaaggagcc ggcatagcct accgat                               36


<210> SEQ ID NO 19
<211> LENGTH: 39
<212> TYPE: DNA
<213> ORGANISM: Artificial Sequence
<220> FEATURE:
<223> OTHER INFORMATION: Primer NCgl1512-PC7-ATG-F

<400> SEQUENCE: 19
```

```
aaggaaacac tgatatcatg accaccttga cgctgtcac                         39


<210> SEQ ID NO 20
<211> LENGTH: 514
<212> TYPE: PRT
<213> ORGANISM: Corynebacterium glutamicum

<400> SEQUENCE: 20

Val Ser Thr Asn Thr Thr Pro Ser Ser Trp Thr Asn Pro Leu Arg Asp
1               5                   10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
    290                 295                 300

Pro Leu Asp Lys Thr Ser Ala Arg Gly Gln Tyr Ala Ala Gly Trp Gln
305                 310                 315                 320

Gly Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365
```

```
Gly Arg Arg Val Thr Glu Ile Ala Val Val Phe Lys Asp Ala Pro His
    370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415

Lys Val Pro Gly Ser Ala Met Glu Val Arg Asp Val Asn Met Asp Phe
            420                 425                 430

Ser Tyr Ser Glu Ser Phe Thr Glu Glu Ser Pro Glu Ala Tyr Glu Arg
        435                 440                 445

Leu Ile Leu Asp Ala Leu Leu Asp Glu Ser Ser Leu Phe Pro Thr Asn
    450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
                485                 490                 495

Pro Lys Ser Ala Asp Glu Met Leu Ser Arg Asn Gly His Thr Trp Arg
            500                 505                 510

Arg Pro


<210> SEQ ID NO 21
<211> LENGTH: 1545
<212> TYPE: DNA
<213> ORGANISM: Corynebacterium glutamicum

<400> SEQUENCE: 21

gtgagcacaa acacgacccc ctccagctgg acaaacccac tgcgcgaccc gcaggataaa      60

cgactccccc gcatcgctgg cccttccggc atggtgatct tcggtgtcac tggcgacttg     120

gctcgaaaga agctgctccc cgccatttat gatctagcaa accgcggatt gctgccccca     180

ggattctcgt tggtaggtta cggccgccgc gaatggtcca aagaagactt tgaaaaatac     240

gtacgcgatg ccgcaagtgc tggtgctcgt acggaattcc gtgaaaatgt ttgggagcgc     300

ctcgccgagg gtatggaatt tgttcgcggc aactttgatg atgatgcagc tttcgacaac     360

ctcgctgcaa cactcaagcg catcgacaaa acccgcggca ccgccggcaa ctgggcttac     420

tacctgtcca ttccaccaga ttccttcaca gcggtctgcc accagctgga gcgttccggc     480

atggctgaat ccaccgaaga agcatggcgc cgcgtgatca tcgagaagcc tttcggccac     540

aacctcgaat ccgcacacga gctcaaccag ctggtcaacg cagtcttccc agaatcttct     600

gtgttccgca tcgaccacta tttgggcaag gaaacagttc aaaacatcct ggctctgcgt     660

tttgctaacc agctgtttga gccactgtgg aactccaact acgttgacca cgtccagatc     720

accatggctg aagatattgg cttgggtgga cgtgctggtt actacgacgg catcggcgca     780

gcccgcgacg tcatccagaa ccacctgatc cagctcttgg ctctggttgc catggaagaa     840

ccaatttctt tcgtgccagc gcagctgcag gcagaaaaga tcaaggtgct ctctgcgaca     900

aagccgtgct acccattgga taaaacctcc gctcgtggtc agtacgctgc cggttggcag     960

ggctctgagt tagtcaaggg acttcgcgaa gaagatggct tcaaccctga gtccaccact    1020

gagacttttg cggcttgtac cttagagatc acgtctcgtc gctgggctgg tgtgccgttc    1080

tacctgcgca ccggtaagcg tcttggtcgc cgtgttactg agattgccgt ggtgtttaaa    1140

gacgcaccac accagccttt cgacggcgac atgactgtat cccttggcca aaacgccatc    1200

gtgattcgcg tgcagcctga tgaaggtgtg ctcatccgct tcggttccaa ggttccaggt    1260
```

```
tctgccatgg aagtccgtga cgtcaacatg gacttctcct actcagaatc cttcactgaa   1320

gaatcacctg aagcatacga gcgcctcatt ttggatgcgc tgttagatga atccagcctc   1380

ttccctacca acgaggaagt ggaactgagc tggaagattc tggatccaat tcttgaagca   1440

tgggatgccg atggagaacc agaggattac ccagcgggta cgtggggtcc aaagagcgct   1500

gatgaaatgc tttcccgcaa cggtcacacc tggcgcaggc cataa                   1545


<210> SEQ ID NO 22
<211> LENGTH: 37
<212> TYPE: DNA
<213> ORGANISM: Artificial Sequence
<220> FEATURE:
<223> OTHER INFORMATION: Primer NCgl1514-5F

<400> SEQUENCE: 22

ccggggatcc tctagactga aggtgccaac actcagc                              37


<210> SEQ ID NO 23
<211> LENGTH: 23
<212> TYPE: DNA
<213> ORGANISM: Artificial Sequence
<220> FEATURE:
<223> OTHER INFORMATION: Primer NCgl1514-5R

<400> SEQUENCE: 23

gatggtagtg tcacgatcct ttc                                             23


<210> SEQ ID NO 24
<211> LENGTH: 37
<212> TYPE: DNA
<213> ORGANISM: Artificial Sequence
<220> FEATURE:
<223> OTHER INFORMATION: Primer PC7-F(1514)

<400> SEQUENCE: 24

gatcgtgaca ctaccatcgc cggcatagcc taccgat                              37


<210> SEQ ID NO 25
<211> LENGTH: 38
<212> TYPE: DNA
<213> ORGANISM: Artificial Sequence
<220> FEATURE:
<223> OTHER INFORMATION: Primer NCgl1514-3F(C7-GTG)

<400> SEQUENCE: 25

aaggaaacac tgatatcgtg agcacaaaca cgaccccc                             38


<210> SEQ ID NO 26
<211> LENGTH: 35
<212> TYPE: DNA
<213> ORGANISM: Artificial Sequence
<220> FEATURE:
<223> OTHER INFORMATION: Primer NCgl1514-3R

<400> SEQUENCE: 26

gcaggtcgac tctagacggt ggattcagcc atgcc                                35


<210> SEQ ID NO 27
<211> LENGTH: 514
<212> TYPE: PRT
<213> ORGANISM: Corynebacterium glutamicum

<400> SEQUENCE: 27
```

```
Val Ser Thr Asn Thr Thr Pro Thr Ser Trp Thr Asn Pro Leu Arg Asp
1               5                   10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
    290                 295                 300

Pro Leu Asp Lys Thr Ser Ala Arg Gly Gln Tyr Ala Ala Gly Trp Gln
305                 310                 315                 320

Gly Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365

Gly Arg Arg Val Thr Glu Ile Ala Val Val Phe Lys Asp Ala Pro His
    370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415

Lys Val Pro Gly Ser Ala Met Glu Val Arg Asp Val Asn Met Asp Phe
```

```
            420                 425                 430

Ser Tyr Ser Glu Ser Phe Thr Glu Glu Ser Pro Glu Ala Tyr Glu Arg
        435                 440                 445

Leu Ile Leu Asp Ala Leu Leu Asp Glu Ser Ser Leu Phe Pro Thr Asn
    450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
                485                 490                 495

Pro Lys Ser Ala Asp Glu Met Leu Ser Arg Asn Gly His Thr Trp Arg
            500                 505                 510

Arg Pro


<210> SEQ ID NO 28
<211> LENGTH: 1545
<212> TYPE: DNA
<213> ORGANISM: Corynebacterium glutamicum

<400> SEQUENCE: 28

gtgagcacaa acacgacccc caccagctgg acaaacccac tgcgcgaccc gcaggataaa      60

cgactccccc gcatcgctgg cccttccggc atggtgatct tcggtgtcac tggcgacttg     120

gctcgaaaga agctgcttcc cgccatttat gatctagcaa accgcggatt gctgccccca     180

ggattctcgt tggtaggtta cggccgccgc gaatggtcca aagaagactt tgaaaaatac     240

gtacgcgatg ccgcaagtgc tggtgctcgt acggaatttc gtgaaaatgt ttgggagcgc     300

ctcgccgagg gtatggaatt tgttcgcggc aactttgatg atgatgcagc tttcgacaac     360

ctcgctgcaa cactcaagcg catcgacaaa acccgcggca ccgccggcaa ctgggcttac     420

tacctgtcca ttccaccaga ttccttcaca gcggtctgcc accagctgga gcgttccggc     480

atggctgaat ccaccgaaga agcatggcgc cgcgtgatca tcgagaagcc tttcggccac     540

aacctcgaat ccgcacacga gctcaaccag ctggtcaacg cagtcttccc agaatcttct     600

gtgttccgca tcgaccacta tttgggcaag gaaacagttc aaaacatcct ggctctgcgt     660

tttgctaacc agctgtttga gccactgtgg aactccaact acgttgacca cgtccagatc     720

accatggctg aagatatcgg cttgggtgga cgtgctggtt actacgacgg catcggtgca     780

gcccgcgacg tcatccagaa ccacctgatc cagctcttgg ctctggttgc catggaagaa     840

ccaatttctt tcgtgccagc gcagctgcag gcagaaaaga tcaaggtgct ctctgcgaca     900

aagccatgct acccattgga taaaacctcc gctcgtggtc agtacgctgc cggttggcag     960

ggctctgagt tagtcaaggg acttcgcgaa gaagatggct tcaaccctga gtccaccact    1020

gagacttttg cggcttgtac cttagagatc acgtctcgtc gctgggctgg tgtgccgttc    1080

tacctgcgca ccggtaagcg tcttggtcgc cgtgttactg agattgccgt ggtgtttaaa    1140

gacgcaccac accagccttt cgacggcgac atgactgtat cccttggcca aaacgccatc    1200

gtgattcgcg tgcagcctga tgaaggtgtg ctcatccgct tcggttccaa ggttccaggt    1260

tctgccatgg aagtccgtga cgtcaacatg gacttctcct actcagaatc cttcactgaa    1320

gaatcacctg aagcatacga gcgcctcatt ttggatgcgc tgttggatga atccagcctc    1380

ttccccacca acgaggaagt ggaactgagc tggaagattc tggatccaat tcttgaagca    1440

tgggacgccg atggagaacc agaggattac ccagcaggta cgtggggtcc aaagagcgct    1500

gatgaaatgc tttcccgcaa cggtcacacc tggcgcaggc cataa                    1545
```

<210> SEQ ID NO 29
<211> LENGTH: 23
<212> TYPE: DNA
<213> ORGANISM: Artificial Sequence
<220> FEATURE:
<223> OTHER INFORMATION: Primer 2'NCgl1514-5R

<400> SEQUENCE: 29
gatggtagcg tcacgatcct ttc 23

<210> SEQ ID NO 30
<211> LENGTH: 37
<212> TYPE: DNA
<213> ORGANISM: Artificial Sequence
<220> FEATURE:
<223> OTHER INFORMATION: Primer 2'PC7-F(1514)

<400> SEQUENCE: 30
gatcgtgacg ctaccatcgc cggcatagcc taccgat 37

<210> SEQ ID NO 31
<211> LENGTH: 38
<212> TYPE: DNA
<213> ORGANISM: Artificial Sequence
<220> FEATURE:
<223> OTHER INFORMATION: Primer NCgl1514-3F(C7-ATG)

<400> SEQUENCE: 31
aaggaaacac tgatatcatg agcacaaaca cgaccccc 38

<210> SEQ ID NO 32
<211> LENGTH: 484
<212> TYPE: PRT
<213> ORGANISM: Corynebacterium glutamicum

<400> SEQUENCE: 32

Met Thr Asn Gly Asp Asn Leu Ala Gln Ile Gly Val Val Gly Leu Ala
1 5 10 15

Val Met Gly Ser Asn Leu Ala Arg Asn Phe Ala Arg Asn Gly Asn Thr
20 25 30

Val Ala Val Tyr Asn Arg Ser Thr Asp Lys Thr Asp Lys Leu Ile Ala
35 40 45

Asp His Gly Ser Glu Gly Asn Phe Ile Pro Ser Ala Thr Val Glu Glu
50 55 60

Phe Val Ala Ser Leu Glu Lys Pro Arg Arg Ala Ile Ile Met Val Gln
65 70 75 80

Ala Gly Asn Ala Thr Asp Ala Val Ile Asn Gln Leu Ala Asp Ala Met
85 90 95

Asp Glu Gly Asp Ile Ile Ile Asp Gly Gly Asn Ala Leu Tyr Thr Asp
100 105 110

Thr Ile Arg Arg Glu Lys Glu Ile Ser Ala Arg Gly Leu His Phe Val
115 120 125

Gly Ala Gly Ile Ser Gly Gly Glu Glu Gly Ala Leu Asn Gly Pro Ser
130 135 140

Ile Met Pro Gly Gly Pro Ala Lys Ser Tyr Glu Ser Leu Gly Pro Leu
145 150 155 160

Leu Glu Ser Ile Ala Ala Asn Val Asp Gly Thr Pro Cys Val Thr His
165 170 175

Ile Gly Pro Asp Gly Ala Gly His Phe Val Lys Met Val His Asn Gly
180 185 190

```
Ile Glu Tyr Ala Asp Met Gln Val Ile Gly Glu Ala Tyr His Leu Leu
        195                 200                 205

Arg Tyr Ala Ala Gly Met Gln Pro Ala Glu Ile Ala Glu Val Phe Lys
    210                 215                 220

Glu Trp Asn Ala Gly Asp Leu Asp Ser Tyr Leu Ile Glu Ile Thr Ala
225                 230                 235                 240

Glu Val Leu Ser Gln Val Asp Ala Glu Thr Gly Lys Pro Leu Ile Asp
                245                 250                 255

Val Ile Val Asp Ala Ala Gly Gln Lys Gly Thr Gly Arg Trp Thr Val
            260                 265                 270

Lys Ala Ala Leu Asp Leu Gly Ile Ala Thr Thr Gly Ile Gly Glu Ala
        275                 280                 285

Val Phe Ala Arg Ala Leu Ser Gly Ala Thr Ser Gln Arg Ala Ala Ala
    290                 295                 300

Gln Gly Asn Leu Pro Ala Gly Val Leu Thr Asp Leu Glu Ala Leu Gly
305                 310                 315                 320

Val Asp Lys Ala Gln Phe Val Glu Asp Val Arg Arg Ala Leu Tyr Ala
                325                 330                 335

Ser Lys Leu Val Ala Tyr Ala Gln Gly Phe Asp Glu Ile Lys Ala Gly
            340                 345                 350

Ser Asp Glu Asn Asn Trp Asp Val Asp Pro Arg Asp Leu Ala Thr Ile
        355                 360                 365

Trp Arg Gly Gly Cys Ile Ile Arg Ala Lys Phe Leu Asn Arg Ile Val
    370                 375                 380

Glu Ala Tyr Asp Ala Asn Ala Glu Leu Glu Ser Leu Leu Leu Asp Pro
385                 390                 395                 400

Tyr Phe Lys Ser Glu Leu Gly Asp Leu Ile Asp Ser Trp Arg Arg Val
                405                 410                 415

Ile Val Thr Ala Thr Gln Leu Gly Leu Pro Ile Pro Val Phe Ala Ser
            420                 425                 430

Ser Leu Ser Tyr Tyr Asp Ser Leu Arg Ala Glu Arg Leu Pro Ala Ala
        435                 440                 445

Leu Ile Gln Gly Gln Arg Asp Phe Phe Gly Ala His Thr Tyr Lys Arg
    450                 455                 460

Ile Asp Lys Asp Gly Ser Phe His Thr Glu Trp Ser Gly Asp Arg Ser
465                 470                 475                 480

Glu Val Glu Ala


<210> SEQ ID NO 33
<211> LENGTH: 1455
<212> TYPE: DNA
<213> ORGANISM: Corynebacterium glutamicum

<400> SEQUENCE: 33

atgactaatg gagataatct cgcacagatc ggcgttgtag gcctagcagt aatgggctca      60

aacctcgccc gcaacttcgc ccgcaacggc aacactgtcg ctgtctacaa ccgcagcact     120

gacaaaaccg acaagctcat cgccgatcac ggctccgaag gcaacttcat cccttctgca     180

accgtcgaag agttcgtagc atccctggaa aagccacgcc gcgccatcat catggttcag     240

gctggtaacg ccaccgacgc agtcatcaac cagctggcag atgccatgga cgaaggcgac     300

atcatcatcg acggcggcaa cgccctctac accgacacca ttcgtcgcga gaaggaaatc     360

tccgcacgcg gtctccactt cgtcggtgct ggtatctccg gcggcgaaga aggcgcactc     420
```

```
aacggcccat ccatcatgcc tggtggccca gcaaagtcct acgagtccct cggaccactg    480

cttgagtcca tcgctgccaa cgttgacggc accccatgtg tcacccacat cggcccagac    540

ggcgccggcc acttcgtcaa gatggtccac aacggcatcg agtacgccga catgcaggtc    600

atcggcgagg cataccacct tctccgctac gcagcaggca tgcagccagc tgaaatcgct    660

gaggttttca aggaatggaa cgcaggcgac ctggattcct acctcatcga aatcaccgca    720

gaggttctct cccaggtgga tgctgaaacc ggcaagccac taatcgacgt catcgttgac    780

gctgcaggtc agaagggcac cggacgttgg accgtcaagg ctgctcttga tctgggtatt    840

gctaccaccg gcatcggcga agctgttttc gcacgtgcac tctccggcgc aaccagccag    900

cgcgctgcag cacagggcaa cctacctgca ggtgtcctca ccgatctgga agcacttggc    960

gtggacaagg cacagttcgt cgaagacgtt cgccgtgcac tgtacgcatc caagcttgtt   1020

gcttacgcac agggcttcga cgagatcaag gctggctccg acgagaacaa ctgggacgtt   1080

gaccctcgcg acctcgctac catctggcgc ggcggctgca tcattcgcgc taagttcctc   1140

aaccgcatcg tcgaagcata cgatgcaaac gctgaacttg agtccctgct gctcgatcct   1200

tacttcaaga gcgagctcgg cgacctcatc gattcatggc gtcgcgtgat tgtcaccgcc   1260

acccagcttg gcctgccaat cccagtgttc gcttcctccc tgtcctacta cgacagcctg   1320

cgtgcagagc gtctgccagc agccctgatc caaggacagc gcgacttctt cggtgcgcac   1380

acctacaagc gcatcgacaa ggatggctcc ttccacaccg agtggtccgg cgaccgctcc   1440

gaggttgaag cttaa                                                     1455
```

```
<210> SEQ ID NO 34
<211> LENGTH: 42
<212> TYPE: DNA
<213> ORGANISM: Artificial Sequence
<220> FEATURE:
<223> OTHER INFORMATION: Primer NCgl1396-F

<400> SEQUENCE: 34

aaggaaacac tgatatcatg actaatggag ataatctcgc ac                        42


<210> SEQ ID NO 35
<211> LENGTH: 38
<212> TYPE: DNA
<213> ORGANISM: Artificial Sequence
<220> FEATURE:
<223> OTHER INFORMATION: Primer 1'NCgl1396-R

<400> SEQUENCE: 35

gccaaaacag cctcgagtta agcttcaacc tcggagcg                             38


<210> SEQ ID NO 36
<211> LENGTH: 484
<212> TYPE: PRT
<213> ORGANISM: Corynebacterium glutamicum

<400> SEQUENCE: 36

Met Thr Asn Gly Asp Asn Leu Ala Gln Ile Gly Val Val Gly Leu Ala
1               5                   10                  15

Val Met Gly Ser Asn Leu Ala Arg Asn Phe Ala Arg Asn Gly Asn Thr
            20                  25                  30

Val Ala Val Tyr Asn Arg Ser Thr Asp Lys Thr Asp Lys Leu Ile Ala
        35                  40                  45

Asp His Gly Ser Glu Gly Asn Phe Ile Pro Ser Ala Thr Val Glu Glu
    50                  55                  60
```

```
Phe Val Ala Ser Leu Glu Lys Pro Arg Arg Ala Ile Ile Met Val Gln
65                  70                  75                  80

Ala Gly Asn Ala Thr Asp Ala Val Ile Asn Gln Leu Ala Asp Ala Met
                85                  90                  95

Asp Glu Gly Asp Ile Ile Ile Asp Gly Gly Asn Ala Leu Tyr Thr Asp
            100                 105                 110

Thr Ile Arg Arg Glu Lys Glu Ile Ser Ala Arg Gly Leu His Phe Val
        115                 120                 125

Gly Ala Gly Ile Ser Gly Gly Glu Glu Gly Ala Leu Asn Gly Pro Ser
    130                 135                 140

Ile Met Pro Gly Gly Pro Ala Lys Ser Tyr Glu Ser Leu Gly Pro Leu
145                 150                 155                 160

Leu Glu Ser Ile Ala Ala Asn Val Asp Gly Thr Pro Cys Val Thr His
                165                 170                 175

Ile Gly Pro Asp Gly Ala Gly His Phe Val Lys Met Val His Asn Gly
            180                 185                 190

Ile Glu Tyr Ala Asp Met Gln Val Ile Gly Glu Ala Tyr His Leu Leu
        195                 200                 205

Arg Tyr Ala Ala Gly Met Gln Pro Ala Glu Ile Ala Glu Val Phe Lys
    210                 215                 220

Glu Trp Asn Ala Gly Asp Leu Asp Ser Tyr Leu Ile Glu Ile Thr Ala
225                 230                 235                 240

Glu Val Leu Ser Gln Val Asp Ala Glu Thr Gly Lys Pro Leu Ile Asp
                245                 250                 255

Val Ile Val Asp Ala Ala Gly Gln Lys Gly Thr Gly Arg Trp Thr Val
            260                 265                 270

Lys Ala Ala Leu Asp Leu Gly Ile Ala Thr Thr Gly Ile Gly Glu Ala
        275                 280                 285

Val Phe Ala Arg Ala Leu Ser Gly Ala Thr Ser Gln Arg Ala Ala Ala
    290                 295                 300

Gln Gly Asn Leu Pro Ala Gly Val Leu Thr Asp Leu Glu Ala Leu Gly
305                 310                 315                 320

Met Asp Lys Ala Gln Phe Val Glu Asp Val Arg Arg Ala Leu Tyr Ala
                325                 330                 335

Ser Lys Leu Val Ala Tyr Ala Gln Gly Phe Asp Glu Ile Lys Ala Gly
            340                 345                 350

Ser Asp Glu Asn Asn Trp Asp Val Asp Pro Arg Asp Leu Ala Thr Ile
        355                 360                 365

Trp Arg Gly Gly Cys Ile Ile Arg Ala Lys Phe Leu Asn Arg Ile Val
    370                 375                 380

Glu Ala Tyr Asp Ala Asn Ala Glu Leu Glu Ser Leu Leu Leu Asp Pro
385                 390                 395                 400

Tyr Phe Lys Ser Glu Leu Gly Asp Leu Ile Asp Ser Trp Arg Arg Val
                405                 410                 415

Ile Val Thr Ala Thr Gln Leu Gly Leu Pro Ile Pro Val Phe Ala Ser
            420                 425                 430

Ser Leu Ser Tyr Tyr Asp Ser Leu Arg Ala Glu Arg Leu Pro Ala Ala
        435                 440                 445

Leu Ile Gln Gly Gln Arg Asp Phe Phe Gly Ala His Thr Tyr Lys Arg
    450                 455                 460

Ile Asp Lys Asp Gly Ser Phe His Thr Glu Trp Ser Gly Asp Arg Ser
465                 470                 475                 480
```

Glu Val Glu Ala

<210> SEQ ID NO 37
<211> LENGTH: 1455
<212> TYPE: DNA
<213> ORGANISM: Corynebacterium glutamicum

<400> SEQUENCE: 37

```
atgactaatg gagataatct cgcacagatc ggcgttgtag gcctagcagt aatgggctca     60

aacctcgccc gcaacttcgc ccgcaacggc aacactgtcg ctgtctacaa ccgcagcact    120

gacaaaaccg acaagctcat cgccgatcac ggctccgaag gcaacttcat cccttccgca    180

accgtcgaag agttcgtagc atccctggaa aagccacgcc gcgccatcat catggttcag    240

gctggtaacg ccaccgacgc agtcatcaac cagctagcag atgccatgga cgaaggcgac    300

atcatcatcg acggcggcaa cgccctctac accgacacca ttcgtcgcga gaaggaaatc    360

tccgcacgcg gtctccactt cgtcggtgct ggtatctccg gcggcgaaga aggcgcactc    420

aacggcccat ccatcatgcc tggtggccca gcaaagtcct acgagtccct cggaccactg    480

cttgaatcca tcgctgccaa cgttgacggc accccatgtg tcacccacat cggcccagac    540

ggcgccggcc acttcgtcaa gatggtccac aacggcatcg agtacgcgga catgcaggtc    600

atcggcgagg cataccacct tctccgctac gcagcaggca tgcagccagc tgaaatcgct    660

gaggttttca aggaatggaa cgcaggcgac ctggattcct acctcatcga aatcaccgca    720

gaggttctct cccaggtgga tgctgaaacc ggcaagccac tgatcgacgt catcgttgac    780

gctgcaggcc agaagggcac cggacgttgg accgtcaagg ctgctcttga tctgggtatt    840

gctaccaccg gcatcggcga agctgttttc gcacgtgcac tctccggcgc aaccagccag    900

cgcgctgcag cacagggcaa cctacctgca ggtgtcctca ccgatctgga agcacttggc    960

atggacaagg cacagttcgt cgaagacgtt cgccgtgcac tgtacgcatc caagcttgtt   1020

gcttacgcac agggcttcga cgagatcaag gctggctccg acgagaacaa ctgggacgtt   1080

gaccctcgcg acctcgctac catctggcgc ggcggctgca tcattcgcgc taagttcctc   1140

aaccgcatcg tcgaagcata cgatgcaaac gctgaacttg agtccctgct gctcgatcct   1200

tacttcaaga gcgagctcgg cgacctcatc gattcatggc gtcgcgtgat tgtcaccgcc   1260

acccagcttg gcctgccaat cccagtgttc gcttcctccc tgtcctacta cgacagcctg   1320

cgtgcagagc gtctgccagc agccctgatc cagggacagc gcgacttctt cggtgcgcac   1380

acctacaagc gcatcgacaa ggatggctcc ttccacaccg agtggtccgg cgaccgctcc   1440

gaggtggaag cttaa                                                     1455
```

<210> SEQ ID NO 38
<211> LENGTH: 37
<212> TYPE: DNA
<213> ORGANISM: Artificial Sequence
<220> FEATURE:
<223> OTHER INFORMATION: Primer 2'NCgl1396-R

<400> SEQUENCE: 38

```
gccaaaacag cctcgagtta agcttccacc tcggagc                               37
```

<210> SEQ ID NO 39
<211> LENGTH: 510
<212> TYPE: PRT
<213> ORGANISM: Escherichia coli

<400> SEQUENCE: 39

```
Met Arg Ile Gly Ile Pro Arg Glu Arg Leu Thr Asn Glu Thr Arg Val
1               5                   10                  15

Ala Ala Thr Pro Lys Thr Val Glu Gln Leu Leu Lys Leu Gly Phe Thr
            20                  25                  30

Val Ala Val Glu Ser Gly Ala Gly Gln Leu Ala Ser Phe Asp Asp Lys
        35                  40                  45

Ala Phe Val Gln Ala Gly Ala Glu Ile Val Glu Gly Asn Ser Val Trp
    50                  55                  60

Gln Ser Glu Ile Ile Leu Lys Val Asn Ala Pro Leu Asp Asp Glu Ile
65                  70                  75                  80

Ala Leu Leu Asn Pro Gly Thr Thr Leu Val Ser Phe Ile Trp Pro Ala
                85                  90                  95

Gln Asn Pro Glu Leu Met Gln Lys Leu Ala Glu Arg Asn Val Thr Val
            100                 105                 110

Met Ala Met Asp Ser Val Pro Arg Ile Ser Arg Ala Gln Ser Leu Asp
        115                 120                 125

Ala Leu Ser Ser Met Ala Asn Ile Ala Gly Tyr Arg Ala Ile Val Glu
    130                 135                 140

Ala Ala His Glu Phe Gly Arg Phe Phe Thr Gly Gln Ile Thr Ala Ala
145                 150                 155                 160

Gly Lys Val Pro Pro Ala Lys Val Met Val Ile Gly Ala Gly Val Ala
                165                 170                 175

Gly Leu Ala Ala Ile Gly Ala Ala Asn Ser Leu Gly Ala Ile Val Arg
            180                 185                 190

Ala Phe Asp Thr Arg Pro Glu Val Lys Glu Gln Val Gln Ser Met Gly
        195                 200                 205

Ala Glu Phe Leu Glu Leu Asp Phe Lys Glu Glu Ala Gly Ser Gly Asp
    210                 215                 220

Gly Tyr Ala Lys Val Met Ser Asp Ala Phe Ile Lys Ala Glu Met Glu
225                 230                 235                 240

Leu Phe Ala Ala Gln Ala Lys Glu Val Asp Ile Ile Val Thr Thr Ala
                245                 250                 255

Leu Ile Pro Gly Lys Pro Ala Pro Lys Leu Ile Thr Arg Glu Met Val
            260                 265                 270

Asp Ser Met Lys Ala Gly Ser Val Ile Val Asp Leu Ala Ala Gln Asn
        275                 280                 285

Gly Gly Asn Cys Glu Tyr Thr Val Pro Gly Glu Ile Phe Thr Thr Glu
    290                 295                 300

Asn Gly Val Lys Val Ile Gly Tyr Thr Asp Leu Pro Gly Arg Leu Pro
305                 310                 315                 320

Thr Gln Ser Ser Gln Leu Tyr Gly Thr Asn Leu Val Asn Leu Leu Lys
                325                 330                 335

Leu Leu Cys Lys Glu Lys Asp Gly Asn Ile Thr Val Asp Phe Asp Asp
            340                 345                 350

Val Val Ile Arg Gly Val Thr Val Ile Arg Ala Gly Glu Ile Thr Trp
        355                 360                 365

Pro Ala Pro Pro Ile Gln Val Ser Ala Gln Pro Gln Ala Ala Gln Lys
    370                 375                 380

Ala Ala Pro Glu Val Lys Thr Glu Glu Lys Cys Thr Cys Ser Pro Trp
385                 390                 395                 400

Arg Lys Tyr Ala Leu Met Ala Leu Ala Ile Ile Leu Phe Gly Trp Met
                405                 410                 415
```

```
Ala Ser Val Ala Pro Lys Glu Phe Leu Gly His Phe Thr Val Phe Ala
            420                 425                 430

Leu Ala Cys Val Val Gly Tyr Tyr Val Val Trp Asn Val Ser His Ala
        435                 440                 445

Leu His Thr Pro Leu Met Ser Val Thr Asn Ala Ile Ser Gly Ile Ile
    450                 455                 460

Val Val Gly Ala Leu Leu Gln Ile Gly Gln Gly Gly Trp Val Ser Phe
465                 470                 475                 480

Leu Ser Phe Ile Ala Val Leu Ile Ala Ser Ile Asn Ile Phe Gly Gly
                485                 490                 495

Phe Thr Val Thr Gln Arg Met Leu Lys Met Phe Arg Lys Asn
            500                 505                 510


<210> SEQ ID NO 40
<211> LENGTH: 1533
<212> TYPE: DNA
<213> ORGANISM: Escherichia coli

<400> SEQUENCE: 40

atgcgaattg gcataccaag agaacggtta accaatgaaa cccgtgttgc agcaacgcca     60

aaaacagtgg aacagctgct gaaactgggt tttaccgtcg cggtagagag cggcgcgggt    120

caactggcaa gttttgacga taaagcgttt gtgcaagcgg gcgctgaaat tgtagaaggg    180

aatagcgtct ggcagtcaga gatcattctg aaggtcaatg cgccgttaga tgatgaaatt    240

gcgttactga atcctgggac aacgctggtg agttttatct ggcctgcgca gaatccggaa    300

ttaatgcaaa aacttgcgga acgtaacgtg accgtgatgg cgatggactc tgtgccgcgt    360

atctcacgcg cacaatcgct ggacgcacta agctcgatgg cgaacatcgc cggttatcgc    420

gccattgttg aagcggcaca tgaatttggg cgcttcttta ccgggcaaat tactgcggcc    480

gggaaagtgc caccggcaaa agtgatggtg attggtgcgg gtgttgcagg tctggccgcc    540

attggcgcag caaacagtct cggcgcgatt gtgcgtgcat tcgacacccg cccggaagtg    600

aaagaacaag ttcaaagtat gggcgcggaa ttcctcgagc tggattttaa agaggaagct    660

ggcagcggcg atggctatgc caaagtgatg tcggacgcgt tcatcaaagc ggaaatggaa    720

ctctttgccg cccaggcaaa agaggtcgat atcattgtca ccaccgcgct tattccaggc    780

aaaccagcgc cgaagctaat tacccgtgaa atggttgact ccatgaaggc gggcagtgtg    840

attgtcgacc tggcagccca aaacggcggc aactgtgaat acaccgtgcc gggtgaaatc    900

ttcactacgg aaaatggtgt caaagtgatt ggttataccg atcttccggg ccgtctgccg    960

acgcaatcct cacagcttta cggcacaaac ctcgttaatc tgctgaaact gttgtgcaaa   1020

gagaaagacg gcaatatcac tgttgatttt gatgatgtgg tgattcgcgg cgtgaccgtg   1080

atccgtgcgg gcgaaattac ctggccggca ccgccgattc aggtatcagc tcagccgcag   1140

gcggcacaaa aagcggcacc ggaagtgaaa actgaggaaa aatgtacctg ctcaccgtgg   1200

cgtaaatacg cgttgatggc gctggcaatc attcttttg gctggatggc aagcgttgcg    1260

ccgaaagaat tccttgggca cttcaccgtt ttcgcgctgg cctgcgttgt cggttattac   1320

gtggtgtgga atgtatcgca cgcgctgcat acaccgttga tgtcggtcac caacgcgatt   1380

tcagggatta ttgttgtcgg agcactgttg cagattggcc agggcggctg ggttagcttc   1440

cttagtttta tcgcggtgct tatagccagc attaatattt tcggtggctt caccgtgact   1500

cagcgcatgc tgaaaatgtt ccgcaaaaat taa                                1533
```

<210> SEQ ID NO 41
<211> LENGTH: 462
<212> TYPE: PRT
<213> ORGANISM: Escherichia coli

<400> SEQUENCE: 41

```
Met Ser Gly Gly Leu Val Thr Ala Ala Tyr Ile Val Ala Ala Ile Leu
1               5                   10                  15

Phe Ile Phe Ser Leu Ala Gly Leu Ser Lys His Glu Thr Ser Arg Gln
            20                  25                  30

Gly Asn Asn Phe Gly Ile Ala Gly Met Ala Ile Ala Leu Ile Ala Thr
        35                  40                  45

Ile Phe Gly Pro Asp Thr Gly Asn Val Gly Trp Ile Leu Leu Ala Met
    50                  55                  60

Val Ile Gly Gly Ala Ile Gly Ile Arg Leu Ala Lys Lys Val Glu Met
65                  70                  75                  80

Thr Glu Met Pro Glu Leu Val Ala Ile Leu His Ser Phe Val Gly Leu
                85                  90                  95

Ala Ala Val Leu Val Gly Phe Asn Ser Tyr Leu His His Asp Ala Gly
            100                 105                 110

Met Ala Pro Ile Leu Val Asn Ile His Leu Thr Glu Val Phe Leu Gly
        115                 120                 125

Ile Phe Ile Gly Ala Val Thr Phe Thr Gly Ser Val Val Ala Phe Gly
    130                 135                 140

Lys Leu Cys Gly Lys Ile Ser Ser Lys Pro Leu Met Leu Pro Asn Arg
145                 150                 155                 160

His Lys Met Asn Leu Ala Ala Leu Val Val Ser Phe Leu Leu Leu Ile
                165                 170                 175

Val Phe Val Arg Thr Asp Ser Val Gly Leu Gln Val Leu Ala Leu Leu
            180                 185                 190

Ile Met Thr Ala Ile Ala Leu Val Phe Gly Trp His Leu Val Ala Ser
        195                 200                 205

Ile Gly Gly Ala Asp Met Pro Val Val Val Ser Met Leu Asn Ser Tyr
    210                 215                 220

Ser Gly Trp Ala Ala Ala Ala Ala Gly Phe Met Leu Ser Asn Asp Leu
225                 230                 235                 240

Leu Ile Val Thr Gly Ala Leu Val Gly Ser Ser Gly Ala Ile Leu Ser
                245                 250                 255

Tyr Ile Met Cys Lys Ala Met Asn Arg Ser Phe Ile Ser Val Ile Ala
            260                 265                 270

Gly Gly Phe Gly Thr Asp Gly Ser Ser Thr Gly Asp Asp Gln Glu Val
        275                 280                 285

Gly Glu His Arg Glu Ile Thr Ala Glu Glu Thr Ala Glu Leu Leu Lys
    290                 295                 300

Asn Ser His Ser Val Ile Ile Thr Pro Gly Tyr Gly Met Ala Val Ala
305                 310                 315                 320

Gln Ala Gln Tyr Pro Val Ala Glu Ile Thr Glu Lys Leu Arg Ala Arg
                325                 330                 335

Gly Ile Asn Val Arg Phe Gly Ile His Pro Val Ala Gly Arg Leu Pro
            340                 345                 350

Gly His Met Asn Val Leu Leu Ala Glu Ala Lys Val Pro Tyr Asp Ile
        355                 360                 365

Val Leu Glu Met Asp Glu Ile Asn Asp Asp Phe Ala Asp Thr Asp Thr
    370                 375                 380
```

```
Val Leu Val Ile Gly Ala Asn Asp Thr Val Asn Pro Ala Ala Gln Asp
385                 390                 395                 400

Asp Pro Lys Ser Pro Ile Ala Gly Met Pro Val Leu Glu Val Trp Lys
                405                 410                 415

Ala Gln Asn Val Ile Val Phe Lys Arg Ser Met Asn Thr Gly Tyr Ala
            420                 425                 430

Gly Val Gln Asn Pro Leu Phe Phe Lys Glu Asn Thr His Met Leu Phe
        435                 440                 445

Gly Asp Ala Lys Ala Ser Val Asp Ala Ile Leu Lys Ala Leu
    450                 455                 460


<210> SEQ ID NO 42
<211> LENGTH: 1389
<212> TYPE: DNA
<213> ORGANISM: Escherichia coli

<400> SEQUENCE: 42

atgtctggag gattagttac agctgcatac attgttgccg cgatcctgtt tatcttcagt     60

ctggccggtc tttcgaaaca tgaaacgtct cgccagggta acaacttcgg tatcgccggg    120

atggcgattg cgttaatcgc aaccattttt ggaccggata cgggtaatgt tggctggatc    180

ttgctggcga tggtcattgg tggggcaatt ggtatccgtc tggcgaagaa agttgaaatg    240

accgaaatgc cagaactggt ggcgatcctg catagcttcg tgggtctggc ggcagtgctg    300

gttggcttta acagctatct gcatcatgac gcgggaatgg caccgattct ggtcaatatt    360

cacctgacgg aagtgttcct cggtatcttc atcggggcgg taacgttcac gggttcggtg    420

gtggcgttcg gcaaactgtg tggcaagatt tcgtctaaac cattgatgct gccaaaccgt    480

cacaaaatga acctggcggc tctggtcgtt tccttcctgc tgctgattgt atttgttcgc    540

acggacagcg tcggcctgca agtgctggca ttgctgataa tgaccgcaat tgcgctggta    600

ttcggctggc atttagtcgc ctccatcggt ggtgcagata tgccagtggt ggtgtcgatg    660

ctgaactcgt actccggctg ggcggctgcg gctgcgggct ttatgctcag caacgacctg    720

ctgattgtga ccggtgcgct ggtcggttct tcgggggcta tcctttctta cattatgtgt    780

aaggcgatga accgttcctt tatcagcgtt attgcgggtg gtttcggcac cgacggctct    840

tctactggcg atgatcagga agtgggtgag caccgcgaaa tcaccgcaga agagacagcg    900

gaactgctga aaaactccca ttcagtgatc attactccgg ggtacggcat ggcagtcgcg    960

caggcgcaat atcctgtcgc tgaaattact gagaaattgc gcgctcgtgg tattaatgtg   1020

cgtttcggta tccacccggt cgcggggcgt ttgcctggac atatgaacgt attgctggct   1080

gaagcaaaag taccgtatga catcgtgctg gaaatggacg agatcaatga tgactttgct   1140

gataccgata ccgtactggt gattggtgct aacgatacgg ttaacccggc ggcgcaggat   1200

gatccgaaga gtccgattgc tggtatgcct gtgctggaag tgtggaaagc gcagaacgtg   1260

attgtcttta aacgttcgat gaacactggc tatgctggtg tgcaaaaccc gctgttcttc   1320

aaggaaaaca cccacatgct gtttggtgac gccaaagcca gcgtggatgc aatcctgaaa   1380

gctctgtaa                                                            1389


<210> SEQ ID NO 43
<211> LENGTH: 42
<212> TYPE: DNA
<213> ORGANISM: Artificial Sequence
<220> FEATURE:
<223> OTHER INFORMATION: Primer Y75_p1579-F
```

<400> SEQUENCE: 43
aaggaaacac tgatatcatg cgaattggca taccaagaga ac 42

<210> SEQ ID NO 44
<211> LENGTH: 42
<212> TYPE: DNA
<213> ORGANISM: Artificial Sequence
<220> FEATURE:
<223> OTHER INFORMATION: Primer Y75_p1578-R

<400> SEQUENCE: 44
gccaaaacag cctcgagtta cagagctttc aggattgcat cc 42

<210> SEQ ID NO 45
<211> LENGTH: 167
<212> TYPE: PRT
<213> ORGANISM: Corynebacterium glutamicum

<400> SEQUENCE: 45

Met Ser Ala Ala Glu Gly Leu His Ile Val Val Met Gly Val Ser Gly
1 5 10 15

Cys Gly Lys Ser Ser Val Gly Lys Ala Leu Ala Ala Glu Leu Gly Ile
20 25 30

Glu Tyr Lys Asp Gly Asp Glu Leu His Pro Gln Glu Asn Ile Asp Lys
35 40 45

Met Ala Ser Gly Gln Ala Leu Asp Asp Asp Asp Arg Ala Trp Trp Leu
50 55 60

Val Gln Val Gly Lys Trp Leu Arg Asp Arg Pro Ser Gly Val Ile Ala
65 70 75 80

Cys Ser Ala Leu Lys Arg Ser Tyr Arg Asp Leu Leu Arg Thr Lys Cys
85 90 95

Pro Gly Thr Val Phe Val His Leu His Gly Asp Tyr Asp Leu Leu Leu
100 105 110

Ser Arg Met Lys Ala Arg Glu Asp His Phe Met Pro Ser Thr Leu Leu
115 120 125

Asp Ser Gln Phe Ala Thr Leu Glu Pro Leu Glu Asp Asp Glu Asp Gly
130 135 140

Lys Val Phe Asp Val Ala His Thr Ile Ser Glu Leu Ala Ala Gln Ser
145 150 155 160

Ala Glu Trp Val Arg Asn Lys
165

<210> SEQ ID NO 46
<211> LENGTH: 504
<212> TYPE: DNA
<213> ORGANISM: Corynebacterium glutamicum

<400> SEQUENCE: 46
atgtcagcag ccgaaggctt acatattgtc gtcatgggcg tttctggctg cggcaaatcc 60
tccgtcggta aagccctagc agcggagctc ggaatcgaat acaaagacgg cgacgaactt 120
cacccccagg aaaacatcga caagatggcc tccggccagg cacttgacga cgacgaccgt 180
gcatggtggc tagtccaggt tggcaagtgg ctccgcgacc gaccaagcgg cgtcatcgca 240
tgctccgccc tcaagcgctc ctaccgcgat ctcctgcgca ccaaatgccc aggaaccgtc 300
ttcgtccacc tccacggcga ctacgatctc ctactttccc gcatgaaggc ccgcgaagat 360
cacttcatgc catccacctt gctagattcc caatttgcaa ccctcgagcc gctcgaagat 420
gacgaagatg gcaaggtttt cgacgttgcc cacaccatca gcgaactggc cgcccaatct 480
gcagagtggg ttcgcaacaa ataa 504

<210> SEQ ID NO 47
<211> LENGTH: 37
<212> TYPE: DNA
<213> ORGANISM: Artificial Sequence
<220> FEATURE:
<223> OTHER INFORMATION: Primer NCgl2399-del-5F

<400> SEQUENCE: 47
ccggggatcc tctagagccc acgctttgta tcaatgg 37

<210> SEQ ID NO 48
<211> LENGTH: 20
<212> TYPE: DNA
<213> ORGANISM: Artificial Sequence
<220> FEATURE:
<223> OTHER INFORMATION: Primer NCgl2399-del-5R

<400> SEQUENCE: 48
gaagttcgtc gccgtctttg 20

<210> SEQ ID NO 49
<211> LENGTH: 33
<212> TYPE: DNA
<213> ORGANISM: Artificial Sequence
<220> FEATURE:
<223> OTHER INFORMATION: Primer NCgl2399-del-3F

<400> SEQUENCE: 49
gacggcgacg aacttcggcc gcccaatctg cag 33

<210> SEQ ID NO 50
<211> LENGTH: 34
<212> TYPE: DNA
<213> ORGANISM: Artificial Sequence
<220> FEATURE:
<223> OTHER INFORMATION: Primer NCgl2399-del-3R

<400> SEQUENCE: 50
gcaggtcgac tctagagggt ggggtctgct ttgg 34

<210> SEQ ID NO 51
<211> LENGTH: 80
<212> TYPE: PRT
<213> ORGANISM: Corynebacterium glutamicum

<400> SEQUENCE: 51

Met Ser Ala Ala Glu Gly Leu His Ile Val Val Met Gly Val Ser Gly
1 5 10 15

Cys Gly Lys Ser Ser Val Gly Glu Ala Leu Ala Ala Glu Leu Gly Ile
20 25 30

Glu Tyr Lys Asp Gly Asp Glu Leu His Pro Gln Glu Asn Ile Asp Lys
35 40 45

Met Ala Ser Gly Gln Ala Leu Asp Asp Asp Asp Arg Ala Trp Trp Leu
50 55 60

Val Gln Val Gly Lys Trp Leu Arg Asp Arg Pro Ser Asp Val Ile Ala
65 70 75 80

<210> SEQ ID NO 52
<211> LENGTH: 504
<212> TYPE: DNA

```
<213> ORGANISM: Corynebacterium glutamicum

<400> SEQUENCE: 52

atgtcagcag ccgaaggctt acatattgtc gtcatgggag tttccggctg cggcaaatcc     60

tccgtcggcg aagccctagc agcggagctc ggaatcgaat acaaagacgg cgacgaactt    120

cacccccagg aaaacatcga caagatggcc tccggccagg cacttgacga cgacgaccgt    180

gcatggtggc tagtccaggt tggcaagtgg ctccgcgacc gaccaagcga cgtcatcgca    240

tgctccgccc tcaaacgctc ctaccgcgat ctcctgcgca ccaaatgccc aggaaccgtc    300

ttcgtccacc tccacggcga ctacgatctc ctactttccc gcatgaaggc ccgcgaagat    360

cacttcatgc catccacctt gctagattcc caatttgcaa ccctcgagcc actcgaagat    420

ggcgaagatg gcaaggtttt cgacgttgcc cacaccatca gcgaactggc cgcccaatct    480

gcagaatggg ttcgcaacaa ataa                                           504


<210> SEQ ID NO 53
<211> LENGTH: 494
<212> TYPE: PRT
<213> ORGANISM: Corynebacterium glutamicum

<400> SEQUENCE: 53

Met Gly Ser Ile Pro Thr Met Ser Ile Pro Phe Asp Asp Ser Arg Gly
1               5                   10                  15

Pro Tyr Val Leu Ala Met Asp Ile Gly Ser Thr Ala Ser Arg Gly Gly
            20                  25                  30

Leu Tyr Asp Ala Ser Gly Cys Pro Ile Lys Gly Thr Lys Gln Arg Glu
        35                  40                  45

Ser His Glu Phe Thr Thr Gly Glu Gly Val Ser Thr Ile Asp Ala Asp
    50                  55                  60

Gln Val Val Ser Glu Ile Thr Ser Val Ile Asn Gly Ile Leu Asn Ala
65                  70                  75                  80

Ala Asp His His Asn Ile Lys Asp Gln Ile Ala Ala Val Ala Leu Asp
                85                  90                  95

Ser Phe Ala Ser Ser Leu Ile Leu Val Asp Gly Glu Gly Asn Ala Leu
            100                 105                 110

Thr Pro Cys Ile Thr Tyr Ala Asp Ser Arg Ser Ala Gln Tyr Val Glu
        115                 120                 125

Gln Leu Arg Ala Glu Ile Asp Glu Glu Ala Tyr His Gly Arg Thr Gly
    130                 135                 140

Val Cys Leu His Thr Ser Tyr His Pro Ser Arg Leu Leu Trp Leu Lys
145                 150                 155                 160

Thr Glu Phe Glu Glu Glu Phe Asn Lys Ala Lys Tyr Val Met Thr Ile
                165                 170                 175

Gly Glu Tyr Val Tyr Phe Lys Leu Ala Gly Ile Thr Gly Met Ala Thr
            180                 185                 190

Ser Ile Ala Ala Trp Ser Gly Ile Leu Asp Ala His Thr Gly Glu Leu
        195                 200                 205

Asp Leu Thr Ile Leu Glu His Ile Gly Val Asp Pro Ala Leu Phe Gly
    210                 215                 220

Glu Ile Arg Asn Pro Asp Glu Pro Ala Thr Asp Ala Lys Val Val Asp
225                 230                 235                 240

Lys Lys Trp Lys His Leu Glu Glu Ile Pro Trp Phe His Ala Ile Pro
                245                 250                 255

Asp Gly Trp Pro Ser Asn Ile Gly Pro Gly Ala Val Asp Ser Lys Thr
```

```
            260                 265                 270

Val Ala Val Ala Ala Ala Thr Ser Gly Ala Met Arg Val Ile Leu Pro
        275                 280                 285

Ser Val Pro Glu Gln Ile Pro Ser Gly Leu Trp Cys Tyr Arg Val Ser
    290                 295                 300

Arg Asp Gln Cys Ile Val Gly Gly Ala Leu Asn Asp Val Gly Arg Ala
305                 310                 315                 320

Val Thr Trp Leu Glu Arg Thr Ile Ile Lys Pro Glu Asn Leu Asp Glu
                325                 330                 335

Val Leu Ile Arg Glu Pro Leu Glu Gly Thr Pro Ala Val Leu Pro Phe
            340                 345                 350

Phe Ser Gly Glu Arg Ser Ile Gly Trp Ala Ala Ser Ala Gln Ala Thr
        355                 360                 365

Ile Thr Asn Ile Gln Glu Gln Thr Gly Pro Glu His Leu Trp Arg Gly
    370                 375                 380

Val Phe Glu Ala Leu Ala Leu Ser Tyr Gln Arg Val Trp Glu His Met
385                 390                 395                 400

Gly Lys Ala Gly Ala Ala Pro Glu Arg Val Ile Ala Ser Gly Arg Val
                405                 410                 415

Ser Thr Asp His Pro Glu Phe Leu Ala Met Leu Ser Asp Ala Leu Asp
            420                 425                 430

Thr Pro Val Ile Pro Leu Glu Met Lys Arg Ala Thr Leu Arg Gly Thr
        435                 440                 445

Ala Leu Ile Val Leu Glu Gln Leu Glu Pro Gly Gly Thr Arg Ala Thr
    450                 455                 460

Pro Pro Phe Gly Thr Thr His Gln Pro Arg Phe Ala His His Tyr Ser
465                 470                 475                 480

Lys Ala Arg Glu Leu Phe Asp Ala Leu Tyr Leu Lys Leu Val
                485                 490
```

<210> SEQ ID NO 54
<211> LENGTH: 1485
<212> TYPE: DNA
<213> ORGANISM: Corynebacterium glutamicum

<400> SEQUENCE: 54

```
atgggatcaa ttccaacaat gtccatccct tttgatgact cacgtggacc ttatgtcctt     60

gctatggata ttggttccac tgcatcacga ggtggacttt atgatgcttc cggctgccca    120

atcaaaggca ccaagcagcg cgaatcccat gaattcacca ccggtgaggg cgtttccacc    180

attgatgctg accaggtggt ttcggagatc acctcagtta ttaatggcat tttgaacgcg    240

gctgatcatc acaacatcaa agatcagatc gccgctgtcg cgctagattc ttttgcatcc    300

tcattaatct tggtcgatgg tgaaggcaat gcgctcaccc cgtgcattac ctacgcggat    360

tctcgttctg cacagtatgt ggagcagctg cgcgcggaaa tcgatgagga ggcctaccac    420

ggccgcaccg gcgtctgcct gcacacctcc taccacccat cgcgcctgct gtggctgaaa    480

actgagttcg aggaagagtt caacaaagcc aagtatgtga tgaccatcgg tgagtacgtc    540

tacttcaaac ttgcaggcat caccggaatg gctacttcga ttgccgcgtg gagtggcatt    600

ttggacgccc ataccggcga acttgatctg actatcttgg agcacatcgg tgttgatccg    660

gctctgttcg gtgagatcag aaaccctgat gaaccagcca ccgatgccaa agttgtcgac    720

aaaaagtgga agcacctgga agaaatccct tggttccatg ccattccaga cggctggcct    780

tccaacattg gcccaggcgc cgtggattct aaaaccgtcg cagtcgccgc cgctacatcc    840
```

```
ggcgccatgc gcgtgatcct tccgagcgtt cccgaacaga tcccctctgg cctgtggtgt    900

taccgcgttt cccgcgacca gtgcatcgtt ggtggcgcac tcaacgacgt cggacgcgcc    960

gtcacctggc tggaacgcac cattatcaag cctgaaaacc tcgacgaagt gctgatccgc   1020

gaacccctcg aaggcacccc agctgtcctg ccgttcttct ccggggaacg ctccatcggc   1080

tgggcagcct cagcgcaggc cacgatcacc aacattcagg aacaaaccgg ccctgaacac   1140

ttgtggcgcg gcgttttcga agccctcgca ctctcctacc agcgcgtttg ggaacacatg   1200

gggaaagccg gcgcagcccc tgaacgggtc atcgcatcag gacgagtctc caccgaccac   1260

ccagaattcc tcgcgatgct ttccgacgcc ctcgacaccc cagtcatccc tctggaaatg   1320

aagcgcgcca ccctccgcgg caccgcactt atcgtccttg agcagctcga accaggcggc   1380

acgcgcgcga cgccaccatt cggcacgacg catcagccgc gctttgcgca ccattactcc   1440

aaggcaagag agcttttcga cgccctctac ctcaagttgg tctag                   1485
```

<210> SEQ ID NO 55
<211> LENGTH: 35
<212> TYPE: DNA
<213> ORGANISM: Artificial Sequence
<220> FEATURE:
<223> OTHER INFORMATION: Primer NCgl2905-del-5F

<400> SEQUENCE: 55

```
ccggggatcc tctagactgg gtcgtggcat aagaa                                35
```

<210> SEQ ID NO 56
<211> LENGTH: 19
<212> TYPE: DNA
<213> ORGANISM: Artificial Sequence
<220> FEATURE:
<223> OTHER INFORMATION: Primer NCgl2905-del-5R

<400> SEQUENCE: 56

```
gtgcctttga ttgggcagc                                                  19
```

<210> SEQ ID NO 57
<211> LENGTH: 37
<212> TYPE: DNA
<213> ORGANISM: Artificial Sequence
<220> FEATURE:
<223> OTHER INFORMATION: Primer NCgl2905-del-3F

<400> SEQUENCE: 57

```
gcccaatcaa aggcacgaat tcctcgcgat gctttcc                              37
```

<210> SEQ ID NO 58
<211> LENGTH: 38
<212> TYPE: DNA
<213> ORGANISM: Artificial Sequence
<220> FEATURE:
<223> OTHER INFORMATION: Primer NCgl2905-del-3R

<400> SEQUENCE: 58

```
gcaggtcgac tctagactag accaacttga ggtagagg                             38
```

<210> SEQ ID NO 59
<211> LENGTH: 494
<212> TYPE: PRT
<213> ORGANISM: Corynebacterium glutamicum

<400> SEQUENCE: 59

-continued

```
Met Gly Ser Ile Pro Thr Met Ser Ile Pro Phe Asp Asp Ser Arg Gly
1               5                   10                  15

Pro Tyr Val Leu Ala Met Asp Ile Gly Ser Thr Ala Ser Arg Gly Gly
            20                  25                  30

Leu Tyr Asp Ala Ser Gly Cys Pro Ile Lys Gly Thr Lys Gln Arg Glu
        35                  40                  45

Ser His Glu Phe Thr Thr Gly Glu Gly Val Ser Thr Ile Asp Ala Asp
    50                  55                  60

Gln Val Val Ser Glu Ile Thr Ser Val Ile Asn Gly Val Leu Asn Ala
65                  70                  75                  80

Ala Asp His His Asn Ile Lys Asp Gln Ile Ala Ala Val Ala Leu Asp
                85                  90                  95

Ser Phe Ala Ser Ser Leu Ile Leu Val Asp Gly Glu Gly Asn Ala Leu
            100                 105                 110

Thr Pro Cys Ile Thr Tyr Ala Asp Ser Arg Ser Ala Gln Tyr Val Glu
        115                 120                 125

Gln Leu Arg Ala Asp Ile Asp Glu Glu Ala Tyr His Gly Arg Thr Gly
    130                 135                 140

Val Arg Leu His Thr Ser Tyr His Pro Ser Arg Leu Leu Trp Leu Lys
145                 150                 155                 160

Thr Glu Phe Glu Glu Glu Phe Asn Lys Ala Lys Tyr Val Met Thr Ile
                165                 170                 175

Gly Glu Tyr Val Tyr Phe Lys Leu Ala Gly Leu Thr Gly Met Ala Thr
            180                 185                 190

Ser Ile Ala Ala Trp Ser Gly Ile Leu Asp Ala His Thr Gly Glu Leu
        195                 200                 205

Asp Leu Thr Ile Leu Glu His Ile Gly Val Asp Pro Ala Leu Phe Gly
    210                 215                 220

Glu Ile Arg Asn Pro Asp Glu Pro Ala Thr Asp Ala Lys Val Val Asp
225                 230                 235                 240

Lys Lys Trp Lys His Leu Glu Glu Ile Pro Trp Phe His Ala Ile Pro
                245                 250                 255

Asp Gly Trp Pro Ser Asn Ile Gly Pro Gly Ala Val Asp Ser Lys Thr
            260                 265                 270

Val Ala Val Ala Val Ala Thr Ser Gly Ala Met Arg Val Ile Leu Pro
        275                 280                 285

Ser Val Pro Glu Gln Ile Pro Ser Gly Leu Trp Cys Tyr Arg Val Ser
    290                 295                 300

Arg Asp Gln Cys Ile Val Gly Gly Ala Leu Asn Asp Val Gly Arg Ala
305                 310                 315                 320

Val Thr Trp Leu Glu Arg Thr Ile Ile Lys Pro Glu Asn Leu Asp Glu
                325                 330                 335

Val Leu Ile Cys Glu Pro Leu Glu Gly Thr Pro Ala Val Leu Pro Phe
            340                 345                 350

Phe Ser Gly Glu Arg Ser Ile Gly Trp Ala Ala Ser Ala Gln Ala Thr
        355                 360                 365

Ile Thr Asn Ile Gln Glu Gln Thr Gly Pro Glu His Leu Trp Arg Gly
    370                 375                 380

Val Phe Glu Ala Leu Ala Leu Ser Tyr Gln Arg Val Trp Glu His Met
385                 390                 395                 400

Glu Lys Ala Gly Ala Ala Pro Glu Arg Val Ile Ala Ser Gly Arg Val
                405                 410                 415

Ser Thr Asp His Pro Glu Phe Leu Ala Met Leu Ser Asp Ala Leu Asp
```

```
        420                 425                 430

Thr Pro Val Ile Pro Leu Glu Met Lys Arg Ala Thr Leu Arg Gly Thr
        435                 440                 445

Ala Leu Ile Val Leu Glu Gln Leu Glu Pro Gly Gly Thr Arg Ala Thr
    450                 455                 460

Pro Pro Phe Gly Thr Thr His Gln Pro Arg Phe Ala His Tyr Tyr Ser
465                 470                 475                 480

Lys Ala Arg Glu Leu Phe Asp Ala Leu Tyr Leu Lys Leu Val
                485                 490
```

<210> SEQ ID NO 60
<211> LENGTH: 1485
<212> TYPE: DNA
<213> ORGANISM: Corynebacterium glutamicum

<400> SEQUENCE: 60

```
atgggatcaa ttccaacaat gtccatccct ttcgatgact cacgtggacc ttatgtcctt     60

gcgatggata ttggctccac tgcatcacga ggtggacttt atgatgcttc cggctgccca    120

atcaaaggca ccaagcagcg cgaatcccat gaattcacca ccggtgaggg cgtttccacc    180

attgatgctg accaggtggt ttcagagatc acctcagtta ttaatggcgt tttgaacgcg    240

gctgatcatc acaacatcaa agatcagatc gccgctgtgg cgcttgattc ttttgcatcc    300

tcactaatcc tggttgatgg tgaaggcaat gcactcaccc catgcatcac ctacgcggat    360

tctcgttctg cgcaatacgt ggagcagctg cgcgcagaca tcgatgagga ggcctaccac    420

ggccgcaccg gcgtccgcct gcacacctcc taccatccat cgcgtctgct gtggctgaaa    480

actgagttcg aggaagaatt caacaaagcc aagtacgtga tgaccatcgg tgagtacgtc    540

tacttcaaac ttgcaggcct caccggaatg gctacttcga ttgccgcgtg gagtggcatt    600

ttggacgccc ataccggcga acttgatctg actatcttgg agcacatcgg tgttgatccg    660

gctctgttcg gtgagatcag aaaccctgat gaaccagcca ccgatgccaa agttgtcgac    720

aaaaagtgga agcacctgga agaaatccct tggttccatg ccattccaga cggctggcct    780

tccaacattg gcccaggcgc cgtggattct aaaaccgtcg cagtcgccgt cgctacatcc    840

ggcgccatgc gcgtgatcct tccgagcgtt cccgaacaga tcccctctgg cctgtggtgt    900

taccgcgttt cccgcgacca gtgcatcgtt ggtggcgcac tcaacgacgt cggacgcgcc    960

gtcacctggc tggaacgcac catcatcaag cctgaaaacc tcgacgaagt gctgatctgc   1020

gaacccctcg aaggcacccc agctgtcctg ccgttcttct ccggggaacg ctccatcggc   1080

tgggcagcct cagcgcaggc cacgatcacc aacattcagg aacaaaccgg ccctgaacac   1140

ttgtggcgcg gcgttttcga agccctcgca ctctcctacc agcgcgtttg ggaacacatg   1200

gagaaagccg gcgcagcccc tgaacgggtc atcgcatcag gacgagtctc caccgaccac   1260

ccagaattcc tcgcgatgct ttccgatgcc ctcgacaccc cagtcattcc tctggaaatg   1320

aagcgcgcca ccctccgcgg caccgcactc atcgtccttg agcagctcga accaggcggc   1380

acgcgcgcga cgccaccatt cggcacgacg catcagccgc gctttgcgca ctattactcc   1440

aaggcaagag agcttttcga cgccctctac ctcaagttgg tctag                   1485
```

<210> SEQ ID NO 61
<211> LENGTH: 400
<212> TYPE: PRT
<213> ORGANISM: Escherichia coli

<400> SEQUENCE: 61

```
Met Thr Gln Phe Ala Ser Pro Val Leu His Ser Leu Leu Asp Thr Asp
1               5                   10                  15

Ala Tyr Lys Leu His Met Gln Gln Ala Val Phe His His Tyr Tyr Asp
            20                  25                  30

Val His Val Ala Ala Glu Phe Arg Cys Arg Gly Asp Asp Leu Leu Gly
        35                  40                  45

Ile Tyr Ala Asp Ala Ile Arg Glu Gln Val Gln Ala Met Gln His Leu
    50                  55                  60

Arg Leu Gln Asp Asp Glu Tyr Gln Trp Leu Ser Ala Leu Pro Phe Phe
65                  70                  75                  80

Lys Ala Asp Tyr Leu Asn Trp Leu Arg Glu Phe Arg Phe Asn Pro Glu
                85                  90                  95

Gln Val Thr Val Ser Asn Asp Asn Gly Lys Leu Asp Ile Arg Leu Ser
            100                 105                 110

Gly Pro Trp Arg Glu Val Ile Leu Trp Glu Val Pro Leu Leu Ala Val
        115                 120                 125

Ile Ser Glu Met Val His Arg Tyr Arg Ser Pro Gln Ala Asp Val Ala
    130                 135                 140

Gln Ala Leu Asp Thr Leu Glu Ser Lys Leu Val Asp Phe Ser Ala Leu
145                 150                 155                 160

Thr Ala Gly Leu Asp Met Ser Arg Phe His Leu Met Asp Phe Gly Thr
                165                 170                 175

Arg Arg Arg Phe Ser Arg Glu Val Gln Glu Thr Ile Val Lys Arg Leu
            180                 185                 190

Gln Gln Glu Ser Trp Phe Val Gly Thr Ser Asn Tyr Asp Leu Ala Arg
        195                 200                 205

Arg Leu Ser Leu Thr Pro Met Gly Thr Gln Ala His Glu Trp Phe Gln
    210                 215                 220

Ala His Gln Gln Ile Ser Pro Asp Leu Ala Asn Ser Gln Arg Ala Ala
225                 230                 235                 240

Leu Ala Ala Trp Leu Glu Glu Tyr Pro Asp Gln Leu Gly Ile Ala Leu
                245                 250                 255

Thr Asp Cys Ile Thr Met Asp Ala Phe Leu Arg Asp Phe Gly Val Glu
            260                 265                 270

Phe Ala Ser Arg Tyr Gln Gly Leu Arg His Asp Ser Gly Asp Pro Val
        275                 280                 285

Glu Trp Gly Glu Lys Ala Ile Ala His Tyr Glu Lys Leu Gly Ile Asp
    290                 295                 300

Pro Gln Ser Lys Thr Leu Val Phe Ser Asp Asn Leu Asp Leu Arg Lys
305                 310                 315                 320

Ala Val Glu Leu Tyr Arg His Phe Ser Ser Arg Val Gln Leu Ser Phe
                325                 330                 335

Gly Ile Gly Thr Arg Leu Thr Cys Asp Ile Pro Gln Val Lys Pro Leu
            340                 345                 350

Asn Ile Val Ile Lys Leu Val Glu Cys Asn Gly Lys Pro Val Ala Lys
        355                 360                 365

Leu Ser Asp Ser Pro Gly Lys Thr Ile Cys His Asp Lys Ala Phe Val
    370                 375                 380

Arg Ala Leu Arg Lys Ala Phe Asp Leu Pro His Ile Lys Lys Ala Ser
385                 390                 395                 400
```

<210> SEQ ID NO 62
<211> LENGTH: 1203

<212> TYPE: DNA
<213> ORGANISM: Escherichia coli

<400> SEQUENCE: 62
atgacacaat tcgcttctcc tgttctgcac tcgttgctgg atacagatgc ttataagttg 60
catatgcagc aagccgtgtt tcatcactat tacgatgtgc atgtcgcggc ggagtttcgt 120
tgccgaggtg acgatctgct gggtatttat gccgatgcta ttcgtgaaca ggttcaggcg 180
atgcagcacc tgcgcctgca ggatgatgaa tatcagtggc tttctgccct gcctttcttt 240
aaggccgact atcttaactg gttacgcgag ttccgcttta acccggaaca agtcaccgtg 300
tccaacgata atggcaagct ggatattcgt ttaagcggcc cgtggcgtga agtcatcctc 360
tgggaagttc ctttgctggc ggttatcagt gaaatggtac atcgctatcg ctcaccgcag 420
gccgacgttg cgcaagccct cgacacgctg gaaagcaaat tagtcgactt ctcggcgtta 480
accgccggtc ttgatatgtc gcgcttccat ctgatggatt ttggcacccg tcgccgtttt 540
tctcgcgaag tacaagaaac catcgttaag cgtctgcaac aggaatcctg gtttgtgggc 600
accagcaact acgatctggc gcgtcggctt tccctcacgc cgatgggaac acaggcacac 660
gaatggttcc aggcacatca gcaaatcagc ccggatctag ccaacagcca gcgagctgca 720
cttgctgcct ggctggaaga gtatcccgac caacttggca ttgcattaac cgactgcatc 780
actatggatg ctttcctgcg tgatttcggt gtcgagttcg ctagtcggta tcagggcctg 840
cgtcatgact ctggcgaccc ggttgaatgg ggtgaaaaag ccattgcaca ttatgaaaag 900
ctgggaattg atccacagag taaaacgctg gttttctctg acaatctgga tttacgcaaa 960
gcggttgagc tataccgcca cttctcttcc cgcgtgcaat taagttttgg tattgggact 1020
cgcctgacct gcgatatccc ccaggtaaaa cccctgaata ttgtcattaa gttggtagag 1080
tgtaacggta aaccggtggc gaaactttct gacagccctg gcaaaactat ctgccatgat 1140
aaagcgtttg ttcgggcgct gcgcaaagcg ttcgaccttc cgcatattaa aaaagccagt 1200
taa 1203

<210> SEQ ID NO 63
<211> LENGTH: 39
<212> TYPE: DNA
<213> ORGANISM: Artificial Sequence
<220> FEATURE:
<223> OTHER INFORMATION: Primer pncB(Eco)-F

<400> SEQUENCE: 63
aaggaaacac tgatatcatg acacaattcg cttctcctg 39

<210> SEQ ID NO 64
<211> LENGTH: 44
<212> TYPE: DNA
<213> ORGANISM: Artificial Sequence
<220> FEATURE:
<223> OTHER INFORMATION: Primer pncB(Eco)-F

<400> SEQUENCE: 64
gccaaaacag cctcgagtta actggctttt ttaatatgcg gaag 44

<210> SEQ ID NO 65
<211> LENGTH: 446
<212> TYPE: PRT
<213> ORGANISM: Corynebacterium glutamicum

<400> SEQUENCE: 65

```
Val Asn Thr Asn Pro Ser Glu Phe Ser Ser Asn Arg Ser Thr Ala Leu
1               5                   10                  15

Leu Thr Asp Lys Tyr Glu Leu Thr Met Leu Gln Ala Ala Leu Ala Asp
            20                  25                  30

Gly Ser Ala Glu Arg Pro Ser Thr Phe Glu Val Phe Ser Arg Arg Leu
        35                  40                  45

Pro Asn Glu Arg Arg Tyr Gly Val Val Ala Gly Thr Ala Arg Val Leu
    50                  55                  60

Lys Ala Ile Arg Asp Phe Val Phe Thr Glu Glu Gln Leu Ala Asp Leu
65                  70                  75                  80

Asp Phe Leu Asp Asp Arg Thr Leu Glu Tyr Leu Arg Asn Tyr Arg Phe
                85                  90                  95

Thr Gly Gln Val Asp Gly Tyr Arg Glu Gly Glu Ile Tyr Phe Pro Gln
            100                 105                 110

Ser Pro Leu Leu Thr Val Arg Gly Thr Phe Ala Glu Cys Val Ile Leu
        115                 120                 125

Glu Thr Val Ile Leu Ser Ile Met Asn Ala Asp Ser Ala Val Ala Ser
    130                 135                 140

Ala Ala Ala Arg Met Val Thr Ala Ala Asp Gly Arg Pro Ile Ile Glu
145                 150                 155                 160

Met Gly Ser Arg Arg Thr His Glu Tyr Ser Ala Val Thr Ala Ser Arg
                165                 170                 175

Ala Ala Tyr Leu Ala Gly Phe Ser Thr Thr Ser Asn Leu Glu Ala Ala
            180                 185                 190

Tyr Arg Tyr Gly Ile Pro Ala Ser Gly Thr Ser Ala His Ala Trp Thr
        195                 200                 205

Leu Leu His Ile Asn Asp Asp Gly Thr Pro Asn Glu Ala Ala Ala Phe
    210                 215                 220

Lys Ala Gln Val Glu Ser Leu Gly Val Asp Thr Thr Leu Leu Val Asp
225                 230                 235                 240

Thr Tyr Asp Ile Thr Gln Gly Val Ala Thr Ala Ile Glu Val Ala Gly
                245                 250                 255

Pro Asp Leu Gly Gly Val Arg Ile Asp Ser Gly Asp Leu Gly Val Leu
            260                 265                 270

Ala Arg Lys Val Arg Lys Gln Leu Asp Asp Leu Asn Ala His Asn Thr
        275                 280                 285

Lys Ile Val Val Ser Ser Asp Leu Asp Glu Phe Ala Ile Ala Gly Leu
    290                 295                 300

Arg Gly Glu Pro Val Asp Val Phe Gly Val Gly Thr Ser Val Val Thr
305                 310                 315                 320

Gly Ser Gly Ala Pro Thr Ala Gly Leu Val Tyr Lys Ile Val Glu Val
                325                 330                 335

Ala Gly His Pro Val Ala Lys Arg Ser Arg Asn Lys Glu Ser Tyr Gly
            340                 345                 350

Gly Gly Lys Lys Ala Val Arg Thr His Arg Lys Ser Gly Thr Ala Ile
        355                 360                 365

Glu Glu Ile Val Tyr Pro Phe Asn Ala Glu Ala Pro Asp Thr Gly Lys
    370                 375                 380

Leu Asp Thr Leu Ser Leu Thr Ile Pro Leu Met Arg Asp Gly Glu Ile
385                 390                 395                 400

Val Pro Gly Leu Pro Thr Leu Glu Asp Ser Arg Ala Tyr Leu Ala Lys
                405                 410                 415

Gln Leu Val Ser Leu Pro Trp Glu Gly Leu Ala Leu Ser Arg Asp Glu
```

```
        420                 425                 430

Pro Val Leu His Thr Arg Phe Val Gly Phe Pro Pro Ala Ala
        435                 440                 445


<210> SEQ ID NO 66
<211> LENGTH: 1341
<212> TYPE: DNA
<213> ORGANISM: Corynebacterium glutamicum

<400> SEQUENCE: 66

gtgaatacca atccgtctga attctcctca aaccgttcaa cagctctcct tactgataaa      60

tatgagctga ccatgcttca agcagcgctc gctgatggtt ctgcagaacg cccctcaacg     120

tttgaggtct ttagccgccg cctccccaac gagcgccgat acggtgtcgt cgcaggaaca     180

gcacgagtgc tgaaggcgat tcgtgacttt gtattcacag aggaacaact cgccgatctt     240

gactttttag acgaccgtac cctggaatac ctccgcaact accgattcac cggccaagtt     300

gatggctacc gcgaaggcga aatctacttc ccgcagtccc ctcttctgac tgtgcgtggc     360

acgtttgcag aatgcgtcat cctagaaact gtcattttgt ccatcatgaa tgcagattct     420

gccgtcgctt ccgccgctgc gcgcatggtc accgcagctg atggtcgccc catcatcgaa     480

atgggatcca ggcgcaccca cgaatactcg gcagtcaccg catcccgcgc agcatacctc     540

gctggattct ccaccacctc caacctcgag gcggcctacc gctacggaat tccagcatcc     600

ggaacctccg cccacgcatg gactttgctg cacatcaacg atgacggcac ccccaacgaa     660

gcagcagctt tcaaagcaca ggttgaatcc ctcggcgtgg acaccacctt gctggtagat     720

acttatgaca tcacccaagg tgtggccacc gccattgaag ttgcaggtcc agaccttggt     780

ggcgtacgta tcgactccgg cgacctaggt gtgcttgccc gaaaggtccg caagcagctc     840

gacgatctca acgcccacaa caccaagatt gtggtctcct ccgacctgga tgaattcgcc     900

atcgcgggtc ttcgcggcga accagttgac gtctttggcg ttggcacctc cgttgtcaca     960

ggttctggcg caccaaccgc tggcctcgtg tacaagatcg tggaagttgc cggtcaccct    1020

gtggccaagc gttcccgaaa caaggaaagc tacggtggtg gcaagaaggc tgtgcgcacc    1080

caccgcaagt ccggtaccgc aatcgaagaa atcgtctacc cattcaatgc cgaagcacca    1140

gatactggaa agctcgacac tttgagcctg accatcccat tgatgcgcga cggtgaaatc    1200

gttccaggtt tgcctacttt ggaagattcc cgagcgtatt tggccaagca attggtctct    1260

ttaccatggg aaggccttgc actgtctcgc gatgagcctg ttttgcacac tcgtttcgtg    1320

ggtttcccgc cggccgctta g                                              1341


<210> SEQ ID NO 67
<211> LENGTH: 44
<212> TYPE: DNA
<213> ORGANISM: Artificial Sequence
<220> FEATURE:
<223> OTHER INFORMATION: Primer 1'NCgl2431-F

<400> SEQUENCE: 67

aaggaaacac tgatatcatg aataccaatc cgtctgaatt ctcc                        44


<210> SEQ ID NO 68
<211> LENGTH: 35
<212> TYPE: DNA
<213> ORGANISM: Artificial Sequence
<220> FEATURE:
<223> OTHER INFORMATION: Primer 1'NCgl2431-R
```

```
<400> SEQUENCE: 68

gccaaaacag cctcgagcta agcggccggc gggaa                               35


<210> SEQ ID NO 69
<211> LENGTH: 446
<212> TYPE: PRT
<213> ORGANISM: Corynebacterium glutamicum

<400> SEQUENCE: 69

Val Asn Thr Asn Pro Ser Glu Phe Ser Ser Asn Arg Ser Thr Ala Leu
1               5                   10                  15

Leu Thr Asp Lys Tyr Glu Leu Thr Met Leu Gln Ala Ala Leu Ala Asp
            20                  25                  30

Gly Ser Ala Glu Arg Pro Ser Thr Phe Glu Val Phe Ser Arg Arg Leu
        35                  40                  45

Pro Asn Glu Arg Arg Tyr Gly Val Val Ala Gly Thr Ala Arg Val Leu
    50                  55                  60

Lys Ala Ile Arg Asp Phe Val Phe Thr Glu Glu Gln Leu Ala Asp Leu
65                  70                  75                  80

Asp Phe Leu Asp Asp Arg Thr Leu Glu Tyr Leu Arg Asn Tyr Arg Phe
                85                  90                  95

Thr Gly Gln Val Asp Gly Tyr Arg Glu Gly Glu Ile Tyr Phe Pro Gln
            100                 105                 110

Ser Pro Leu Leu Thr Val Arg Gly Thr Phe Ala Glu Cys Val Ile Leu
        115                 120                 125

Glu Thr Val Ile Leu Ser Ile Met Asn Ala Asp Ser Ala Val Ala Ser
    130                 135                 140

Ala Ala Ala Arg Met Val Thr Ala Ala Asp Gly Arg Pro Ile Ile Glu
145                 150                 155                 160

Met Gly Ser Arg Arg Thr His Glu Tyr Ser Ala Val Thr Ala Ser Arg
                165                 170                 175

Ala Ala Tyr Leu Ala Gly Phe Ser Thr Thr Ser Asn Leu Glu Ala Ala
            180                 185                 190

Tyr Arg Tyr Gly Ile Pro Ala Ser Gly Thr Ser Ala His Ala Trp Thr
        195                 200                 205

Leu Leu His Ile Asn Asp Asp Gly Thr Pro Asn Glu Ala Ala Ala Phe
    210                 215                 220

Lys Ala Gln Val Glu Ser Leu Gly Val Asp Thr Thr Leu Leu Val Asp
225                 230                 235                 240

Thr Tyr Asp Ile Thr Gln Gly Val Ala Thr Ala Ile Glu Val Ala Gly
                245                 250                 255

Pro Asp Leu Gly Gly Val Arg Ile Asp Ser Gly Asp Leu Gly Val Leu
            260                 265                 270

Ala Arg Lys Val Arg Lys Gln Leu Asp Asp Leu Asn Ala His Asn Thr
        275                 280                 285

Lys Ile Val Val Ser Ser Asp Leu Asp Glu Phe Ala Ile Ala Gly Leu
    290                 295                 300

Arg Gly Glu Pro Val Asp Val Phe Gly Val Gly Thr Ser Val Val Thr
305                 310                 315                 320

Gly Ser Gly Ala Pro Thr Ala Gly Leu Val Tyr Lys Ile Val Glu Val
                325                 330                 335

Ala Gly His Pro Val Ala Lys Arg Ser Arg Asn Lys Glu Ser Tyr Gly
            340                 345                 350

Gly Gly Lys Lys Ala Leu Arg Thr His Arg Lys Ser Gly Thr Ala Ile
```

```
        355                 360                 365

Glu Glu Ile Val Tyr Pro Phe Asn Ala Glu Ala Pro Asp Thr Gly Lys
    370                 375                 380

Leu Asp Thr Leu Ser Leu Thr Ile Pro Leu Met Arg Asp Gly Glu Ile
385                 390                 395                 400

Val Pro Gly Leu Pro Thr Leu Glu Asp Ser Arg Ala Tyr Leu Ala Lys
                405                 410                 415

Gln Leu Val Ser Leu Pro Trp Glu Gly Leu Ala Leu Ser Arg Asp Glu
            420                 425                 430

Pro Val Leu His Thr Arg Phe Val Gly Phe Pro Pro Val Ala
        435                 440                 445
```

<210> SEQ ID NO 70
<211> LENGTH: 1341
<212> TYPE: DNA
<213> ORGANISM: Corynebacterium glutamicum

<400> SEQUENCE: 70

```
gtgaatacca atccttctga attctcctca aaccgttcga cagctctcct tactgataaa      60

tatgagctga ccatgcttca agcagcgctc gctgatggtt cagcagagcg cccctcaacg     120

tttgaggtct ttagccgccg cctccccaac gagcgccgat acggtgtcgt tgcaggaacc     180

gcccgagtgt tgaaggcgat ccgtgacttt gtattcacag aggaacaact cgccgacctc     240

gacttcttag acgaccgcac cctggaatac ctccgcaact accgattcac cggccaagtt     300

gatggatacc gcgaaggcga aatctacttc ccgcagtccc ctcttctgac tgtgcgtggc     360

acgtttgcag aatgcgtcat cctagaaacc gtcattttgt ccatcatgaa tgcggattcc     420

gccgttgcct ctgccgcagc gcgcatggtt accgcagctg atggccgccc catcattgaa     480

atgggctcca ggcgcaccca cgaatactct gcagtcactg catcccgcgc cgcctacctc     540

gcgggattct ccaccacctc caacctcgag gcggcctacc gctacggaat tccagcatcc     600

ggaacctccg cccacgcatg gactttgcta cacatcaacg atgacggcac ccccaacgaa     660

gcagcagctt tcaaagcaca ggttgaatcc ctcggcgtgg acaccacctt gctggtagat     720

acttatgaca tcacccaagg tgtggccacc gccatcgaag ttgcaggccc agaccttggt     780

ggcgtgcgca tcgattccgg cgacctgggt gtgcttgccc gcaaggtccg caagcagctc     840

gacgatctca acgcccacaa caccaagatt gtggtctcct ccgacctgga tgaattcgcc     900

atcgcgggtc ttcgcggcga accagttgac gtctttggcg ttggcacctc cgttgtcaca     960

ggttctggcg caccaaccgc tggcctcgtg tacaagatcg tggaagttgc cggtcaccct    1020

gtggccaagc gttcccgaaa caaggaaagc tacggcggcg gcaagaaggc tctgcgcacc    1080

caccgcaagt ccggtaccgc aatcgaagaa atcgtctacc cattcaacgc ggaagcacca    1140

gatactggaa agctcgacac tttgagcctg accatcccat tgatgcgtga cggtgaaatc    1200

gttccaggtt tgcctacttt ggaagattcc cgagcgtatt tggccaagca attggtctct    1260

ttgccatggg aaggccttgc actttctcgt gatgagcctg tgctgcacac tcgtttcgta    1320

ggattcccgc cggtcgctta g                                              1341
```

<210> SEQ ID NO 71
<211> LENGTH: 44
<212> TYPE: DNA
<213> ORGANISM: Artificial Sequence
<220> FEATURE:
<223> OTHER INFORMATION: Primer 2'NCgl2431-F

<400> SEQUENCE: 71

```
aaggaaacac tgatatcatg aataccaatc cttctgaatt ctcc                44
```

<210> SEQ ID NO 72
<211> LENGTH: 37
<212> TYPE: DNA
<213> ORGANISM: Artificial Sequence
<220> FEATURE:
<223> OTHER INFORMATION: Primer 2'NCgl2431-R

<400> SEQUENCE: 72

```
gccaaaacag cctcgagcta agcgaccggc gggaatc                         37
```

<210> SEQ ID NO 73
<211> LENGTH: 238
<212> TYPE: PRT
<213> ORGANISM: Corynebacterium glutamicum

<400> SEQUENCE: 73

```
Met Arg Ile Leu Pro Ile Gly Pro His Asp Glu Ile Ala Val Asn Gly
1               5                   10                  15

Ser Ile Val Leu Leu Ser Glu His Asp Gly Asp Ile Val Ser Val Gly
            20                  25                  30

Pro Asp Leu Gly Thr Val Arg Val Thr Leu Glu Glu Ile Glu Ser Leu
        35                  40                  45

Gly Thr Pro Thr Ala Pro Arg Asp Leu Gly Ser Arg Glu Val Asp Ala
    50                  55                  60

Cys Val Ser Leu Leu Arg Asn Arg Glu Leu Val Arg Phe Asp Pro His
65                  70                  75                  80

Asp Gly Ser Glu Leu Thr Tyr Arg Glu His Ser Val Ala Tyr Gly Ala
                85                  90                  95

Ser Gly Lys Pro Leu Phe Pro Arg Leu Asp Pro Ala Val Ile Gly Ile
            100                 105                 110

Val Glu Leu Arg Gly Glu Asp Arg Leu Leu Leu Gly Met Asn Ala Gln
        115                 120                 125

Lys Arg Gln Arg Tyr Ser Leu Ile Ala Gly Tyr Val Ser His Gly Glu
    130                 135                 140

Ser Leu Glu Asp Ala Phe Thr Arg Glu Val Phe Glu Glu Ala Ala Arg
145                 150                 155                 160

Arg Val Ser Glu Ile Ser Tyr Val Ser Ser Gln Pro Trp Pro Ile Ser
                165                 170                 175

Gly Ser Leu Met Leu Gly Met Lys Gly Phe Thr Glu Asp Glu Leu Pro
            180                 185                 190

Gln Gly Glu Thr Asp Gly Glu Leu Ala Glu Thr Ile Trp Ala Ser Pro
        195                 200                 205

Leu Asp Ile Ile Asp Arg Lys Ile Pro Ile Ala Pro Pro Gly Ser Ile
    210                 215                 220

Ala Tyr Asp Met Ile Asn Ala Trp Ala Arg Asp Lys Gln Asn
225                 230                 235
```

<210> SEQ ID NO 74
<211> LENGTH: 717
<212> TYPE: DNA
<213> ORGANISM: Corynebacterium glutamicum

<400> SEQUENCE: 74

```
atgagaattc ttcccatcgg cccccacgat gaaatcgccg tcaacggatc aatagtcctt      60
```

```
ctatccgagc acgacggaga catcgtatcg gtcggccccg acctcggcac ggtgcgagtt    120

acccttgaag agatcgaaag tttaggtaca ccgacggcac cccgcgatct gggttctcgg    180

gaagtcgacg catgcgtatc gttgctccgc aaccgcgagt tagtgcgatt cgatccccac    240

gatggcagtg aattaaccta tcgggaacat agcgttgctt acggtgcgag tggcaagcca    300

ttgtttcccc gattggatcc agcggtgatc ggcattgtgg agctgcgagg tgaggatcgt    360

ttgcttctgg gcatgaatgc gcagaaacgc caacgctatt cattaatcgc aggttatgtt    420

tcgcatggtg agtcgctgga agacgcattc accagagaag tgttcgagga agcggcgcgc    480

cgggtatctg agatttccta tgtgtcgtct caaccatggc cgatctctgg ttcgctgatg    540

ctgggtatga agggcttcac ggaagatgag ttgcctcaag gcgaaactga tggtgaatta    600

gcggagacaa tctgggcttc gccactagac attatcgatc gtaagattcc gatcgcccca    660

cccggatcga ttgcctacga catgatcaac gcctgggcgc gagataaaca aaactaa       717
```

<210> SEQ ID NO 75
<211> LENGTH: 36
<212> TYPE: DNA
<213> ORGANISM: Artificial Sequence
<220> FEATURE:
<223> OTHER INFORMATION: Primer 0744-del-5F

<400> SEQUENCE: 75

```
ccggggatcc tctagagcag atgtgttgcg tctagc                               36
```

<210> SEQ ID NO 76
<211> LENGTH: 26
<212> TYPE: DNA
<213> ORGANISM: Artificial Sequence
<220> FEATURE:
<223> OTHER INFORMATION: Primer 0744-del-5R

<400> SEQUENCE: 76

```
ttgtcattta cctcctcgct aaatac                                          26
```

<210> SEQ ID NO 77
<211> LENGTH: 39
<212> TYPE: DNA
<213> ORGANISM: Artificial Sequence
<220> FEATURE:
<223> OTHER INFORMATION: Primer 0744-del-3F

<400> SEQUENCE: 77

```
cgaggaggta aatgacaagg aagatgagtt gcctcaagg                            39
```

<210> SEQ ID NO 78
<211> LENGTH: 36
<212> TYPE: DNA
<213> ORGANISM: Artificial Sequence
<220> FEATURE:
<223> OTHER INFORMATION: Primer 0744-del-3R

<400> SEQUENCE: 78

```
gcaggtcgac tctagacaga ttacccgcca cctgag                               36
```

<210> SEQ ID NO 79
<211> LENGTH: 238
<212> TYPE: PRT
<213> ORGANISM: Corynebacterium glutamicum

<400> SEQUENCE: 79

```
Met Arg Ile Leu Pro Ile Gly Pro His Asp Glu Ile Ala Val Asn Gly
```

```
1               5                   10                  15

Ser Ile Val Leu Leu Ser Glu His Asp Gly Asp Ile Val Ser Val Gly
            20                  25                  30

Pro Asp Leu Gly Thr Val Arg Val Thr Leu Glu Glu Ile Glu Ser Leu
        35                  40                  45

Gly Thr Pro Thr Ala Pro Arg Asp Leu Gly Ser Arg Glu Val Asp Ala
    50                  55                  60

Cys Val Ser Leu Leu Arg Asn Arg Glu Leu Val Arg Phe Asp Pro His
65                  70                  75                  80

Asp Gly Ser Glu Leu Thr Tyr Arg Glu His Ser Val Ala Tyr Gly Ala
                85                  90                  95

Ser Gly Lys Pro Leu Phe Pro Arg Leu Asp Pro Ala Val Ile Gly Ile
            100                 105                 110

Val Glu Leu Arg Gly Glu Asp Arg Leu Leu Leu Gly Met Asn Ala Gln
        115                 120                 125

Lys Arg Gln Arg Tyr Ser Leu Ile Ala Gly Tyr Val Ser His Gly Glu
    130                 135                 140

Ser Leu Glu Asp Ala Phe Thr Arg Glu Val Phe Glu Glu Ala Ala Arg
145                 150                 155                 160

Arg Val Ser Glu Ile Ser Tyr Val Ser Ser Gln Pro Trp Pro Ile Ser
                165                 170                 175

Gly Ser Leu Met Leu Gly Met Lys Gly Phe Thr Glu Asp Glu Leu Pro
            180                 185                 190

Gln Gly Val Thr Asp Gly Glu Leu Ala Glu Thr Ile Trp Ala Ser Pro
        195                 200                 205

Leu Asp Ile Ile Asp Arg Lys Ile Pro Ile Ala Pro Pro Gly Ser Ile
    210                 215                 220

Ala Tyr Asp Met Ile Asn Ala Trp Ala Arg Asp Lys Gln Asn
225                 230                 235
```

<210> SEQ ID NO 80
<211> LENGTH: 717
<212> TYPE: DNA
<213> ORGANISM: Corynebacterium glutamicum

<400> SEQUENCE: 80

```
atgagaattc ttcccattgg cccccacgat gaaatcgccg tcaacggatc aatagtcctt     60

ctatccgagc acgatggaga catcgtatcg gtcggccccg acctcggcac ggtgcgcgtt    120

acccttgaag agatcgaaag tttaggtaca ccgacggcac ctcgcgatct gggttctcgg    180

gaagtcgacg catgcgtatc gttgctccgc aaccgcgagt tagtgcgatt cgatccccac    240

gatggcagtg aattaaccta tcgggaacat agcgttgctt acggtgcgag tggcaagcca    300

ttgtttcccc gattggatcc agcggtgatc ggcattgtgg agctgcgagg tgaggatcgt    360

ttgcttctgg gcatgaatgc gcagaaacgc caacgctatt cattaatcgc aggttatgtt    420

tcgcatggtg agtcgctgga agacgcattc accagagaag tgttcgagga agcggcgcgc    480

cgggtatctg agatttccta tgtgtcgtct caaccatggc cgatctctgg ttcgctgatg    540

ctgggtatga agggcttcac ggaagatgag ttgcctcaag gcgtaactga tggtgaatta    600

gcggagacaa tctgggcttc gccactagac attatcgatc gtaagattcc gatcgcccca    660

cccggatcga ttgcctacga catgatcaac gcctgggcgc gagataaaca aaactaa       717
```

<210> SEQ ID NO 81
<211> LENGTH: 320

<212> TYPE: PRT
<213> ORGANISM: Corynebacterium glutamicum

<400> SEQUENCE: 81

Met Thr Ala Pro Thr Asn Ala Gly Glu Leu Arg Arg Val Leu Leu Val
1               5                   10                  15

Pro His Thr Gly Arg Ser Ser Asn Ile Glu Ser Ala Ile Leu Ala Ala
            20                  25                  30

Lys Leu Leu Asp Asp Ala Gly Ile Asp Val Arg Val Leu Ile Asn Asp
        35                  40                  45

Ala Asp Asp Pro Ile Ala Glu His Ser Val Leu Gly Arg Phe Thr His
    50                  55                  60

Val Arg His Ala Ala Asp Ala Ala Asp Gly Ala Glu Leu Val Leu Val
65                  70                  75                  80

Leu Gly Gly Asp Gly Thr Phe Leu Arg Ala Ala Asp Met Ala His Ala
                85                  90                  95

Val Asp Leu Pro Val Leu Gly Ile Asn Leu Gly His Val Gly Phe Leu
            100                 105                 110

Ala Glu Trp Glu Ser Asp Ser Leu Glu Glu Ala Leu Lys Arg Val Ile
        115                 120                 125

Asp Arg Asp Tyr Arg Ile Glu Asp Arg Met Thr Leu Thr Val Val Val
    130                 135                 140

Leu Asp Gly Gly Gly Glu Glu Ile Gly Arg Gly Trp Ala Leu Asn Glu
145                 150                 155                 160

Val Ser Ile Glu Asn Leu Asn Arg Arg Gly Val Leu Asp Ala Thr Leu
                165                 170                 175

Glu Val Asp Ala Arg Pro Val Ala Ser Phe Gly Cys Asp Gly Val Leu
            180                 185                 190

Ile Ser Thr Pro Thr Gly Ser Thr Ala Tyr Ala Phe Ser Ala Gly Gly
        195                 200                 205

Pro Val Leu Trp Pro Glu Leu Asp Ala Ile Leu Val Val Pro Asn Asn
    210                 215                 220

Ala His Ala Leu Phe Thr Lys Pro Leu Val Val Ser Pro Lys Ser Thr
225                 230                 235                 240

Val Ala Val Glu Ser Asn Ser Asp Thr Ser Ala Ala Met Ala Val Met
                245                 250                 255

Asp Gly Phe Arg Pro Ile Pro Met Pro Pro Gly Ser Arg Val Glu Val
            260                 265                 270

Thr Arg Gly Glu Arg Pro Val Arg Trp Val Arg Leu Asp Ser Ser Pro
        275                 280                 285

Phe Thr Asp Arg Leu Val Ser Lys Leu Arg Leu Pro Val Thr Gly Trp
    290                 295                 300

Arg Gly Pro Gln Lys Gln Ala Glu Asn Lys Asp Pro Arg Ser Ala Gly
305                 310                 315                 320

<210> SEQ ID NO 82
<211> LENGTH: 963
<212> TYPE: DNA
<213> ORGANISM: Corynebacterium glutamicum

<400> SEQUENCE: 82
atgactgcac ccacgaacgc tggggaactc aggcgagttt tgctggttcc acacaccggg 60
cgttcttcca atattgaatc cgccatcttg gcagccaagc tgctcgacga tgctggaatc 120
gatgtgaggg tgctgatcaa tgatgcagat gatccaattg cagagcactc cgttttaggc 180

```
cgtttcaccc atgtcaggca cgctgcagac gccgctgacg gcgcagaact agttctggtg    240

ctgggtggag atggcacctt cctccgcgca gcagatatgg cccacgctgt tgatttgcct    300

gttctgggca tcaacctagg ccatgtggga ttcttggctg aatgggagtc tgactcactt    360

gaagaggcac tcaaacgtgt gatcgaccgc gattaccgta ttgaagatcg catgacctta    420

actgtcgttg tcctagacgg cggtggagaa gaaatcggcc gaggctgggc tctcaatgag    480

gtcagtattg aaaacttaaa ccgcagggga gtgctcgatg caaccctcga ggtagatgca    540

cgaccagttg cttcctttgg ttgcgatggc gtgctgattt ccaccccaac cggctccacc    600

gcttatgcat tttccgccgg tggtcctgta ctgtggccag aactcgatgc catcttggtg    660

gttcctaata acgcccacgc gctgtttacc aaaccgctgg ttgtgagccc aaaatccacc    720

gtagctgtgg aatccaattc agatacttca gcagcgatgg ccgtcatgga tggtttccgt    780

cccattccta tgcctccagg atcccgtgtt gaggtcacca ggggtgagcg tcccgtgcgt    840

tgggtgaggc ttgattcttc accgtttacc gaccgacttg tgagcaaatt aaggctcccc    900

gttaccggtt ggcggggtcc gcaaaaacag gcggaaaata aagatcccag gtcagcgggg    960

taa                                                                  963
```

<210> SEQ ID NO 83
<211> LENGTH: 37
<212> TYPE: DNA
<213> ORGANISM: Artificial Sequence
<220> FEATURE:
<223> OTHER INFORMATION: Primer NCgl1358-F

<400> SEQUENCE: 83

```
aaggaaacac tgatatcatg actgcaccca cgaacgc                              37
```

<210> SEQ ID NO 84
<211> LENGTH: 35
<212> TYPE: DNA
<213> ORGANISM: Artificial Sequence
<220> FEATURE:
<223> OTHER INFORMATION: Primer NCgl1358-R

<400> SEQUENCE: 84

```
gccaaaacag cctcgagtta ccccgctgac ctggg                                35
```

<210> SEQ ID NO 85
<211> LENGTH: 319
<212> TYPE: PRT
<213> ORGANISM: Corynebacterium glutamicum

<400> SEQUENCE: 85

```
Met Thr Ala Pro Thr Asn Ala Gly Glu Leu Arg Arg Val Leu Leu Val
1               5                   10                  15

Pro His Thr Gly Arg Ser Ser Asn Ile Glu Ser Ala Ile Leu Ala Ala
            20                  25                  30

Lys Leu Leu Asp Asp Ala Gly Ile Asp Val Arg Val Leu Ile Asn Asp
        35                  40                  45

Ala Asp Asp Pro Ile Ala Glu His Pro Val Leu Gly Arg Phe Thr His
    50                  55                  60

Val Arg His Ala Ala Asp Ala Ala Asp Gly Ala Glu Leu Val Leu Val
65                  70                  75                  80

Leu Gly Gly Asp Gly Thr Phe Leu Arg Ala Ala Asp Met Ala His Ala
                85                  90                  95

Val Asp Leu Pro Val Leu Gly Ile Asn Leu Gly His Val Gly Phe Leu
```

```
            100                 105                 110

Ala Glu Trp Glu Ser Asp Ser Leu Glu Glu Ala Leu Lys Arg Val Ile
        115                 120                 125

Asp Arg Asp Tyr Arg Ile Glu Asp Arg Met Thr Leu Thr Val Val Val
    130                 135                 140

Leu Asp Gly Gly Gly Glu Glu Ile Gly Arg Gly Trp Ala Leu Asn Glu
145                 150                 155                 160

Val Ser Ile Glu Asn Leu Asn Arg Arg Gly Val Leu Asp Ala Thr Leu
                165                 170                 175

Glu Val Asp Ala Arg Pro Val Ala Ser Phe Gly Cys Asp Gly Val Leu
            180                 185                 190

Ile Ser Thr Pro Thr Gly Ser Thr Ala Tyr Ala Phe Ser Ala Gly Gly
        195                 200                 205

Pro Val Leu Trp Pro Glu Leu Asp Ala Ile Leu Val Val Pro Asn Asn
    210                 215                 220

Ala His Ala Leu Phe Thr Lys Pro Leu Val Val Ser Pro Lys Ser Thr
225                 230                 235                 240

Val Ala Val Glu Ser Asn Ser Asp Thr Ser Ala Ala Met Ala Val Met
                245                 250                 255

Asp Gly Phe Arg Pro Ile Pro Met Pro Pro Gly Ser Arg Val Glu Val
            260                 265                 270

Thr Arg Gly Glu Arg Pro Val Arg Trp Val Arg Leu Asp Ser Ser Pro
        275                 280                 285

Phe Thr Asp Arg Leu Val Ser Lys Leu Arg Leu Pro Val Thr Gly Trp
    290                 295                 300

Arg Gly Pro Gln Lys Gln Ala Glu Asn Lys Asp Pro Arg Ser Ala
305                 310                 315
```

<210> SEQ ID NO 86
<211> LENGTH: 963
<212> TYPE: DNA
<213> ORGANISM: Corynebacterium glutamicum

<400> SEQUENCE: 86

```
atgactgcac ccacgaacgc tggggaactc aggcgagttt tgctggttcc acacaccggg      60

cgttcttcca atattgaatc cgccatcttg gcagccaagc tgctcgacga tgctggaatc     120

gatgtgaggg tgctgatcaa tgatgcagat gatccaattg cagagcaccc cgttttaggc     180

cgtttcaccc atgtcaggca cgctgccgac gctgctgacg gcgcagaact agttctggtg     240

ctgggtggag atggcacctt cctccgcgca gcagatatgg cccacgctgt tgatttgcct     300

gttctgggca tcaacctagg ccatgtggga ttcttggctg aatgggagtc tgactcactt     360

gaagaggcac tcaaacgtgt gatcgaccgc gattaccgta ttgaagatcg catgacctta     420

actgtcgttg tcctagacgg cggtggagaa gaaatcggcc gaggctgggc tctcaatgag     480

gtcagtattg aaaacttaaa ccgcaggggga gtgctcgatg caaccctcga ggtagatgca     540

cgaccagttg cttcctttgg ttgcgatggc gtgctgattt ccaccccaac cggctccacc     600

gcttatgcat tttccgccgg tggtcctgta ctgtggccag aactcgatgc catcttggtg     660

gttcctaata acgcccacgc gctgtttacc aaaccgctgg ttgtgagccc aaaatccacc     720

gtagctgtgg aatccaattc agatacttca gcagcgatgg ccgtcatgga tggtttccgt     780

cccattccta tgcctccagg atcccgtgtt gaggtcacca ggggtgagcg tcccgtgcgt     840

tgggtgaggc ttgattcttc accgtttacc gaccgacttg tgagcaaatt aaggctcccc     900
```

```
gttaccggtt ggcggggtcc gcaaaaacag gcggaaaata aagatcccag gtcagcgggg    960

taa                                                                  963


<210> SEQ ID NO 87
<211> LENGTH: 494
<212> TYPE: PRT
<213> ORGANISM: Corynebacterium glutamicum

<400> SEQUENCE: 87

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
            340                 345                 350

Leu Cys Ile Trp Gly Ala Thr His Thr Asp Gly Leu Pro Phe Phe Ile
```

```
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
    450                 455                 460

Leu Ile Ile Ala Leu Val Cys Ala Val Ala Ala Ala Leu Ile Ser Ser
465                 470                 475                 480

Tyr Leu Phe Arg Gly Asn Pro Lys Gly Ala Asn Asn Ala His
                485                 490


<210> SEQ ID NO 88
<211> LENGTH: 177
<212> TYPE: PRT
<213> ORGANISM: Corynebacterium glutamicum

<400> SEQUENCE: 88

Met Arg Thr Ser Lys Lys Glu Met Ile Leu Arg Thr Ala Ile Asp Tyr
1               5                   10                  15

Ile Gly Glu Tyr Ser Leu Glu Thr Leu Ser Tyr Asp Ser Leu Ala Glu
            20                  25                  30

Ala Thr Gly Leu Ser Lys Ser Gly Leu Ile Tyr His Phe Pro Ser Arg
        35                  40                  45

His Ala Leu Leu Leu Gly Met His Glu Leu Leu Ala Asp Asp Trp Asp
    50                  55                  60

Lys Glu Leu Arg Asp Ile Thr Arg Asp Pro Glu Asp Pro Leu Glu Arg
65                  70                  75                  80

Leu Arg Ala Val Val Val Thr Leu Ala Glu Asn Val Ser Arg Pro Glu
                85                  90                  95

Leu Leu Leu Leu Ile Asp Ala Pro Ser His Pro Asp Phe Leu Asn Ala
            100                 105                 110

Trp Arg Thr Val Asn His Gln Trp Ile Pro Asp Thr Asp Asp Leu Glu
        115                 120                 125

Asn Asp Ala His Lys Arg Ala Val Tyr Leu Val Gln Leu Ala Ala Asp
    130                 135                 140

Gly Leu Phe Val His Asp Tyr Ile His Asp Asp Val Leu Ser Lys Ser
145                 150                 155                 160

Lys Arg Gln Ala Met Leu Glu Thr Ile Leu Glu Leu Ile Pro Ser Gln
                165                 170                 175

Thr
```

PUTRESCINE-PRODUCING MICROORGANISM AND METHOD OF PRODUCING PUTRESCINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_463USPC_SEQUENCE_LISTING.txt. The text file is 112 KB, was created on Jan. 15, 2020, and is being submitted electronically via EFS-Web.

TECHNICAL FIELD

The present disclosure relates to a putrescine-producing microorganism and a method of producing putrescine using the corresponding microorganism.

BACKGROUND ART

Coryneform microorganisms are Gram-positive microorganisms that are frequently used in industrial production of substances with various applications, such as feeds, pharmaceuticals, and foods including L-amino acids and various nucleic acids. In recent years, diamine and keto-acid are produced from coryneform microorganisms.

In order to produce useful products through microbial fermentation, a demand for an energy source or a reducing power is increased, along with strengthening the biosynthetic pathway of a target product in microorganisms. Among them, NADPH (nicotinamide adenine dinucleotide phosphate) is an essential element in providing a reducing power. The oxidized form $NADP^+$ and the reduced form NADPH are in vivo electron transfer materials and are involved in various synthesis processes. Among the central metabolic pathways, NADPH is known to be mainly produced by 1) the oxidative pentose phosphate pathway and 2) the NADP-dependent isocitrate dehydrogenase (Icd gene) of the TCA pathway. In addition, various microorganisms have malate enzyme, glucose dehydrogenase, and non-phosphorylating glyceraldehyde-3-phosphate dehydrogenase in various alternative pathways to supply NADPH.

Further, regardless of the central metabolic pathway, NADPH-producing enzymes include transhydrogenase, Ferredoxin:$NADP^+$ oxidoreductase, etc.

Meanwhile, putrescine is known as one of the raw materials of polyamide. Putrescine has been mainly produced by chemical methods of using petroleum compounds as raw materials, and technologies for producing putrescine by fermentation using genetic engineering technology and fermentation technology are currently being studied. For example, a method of producing a high concentration of putrescine by transforming *E. coli* and a microorganism of the genus *Corynebacterium* is disclosed (Morris et al., J Biol. Chem. 241: 13, 3129-3135, 1966, International Publication No. WO06/005603; International Publication No. WO09/125924; Qian Z D et al., Biotechnol. Bioeng. 104: 4, 651-662, 2009; Schneider et al., Appl. Microbiol. Biotechnol. 88: 4, 859-868, 2010; Schneider et al., Appl. Microbiol. Biotechnol. 91: 17-30, 2011).

However, there have been no reports on the relationship between a reducing power and a putrescine production capacity.

DISCLOSURE

Technical Problem

The present inventors have made intensive efforts to increase putrescine production in a putrescine-producing microorganism, and as a result, through various studies for enhancing NADPH for the production of a high concentration of putrescine, they have confirmed that putrescine production is increased in a microorganism of the genus *Corynebacterium*, thereby completing the present disclosure.

Technical Solution

An object of the present disclosure is to provide a putrescine-producing microorganism of the genus *Corynebacterium*, in which NADPH (reduced nicotinamide adenine dinucleotide phosphate) productivity is increased, as compared with a non-modified microorganism.

Another object of the present disclosure is to provide a method of producing putrescine using the microorganism.

Advantageous Effects

The present disclosure relates to a putrescine-producing microorganism and a method of producing putrescine using the corresponding microorganism, and the present disclosure has an excellent effect of increasing putrescine production in a microorganism of the genus *Corynebacterium.*

BEST MODE

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

To achieve the above objects, one aspect of the present disclosure is to provide a putrescine-producing microorganism of the genus *Corynebacterium*, in which NADPH (reduced nicotinamide adenine dinucleotide phosphate) productivity is increased, as compared with a non-modified microorganism.

As used herein, the term "NADPH (reduced nicotinamide adenine dinucleotide phosphate)" is a kind of coenzyme participating in reactions of a lot of oxidoreductase and dehydrogenase as an electron donor to provide a reducing power, together with NADH sharing a nicotinamide adenine dinucleotide structure. Oxides ($NAD^+$ and $NADP^+$) of these coenzymes are known to perform an important function of receiving energy generated in biological catabolism in the form of electron and proton, and to participate in the reaction of oxidoreductase as an electron acceptor.

Specifically, to increase NADPH productivity, the putrescine-producing microorganism of the genus *Corynebacterium* may have (1) enhancement of activities of one or more from the group consisting of NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, and $NAD^+$ kinase, (2) inactivation of activities of one or more from the group consisting of gluconate kinase and $NAD^+$ diphosphatase, or (3) a combination of (1) and (2), but is not limited thereto.

Further, the (1) enhancement of activities of one or more from the group consisting of NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, and $NAD^+$ kinase may be enhancement of activities of one or more thereof, two or more thereof, three or more thereof, four or more thereof, five or more thereof, or all of the enzymes.

Further, (2) one or all from the group consisting of gluconate kinase and $NAD^+$ diphosphatase may be inactivated.

Further, in (3), the combination of (1) and (2) may be a combination of enhancement of activities of one or more, two or more, three or more, four or more, five or more, or all enzymes from the group consisting of NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, and $NAD^+$ kinase, and inactivation of activity or activities of any one or all from the group consisting of gluconate kinase and $NAD^+$ diphosphatase.

As used herein, the term "NADP-dependent glyceraldehyde-3-phosphate dehydrogenase" collectively refers to an enzyme that synthesizes one molecule of NADPH by converting D-glyceraldehyde-3-phosphate into 3-phospho-D-glycerate.

Specifically, the NADP-dependent glyceraldehyde-3-phosphate dehydrogenase may be a protein including an amino acid sequence represented by SEQ ID NO: 1 or SEQ ID NO: 7, but is not limited thereto, and may be used interchangeably with a protein having the amino acid sequence represented by SEQ ID NO: 1 or SEQ ID NO: 7, or a protein composed of the amino acid sequence represented by SEQ ID NO: 1 or SEQ ID NO: 7.

As used herein, the term "transketolase" is an enzyme that affects the pentose phosphate pathway, and produces D-sedoheptulose-7-phosphate and D-glyceraldehyde-3-phosphate from D-xylulose-5-phosphate and D-ribose-5-phosphate.

Specifically, the transketolase may be a protein including an amino acid sequence represented by SEQ ID NO: 10 or SEQ ID NO: 16, but is not limited thereto, and may be used interchangeably with a protein having the amino acid sequence represented by SEQ ID NO: 10 or SEQ ID NO: 16, or a protein composed of the amino acid sequence represented by SEQ ID NO: 10 or SEQ ID NO: 16.

As used herein, the term "glucose-6-phosphate dehydrogenase" collectively refers to an enzyme that synthesizes one molecule of NADPH by converting β-D-glucose 6-phosphate into 6-phospho D-glucono-1,5-lactone. The glucose-6-phosphate dehydrogenase is also called a different name, G6PD, G6PDH, etc. Further, in the present disclosure, the glucose-6-phosphate dehydrogenase may be used interchangeably with G6PD or G6PDH.

Specifically, the glucose-6-phosphate dehydrogenase may be a protein including an amino acid sequence represented by SEQ ID NO: 20 or SEQ ID NO: 27, but is not limited thereto, and may be used interchangeably with a protein having the amino acid sequence represented by SEQ ID NO: 20 or SEQ ID NO: 27, or a protein composed of the amino acid sequence represented by SEQ ID NO: 20 or SEQ ID NO: 27.

As used herein, the term "6-phosphogluconate dehydrogenase" collectively refers to an enzyme that synthesizes one molecule of NADPH by converting D-gluconate 6-phosphate into D-ribulose 5-phosphate. The 6-phosphogluconate dehydrogenase is also called a different name, 6PGD, etc. Further, in the present disclosure, the 6-phosphogluconate dehydrogenase may be used interchangeably with 6PGD.

Specifically, the 6-phosphogluconate dehydrogenase may be a protein including an amino acid sequence represented by SEQ ID NO: 32 or SEQ ID NO: 36, but is not limited thereto, and may be used interchangeably with a protein having the amino acid sequence represented by SEQ ID NO: 32 or SEQ ID NO: 36, or a protein composed of the amino acid sequence represented by SEQ ID NO: 32 or SEQ ID NO: 36.

As used herein, the term "NAD(P) transhydrogenase" collectively refers to an enzyme that synthesizes one molecule of NADPH by transferring hydrogen of NADH to Specifically, the NAD(P) transhydrogenase may be a protein including an amino acid sequence represented by SEQ ID NO: 39 or SEQ ID NO: 41, but is not limited thereto, and may be used interchangeably with a protein having the amino acid sequence represented by SEQ ID NO: 39 or SEQ ID NO: 41, or a protein composed of the amino acid sequence represented by SEQ ID NO: 39 or SEQ ID NO: 41.

As used herein, the term "gluconate kinase" collectively refers to an enzyme that converts 6-phospho-D-gluconate as an intermediate in the pentose phosphorylation pathway into gluconate.

Specifically, the gluconate kinase may be a protein including an amino acid sequence represented by SEQ ID NO: 45, SEQ ID NO: 53, SEQ ID NO: 51, or SEQ ID NO: 59, but is not limited thereto, and may be used interchangeably with a protein having the amino acid sequence represented by SEQ ID NO: 51 or SEQ ID NO: 59, or a protein composed of the amino acid sequence represented by SEQ ID NO: 51 or SEQ ID NO: 59.

As used herein, the term "nicotinate phosphoribosyltransferase" collectively refers to an enzyme that synthesizes β-nicotinate D-ribonucleotide from nicotinate. The β-nicotinate D-ribonucleotide may be converted into $NAD^+$ via Deamino-$NAD^+$, and $NAD^+$ may be converted into $NADP^+$, and thus enhancement of nicotinate phosphoribosyltransferase may increase the amounts of NADPH precursors.

Specifically, the nicotinate phosphoribosyltransferase may be a protein including an amino acid sequence represented by SEQ ID NO: 61, SEQ ID NO: 65, or SEQ ID NO: 69, but is not limited thereto, and may be used interchangeably with a protein having the amino acid sequence represented by SEQ ID NO: 65 or SEQ ID NO: 69, or a protein composed of the amino acid sequence represented by SEQ ID NO: 65 or SEQ ID NO: 69.

As used herein, the term "$NAD^+$ diphosphatase" collectively refers to an enzyme that cleaves $NAD^+$ into β-nicotinamide D-ribonucleotide. Attenuation of the $NAD^+$ diphosphatase may increase the amounts of NAD which is a NADPH precursor.

Specifically, the $NAD^+$ diphosphatase may be a protein including an amino acid sequence represented by SEQ ID NO: 73 or SEQ ID NO: 79, but is not limited thereto, and may be used interchangeably with a protein having the amino acid sequence represented by SEQ ID NO: 73 or SEQ ID NO: 79, or a protein composed of the amino acid sequence represented by SEQ ID NO: 73 or SEQ ID NO: 79.

As used herein, the term "$NAD^+$ kinase" collectively refers to an enzyme that synthesizes $NADP^+$ from $NAD^+$. $NADP^+$ is a precursor of NADPH.

Specifically, the NAD$^+$ kinase may be a protein including an amino acid sequence represented by SEQ ID NO: 81 or SEQ ID NO: 85, but is not limited thereto, and may be used interchangeably with a protein having the amino acid sequence represented by SEQ ID NO: 81 or SEQ ID NO: 85, or a protein composed of the amino acid sequence represented by SEQ ID NO: 81 or SEQ ID NO: 85.

Genetic information of the NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, NAD$^+$ kinase, gluconate kinase, or NAD$^+$ diphosphatase may be obtained from a public database, and example thereof may be GenBank of National Center for Biotechnology Information (NCBI), etc., but is not limited thereto.

With regard to the NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, NAD$^+$ kinase, gluconate kinase, or NAD+ diphosphatase, the amino sequence of the given protein showing the activity may vary depending on the species or strain of the microorganism, and therefore, and thus is not limited to the origin or sequence thereof.

Further, in the present disclosure, each of the above enzymes may include the protein having the amino acid sequence of the above-described SEQ ID NO., or a protein having 80% or more, 85% or more, specifically 90% or more, more specifically 95% or more, and much more specifically 99% or more homology or identity to the amino acid sequence.

Further, as a sequence having homology or identity to the sequence, if the amino acid sequence substantially has biological activities identical or corresponding to those of each enzyme protein of the above-described SEQ ID NO., it is obvious in that the an amino acid sequence with deletion, modification, substitution, or addition in part of the sequences should also be included in the scope of the present disclosure.

A polynucleotide encoding NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, NAD$^+$ kinase, gluconate kinase, or NAD$^+$ diphosphatase of the present disclosure may include a polynucleotide encoding the protein having the amino acid sequence of the above-described SEQ ID NO., or the protein having 80% or more, 85% or more, specifically 90% or more, more specifically 95% or more, much more specifically 99% or more homology or identity to the above sequence, as long as it has biological activity identical or corresponding to that of the enzyme protein of NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, NAD$^+$ kinase, gluconate kinase, or NAD$^+$ diphosphatase. For example, the NADP-dependent glyceraldehyde-3-phosphate dehydrogenase may be encoded by a polynucleotide sequence of SEQ ID NO: 2 or SEQ ID NO: 8, the transketolase may be encoded by a polynucleotide sequence of SEQ ID NO: 11 or SEQ ID NO: 17, the glucose-6-phosphate dehydrogenase may be encoded by a polynucleotide sequence of SEQ ID NO: 21 or SEQ ID NO: 28, the 6-phosphogluconate dehydrogenase may be encoded by a polynucleotide sequence of SEQ ID NO: 33 or SEQ ID NO: 37, the NAD(P) transhydrogenase may be encoded by a polynucleotide sequence of SEQ ID NO: 40 or SEQ ID NO: 42, the nicotinate phosphoribosyltransferase may be encoded by a polynucleotide sequence of SEQ ID NO: 62, SEQ ID NO: 66, or SEQ ID NO: 70, the NAD$^+$ kinase may be encoded by a polynucleotide sequence of SEQ ID NO: 82 or SEQ ID NO: 86, and the gluconate kinase may be encoded by a polynucleotide sequence of SEQ ID NO: 46, SEQ ID NO: 52, SEQ ID NO: 54, or SEQ ID NO: 60, and the NAD+ diphosphatase may be encoded by a polynucleotide sequence of SEQ ID NO: 74 or SEQ ID NO: 80, but is not limited thereto.

Further, in the polynucleotide, various modifications may be made in the coding region provided that they do not change the amino acid sequence of the protein expressed from the coding region, due to codon degeneracy or in consideration of codons preferred by an organism in which the protein is to be expressed. Therefore, any polynucleotide encoding NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, NAD$^+$ kinase, gluconate kinase, or NAD$^+$ diphosphatase may be included without limitation, as long as it is a polynucleotide sequence encoding the enzyme protein.

Further, a probe which may be produced from a known nucleotide sequence, for example, a sequence which hybridizes with a complementary sequence to all or a part of the polynucleotide sequence under stringent conditions to encode the protein having activity of the enzyme protein of NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, NAD$^+$ kinase, gluconate kinase, or NAD$^+$ diphosphatase may also be included without limitation.

The 'homology' or 'identity' means the degree of relevance between two given amino acid sequences or nucleotide sequences, and may be expressed as a percentage.

The terms 'homology' and 'identity' may be often used interchangeably.

The sequence homology or identity of the conserved polynucleotide or polypeptide may be determined by standard alignment algorithms, and may be used with default gap penalties established by the used program. Substantially, homologous or identical sequences may hybridize under moderately or highly stringent conditions such that the full length of the sequence or at least about 50%, 60%, 70%, 80%, or 90% or more of the full-length may hybridize. Also, contemplated are polynucleotides that contain degenerate codons in place of codons in the hybridization.

Whether or not any two polynucleotide or polypeptide sequences have homology, similarity, or identity may be determined using known computer algorithms such as the "FASTA" program, using, for example, the default parameters as in Pearson et al (1988)[Proc. Natl. Acad. Sci. USA 85]: 2444, or determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277) (version 5.0.0 or later) (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, BLAST of the National Center for Biotechnology Information database, or ClustalW may be used to determine homology, similarity, or identity.

Homology, similarity, or identity of polynucleotides or polypeptides may be determined, for example, by comparing sequence information using a GAP computer program such as Needleman et al. (1970), J Mol Biol. 48: 443, as disclosed in Smith and Waterman, Adv. Appl. Math (1981) 2:482. Briefly, the GAP program defines similarity as the number of aligned symbols (i.e., nucleotides or amino acids), which are similar, divided by the total number of symbols in the shorter of the two sequences. Default parameters for the GAP program may include: (1) a unary comparison matrix (containing a value of 1 for identities and 0 for non-identities) and the weighted comparison matrix of Gribskov et al (1986) Nucl. Acids Res. 14: 6745, as disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or gap open penalty of 10, gap extension penalty of 0.5); and (3) no penalty for end gaps. Therefore, as used herein, the term "homology" or "identity" represents relevance between sequences.

As used herein, the term "enhancement of activity" means that the activity of the enzyme protein is introduced, or the activity is improved, as compared with the endogenous activity possessed by a microorganism or its activity before modification. The "introduction" of the activity means that activity of a specific protein which is not originally possessed by a microorganism is naturally or artificially exhibited. The "non-modified microorganism" refers to a microorganism that has activity of a specific protein originally possessed by the parent strain before transformation, when the trait of the microorganism to be compared is changed by a genetic variation in the specific protein of the microorganism, which is caused by natural or artificial factors. The "endogenous activity" refers to activity of a specific protein originally possessed by the parent strain before transformation, when the trait of the microorganism is changed by a genetic variation caused by natural or artificial factors. In the present disclosure, the non-modification may be used interchangeably with a state having the endogenous activity without genetic variation.

For example, the enhancement of activity may include all of introducing exogenous NADP-dependent glyceraldehyde-3-phosphate dehydrogenase and/or NAD(P) transhydrogenase or enhancing the activity thereof after introduction, and enhancing activity of the endogenous transketolase, glucose-6-phosphate dehydrogenase, 6-phosphogluconate dehydrogenase, nicotinate phosphoribosyltransferase, and/or $NAD^+$ kinase. Specifically, the enhancement of the activity in the present disclosure may be performed by (1) increasing the copy number of the polynucleotide encoding each of the enzymes;

(2) modifying the expression control sequence for increasing expression of the polynucleotide;

(3) modifying the polynucleotide sequence on the chromosome for enhancing the activity of each of the enzymes; and (4) modifying for the enhancement by a combination thereof, but is not limited thereto.

1) The increase of the copy number of the polynucleotide may be, but is not particularly limited to, performed in a form in which the polynucleotide is operably linked to a vector, or by inserting the polynucleotide into the chromosome of a host cell. Further, the increase of the copy number may be carried out by introducing a foreign polynucleotide exhibiting the enzyme activity or a codon-optimized variant polynucleotide of the polynucleotide into a host cell. Any foreign polynucleotide sequence may be used without limitation in the origin or sequence thereof, as long as it exhibits the activity identical/similar to that of the above enzyme. The introduction may be carried out by a known transformation method which is appropriately selected by those skilled in the art, and the enzyme may be produced by expression of the introduced polynucleotide in the host cell, and as a result, its activity may be increased.

Next, 2) the modification of the expression control sequence for increasing the expression of the polynucleotide may be, but is not particularly limited to, performed by inducing a modification on the sequence through deletion, insertion, non-conservative or conservative substitution of the nucleotide sequence, or a combination thereof to further enhance the activity of the expression control sequence, or by replacing the polynucleotide sequence with a nucleotide sequence having a stronger activity. The expression control sequence includes, but is not particularly limited to, a promoter, an operator sequence, a sequence encoding a ribosome-binding site, and a sequence regulating the termination of transcription and translation.

Specifically, a strong exogenous promoter, instead of the original promoter, may be connected to the upstream region of the expression unit of the polynucleotide. Examples of the strong promoter may include CJ7 promoter, lysCP1 promoter, EF-Tu promoter, groEL promoter, aceA or aceB promoter, etc. More specifically, lysCP1 promoter (WO 2009/096689) or CJ7 promoter (WO2006/065095), which is a *Corynebacterium*-derived promoter, may be operably linked to increase the expression rate of the polynucleotide encoding the enzyme, but is not limited thereto.

Furthermore, 3) the modification of the polynucleotide sequence on the chromosome may be, but is not particularly limited to, performed by inducing a modification on the expression control sequence through deletion, insertion, non-conservative or conservative substitution of the polynucleotide sequence, or a combination thereof to further enhance the activity of the polynucleotide sequence, or by replacing the polynucleotide sequence with a polynucleotide sequence which is improved to have a stronger activity.

Lastly, 4) the method of modifying for the enhancement by a combination of 1) to 3) may be performed by applying one or more of the methods of increasing the copy number of the polynucleotide encoding the protein, modifying the expression control sequence for increasing the expression of the polynucleotide, modifying the polynucleotide sequence on the chromosome, and introducing a foreign polynucleotide exhibiting the activity of the protein or a variant polynucleotide in which the codons thereof are codon-optimized.

As used herein, the term "vector" is a DNA construct that includes a nucleotide sequence of a polynucleotide encoding a desired protein operably linked to an appropriate regulatory sequence to enable expression of the desired protein in an appropriate host cell. The regulatory sequence may include a promoter capable of initiating transcription, any operator sequence for the regulation of such transcription, a sequence encoding an appropriate mRNA ribosome-binding domain, and a sequence regulating termination of transcription and translation. After the vector is transformed into the appropriate host cell, it may replicate or function independently of the host genome, and may be integrated into the genome itself.

The vector used in the present disclosure is not particularly limited, as long as it is able to replicate in the host cell, and any vector known in the art may be used. Examples of commonly used vectors may include a natural or recombinant plasmid, cosmid, virus, and bacteriophage. For instance, pWE15, M13, MBL3, MBL4, IXII, ASHII, APII, t10, t11, Charon4A, Charon21A, etc. may be used as a phage vector or cosmid vector. As a plasmid vector, pBR type, pUC type, pBluescriptII type, pGEM type, pTZ type, pCL type, pET type, etc. may be used. Specifically, pDZ, pACYC177, pACYC184, pCL, pECCG117, pUC19, pBR322, pMW118, pCC1BAC vector, etc. may be used, but is not limited thereto.

The vector applicable in the present disclosure is not particularly limited, and a known expression vector may be used. Further, the polynucleotide encoding the desired protein may be inserted into the chromosome using a vector for intracellular chromosomal insertion. The chromosomal insertion of the polynucleotide may be performed by any method known in the art, for example, homologous recombination, but is not limited thereto. A selection marker to confirm the chromosomal insertion may be further included. The selection marker is to select cells transformed with the vector, that is, to confirm insertion of the desired nucleotide molecule, and the selection marker may include markers providing selectable phenotypes, such as drug resistance, auxotrophy, resistance to cytotoxic agents, or expression of surface proteins. Since only cells expressing the selection marker are able to survive or to show different phenotypes under the environment treated with a selective agent, the transformed cells may be selected.

As used herein, the term "transformation" means introduction of a vector including a polynucleotide encoding a target protein into a host cell in such a way that the protein encoded by the polynucleotide is expressed in the host cell. As long as the transformed polynucleotide is expressed in the host cell, it may be integrated into and placed in the chromosome of the host cell, or it may exist extrachromosomally, or irrespective thereof. Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression. Commonly, the expression cassette includes a promoter operably linked to the polynucleotide, transcriptional termination signals, ribosome binding sites, and translation termination signals. The expression cassette may be in the form of a self-replicable expression vector. Also, the polynucleotide as it is may be introduced into the host cell and operably linked to sequences required for expression in the host cell, but is not limited thereto. A method of performing the transformation may include any method of introducing nucleic acids into a cell, and the transformation may be performed by selecting an appropriate standard technique as known in the art depending on the host cell. For example, the method may include electroporation, calcium phosphate ($CaPO_4$) precipitation, calcium chloride ($CaCl_2$)) precipitation, microinjection, a polyethylene glycol (PEG) method, a DEAE-dextran method, a cationic liposome method, and a lithium acetate-DMSO method, etc., but is not limited thereto.

As used herein, the term "operably linked" means a functional linkage between the polynucleotide sequence encoding the desired protein of the present disclosure and a promoter sequence which initiates and mediates transcription of the polynucleotide. The operable linkage may be prepared using a genetic recombinant technology known in the art, and site-specific DNA cleavage and linkage may be prepared using restriction and ligation enzymes in the art, but is not limited thereto.

As used herein, the term "inactivation" refers to attenuation of the activity, no expression of the activity, or no activity even though expressed, as compared with the endogenous activity of the enzyme protein originally possessed by the microorganism or the activity before modification. The inactivation is a concept referring to a case when the activity of an enzyme is attenuated or eliminated, compared with that originally possessed by the microorganism, due to a modification in the enzyme-encoding polynucleotide, a case when the overall intracellular enzymatic activity is attenuated or eliminated, as compared with that of the natural type strain of the microorganism, due to inhibition of expression of the gene encoding the same or inhibition of translation thereof, a case when part or all of the gene is deleted, and a combination thereof, but is not limited thereto.

The inactivation of the enzyme activity may be achieved by applying various methods well known in the art. Examples of the methods may include 1) a method of replacing the gene encoding the enzyme on the chromosome with a mutated gene so that the enzyme activity may be attenuated, including the case when the enzyme activity is eliminated; 2) a method of modifying the expression regulatory sequence of the gene encoding the enzyme on the chromosome; 3) a method of replacing the expression regulatory sequence of the gene encoding the enzyme with a sequence having a weak activity or no activity; 4) a method of deleting part or all of the gene encoding the enzyme on the chromosome; 5) a method of introducing an antisense oligonucleotide (e.g., antisense RNA), which inhibits the translation from the mRNA into an enzyme via a complementary binding to the transcript of the gene on the chromosome; 6) a method of making the attachment of ribosome impossible by forming a secondary structure by artificially adding a sequence complementary to SD sequence on the front end of the SD sequence of the gene encoding the enzyme; 7) a method of RTE (reverse transcription engineering), which adds a promoter so as to be reversely transcribed on the 3' terminus of ORF (open reading frame) of the corresponding sequence, etc., and also include a combination thereof, but are not limited thereto.

The method of modifying the nucleotide sequence on the chromosome may be carried out by inducing a modification on the sequence through deletion, insertion, non-conservative or conservative substitution of a nucleotide sequence or a combination thereof to further attenuate the activity of the enzyme, or may be carried out by replacing the nucleotide sequence with a nucleotide sequence which is improved to have weaker activity or a nucleotide sequence which is improved to have no activity, but is not limited thereto.

The method of modifying the expression regulatory sequence may be carried out by inducing a modification on the expression regulatory sequence through deletion, insertion, non-conservative or conservative substitution of a nucleotide sequence, or a combination thereof to further attenuate the activity of the expression regulatory sequence, or may be carried out by replacing the nucleotide sequence with a nucleotide sequence which has weaker activity. The expression regulatory sequence includes a promoter, an operator sequence, a sequence encoding a ribosome-binding site, and a sequence for regulating the termination of transcription and translation, but is not limited thereto.

Further, the method of deleting part or all of the polynucleotide encoding the enzyme may be performed by replacing the polynucleotide, which encodes the endogenous target protein within the chromosome via a vector for chromosomal insertion in a microorganism, with a polynucleotide or a marker where part of the nucleotide sequence is deleted. Example of the method of deleting part or all of the polynucleotide may include a method of deleting the polynucleotide via homologous recombination, but is not limited thereto.

The polynucleotide may be described as a gene, if it is a collection of polynucleotides that may function. In the present disclosure, the polynucleotide may be used interchangeably with the gene.

As used herein, the term "part", although it may vary depending on the kind of polynucleotide, may specifically refer to 1 nucleotide to 300 nucleotides, more specifically 1 nucleotide to 100 nucleotides, and much more specifically 1 nucleotide to 50 nucleotides, but is not particularly limited thereto.

As used herein, the term "putrescine-producing microorganism" or "microorganism having putrescine productivity" refers to a microorganism naturally having putrescine productivity or a microorganism acquiring putrescine productivity through variation in a parent strain having no putrescine productivity or remarkably low putrescine productivity.

Specifically, the putrescine-producing microorganism in the present disclosure may refer to a natural form of the microorganism itself, or a microorganism acquiring the putrescine-producing ability by insertion of a foreign polynucleotide related to the putrescine production mechanism or by enhancement or inactivation of the activity of an endogenous gene.

More specifically, the putrescine-producing microorganism in the present disclosure may be a "microorganism of the genus *Corynebacterium*". The microorganism of the genus *Corynebacterium* may include specifically *Corynebacterium glutamicum, Corynebacterium ammoniagenes, Brevibacterium lactofermentum, Brevibacterium flavum, Corynebacterium thermoaminogenes, Corynebacterium efficiens*, etc., but is not limited thereto. Much more specifically, the microorganism of the genus *Corynebacterium* in the present disclosure may be *Corynebacterium glutamicum.*

The putrescine-producing microorganism may be, but is not particularly limited to, a microorganism in which activity of ornithine decarboxylase (ODC) is additionally introduced. The ornithine decarboxylase refers to an enzyme that produces putrescine via decarboxylation of ornithine. The microorganism of the genus *Corynebacterium* has no putrescine biosynthesis pathway, but may synthesize putrescine by introduction of foreign ornithine decarboxylase (ODC).

Further, the putrescine-producing microorganism may be, but is not particularly limited to, a microorganism in which ornithine carbamoyltransferase (ArgF) involved in the synthesis of arginine from ornithine and a protein (NCgl1221) involved in glutamate export are inactivated.

Further, the putrescine-producing microorganism may be, but is not particularly limited to, for example, a microorganism in which productivity of ornithine used as a raw material for putrescine biosynthesis is improved by enhancing the activity of acetylglutamate synthase converting glutamate into N-acetylglutamate, ornithine acetyltransferase (ArgJ) converting acetylornithine into ornithine, acetylglutamate kinase (ArgB) converting acetylglutamate into N-acetylglutamyl phosphate, acetyl gamma glutamyl phosphate reductase (ArgC) converting acetylglutamyl phosphate into N-acetylglutamate semialdehyde, acetylornithine aminotransferase (ArgD) converting acetylglutamate semialdehyde into N-acetylornithine, as compared with the endogenous activity thereof, in order to enhance the biosynthesis pathway from glutamate into ornithine.

Further, the putrescine-producing microorganism may be, but is not particularly limited to, a microorganism of the genus *Corynebacterium* having putrescine productivity, in which activity of putrescine acetyltransferase is additionally attenuated.

Moreover, the putrescine-producing microorganism may be, but is not particularly limited to, a microorganism in which activity of putrescine-exporting protein is enhanced, but is not limited thereto. The enhancement of the activity of putrescine-exporting protein may be enhancement of the activity of a protein having an amino acid sequence of SEQ ID NO: 87 in the microorganism of the genus *Corynebacterium* having putrescine productivity, but is not limited thereto.

Further, the enhancement of the activity of putrescine-exporting protein may be inactivation of the activity of a protein having an amino acid sequence of SEQ ID NO: 88 in the microorganism of the genus *Corynebacterium* having putrescine productivity, but is not limited thereto.

Another aspect of the present disclosure provides a method of producing putrescine, the method including the steps of culturing in a medium the putrescine-producing microorganism of the genus *Corynebacterium*, in which NADPH productivity is increased by (1) enhancing activities of one or more from the group consisting of NADP-dependent glyceraldehyde-3-phosphate dehydrogenase, transketolase, glucose-6-phosphate dehydrogenase, 6-phosphogluconate dehydrogenase, NAD(P) transhydrogenase, nicotinate phosphoribosyltransferase, and $NAD^+$ kinase, by (2) inactivating activities of one or more from the group consisting of gluconate kinase and $NAD^+$ diphosphatase, or by (3) a combination of (1) and (2); and collecting putrescine from the microorganism or the medium obtained in step (b).

The "NADP-dependent glyceraldehyde-3-phosphate dehydrogenase", "transketolase", "glucose-6-phosphate 1-dehydrogenase", "6-phosphogluconate dehydrogenase", "NAD(P) transhydrogenase", "nicotinate phosphoribosyltransferase", "NAD kinase", "enhancement of activity", "gluconate kinase" "$NAD^+$ diphosphatase", "inactivation of activity" and "putrescine-producing microorganism of the genus *Corynebacterium*" are the same as described above.

In the method, the step of culturing the microorganism may be, but is not particularly limited to, performed by known batch culture, continuous culture, fed-batch culture, etc. In this regard, the culture conditions are not particularly limited, but an appropriate pH (e.g., a pH of 5 to 9, specifically a pH of 6 to 8, and most specifically a pH of 6.8) may be adjusted using a basic compound (e.g., sodium hydroxide, potassium hydroxide, or ammonia) or an acidic compound (e.g., phosphoric acid or sulfuric acid). Oxygen or an oxygen-containing gas mixture may be introduced into the culture to maintain aerobic conditions. The temperature of the culture may be maintained at 20° C. to 45° C., specifically, 25° C. to 40° C., and may be cultured for about 10 hours to about 160 hours, but are not limited thereto. The putrescine produced by the culture may be secreted into the medium or may remain in the cells.

Additionally, in the culture medium to be used, carbon sources, such as sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid), may be used individually or in a mixture thereof, but are not limited thereto. Nitrogen sources, such as nitrogen-containing organic compounds (e.g., peptone, yeast extract, meat juice, malt extract, corn steep liquor, soybean flour, and urea) or inorganic compounds (e.g., ammonium sulfate, ammonium chloride, ammonium phosphate, ammonium carbonate, and ammonium nitrate), may be used individually or in a mixture thereof, but are not limited thereto. Phosphorous sources, such as potassium dihydrogen phosphate, dipotassium hydrogen phosphate, or sodium-containing salts corresponding thereto, may be used individually or in a mixture thereof, but are not limited thereto. Additionally, other essential growth-stimulating substances including metal salts (e.g., magnesium sulfate or iron sulfate), amino acids, and vitamins may be included in the medium.

With regard to the method of collecting the putrescine which is produced in the culturing step of the present disclosure, the desired amino acid may be collected from the culture medium by an appropriate method known in the art depending on the culture method. For example, centrifugation, filtration, anion exchange chromatography, crystallization, HPLC, etc., may be used, and the desired putrescine may be collected from the cultured medium or microorganism using an appropriate method known in the art. The method of collecting putrescine may further include a purification step.

MODE FOR INVENTION

Hereinafter, the present disclosure will be described in more detail with reference to Examples. However, these Examples are for illustrative purposes only, and the scope of the present disclosure is not intended to be limited by these Examples.

Example 1: Production of Putrescine by Introduction of NADP-Dependent Glyceraldehyde-3-Phosphate Dehydrogenase Production of putrescine was examined by enhancement of NADP-dependent glyceraldehyde-3-phosphate dehydrogenase activity in a putrescine-producing microorganism.

1-1: Preparation of Vector for Introduction of *Lactobacillus delbrueckii* Subsp. *Bulgaricus* ATCC 11842-Derived NADP-Dependent Glyceraldehyde-3-Phosphate Dehydrogenase into Transposon on Chromosome of Coryneform Microorganism

*Lactobacillus delbrueckii* subsp. *Bulgaricus*-derived NADP-dependent glyceraldehyde-3-phosphate dehydrogenase was selected as a NADP-dependent glyceraldehyde-3-phosphate dehydrogenase with high affinity for *Corynebacterium*. Thereafter, to enhance its activity, the following experiment was performed.

An amino acid sequence (SEQ ID NO: 1) and a nucleotide sequence (SEQ ID NO: 2) of *Lactobacillus delbrueckii* subsp. *Bulgaricus* ATCC 11842-derived gapN-encoding Ldb1179 gene were obtained from NIH GenBank.

Further, to introduce Ldb1179 gene into the chromosome using a transposon gene region of a microorganism of the genus *Corynebacterium*, a vector for transformation, pDZTn (WO2009/125992) was used, and cj7 (WO 2006/65095) was used as a promoter. The Ldb1179 gene was amplified as about 1.43 kb of a gene fragment using the chromosome of *Lactobacillus delbrueckii* subsp. *Bulgaricus* ATCC 11842 strain as a template and primers of SEQ ID NOS: 3 and 4 by modifying the start codon TTG with ATG (Table 1). At this time, PCR reaction was performed by repeating 30 cycles of denaturation at 95° C. for 30 seconds, annealing at 55° C. for 30 seconds, and extension at 72° C. for 1 minute and 30 seconds. This PCR product was subjected to electrophoresis in a 0.8% agarose gel, and a band of about 1.4 kb was eluted and purified. Further, PCR of CJ7 promoter region was performed using a pair of primers of SEQ ID NOS: 5 and 6 under the same conditions to obtain a PCR product. At this time, PCR reaction was performed by repeating 30 cycles of denaturation at 95° C. for 30 seconds, annealing at 55° C. for 30 seconds, and extension at 72° C. for 30 seconds. The pDZTn vector was treated with XhoI, and then each of the PCR products obtained above was subjected to fusion cloning. The fusion cloning was performed using an In-Fusion® HD cloning kit (Clontech). The resulting plasmid was designated as pDZTn:P(CJ7)-(L).

TABLE 1

| SEQ ID NO. | Primer | Sequence (5'-3') |
|---|---|---|
| 3 | gapN(L)-F | aaggaaacactgatatcaTGACA GAACACTATTTAAACTATGTCAATG |
| 4 | gapN(L)-R | gccaaaacagcctcgagTTAGTCTT CGATGTTGAAGACAACG |
| 5 | CJ7-F | ggcccactagtctcgagGCCGGCAT AGCCTACCGAT |
| 6 | CJ7-R | GATATCAGTGTTTCCTTTCGTTGG |

1-2: Preparation of Vector for Introduction of *Streptococcus mutans* ATCC 25175-Derived NADP-Dependent Glyceraldehyde-3-Phosphate Dehydrogenase into Transposon Gene on Chromosome of Coryneform Microorganism As a control group of *Lactobacillus delbrueckii* subsp. *Bulgaricus* ATCC 11842-derived gapN, to introduce SMUFR 0590 (Korean Patent No. 1182033) having NADP-dependent glyceraldehyde-3-phosphate dehydrogenase activity into *Streptococcus mutans* ATCC 25175, the following experiment was performed.

An amino acid sequence (SEQ ID NO: 7) and a nucleotide sequence (SEQ ID NO: 8) of *Streptococcus mutans* ATCC 25175-derived gapN-encoding SMUFR 0590 gene were obtained from NIH GenBank, and a vector for introducing SMUFR 0590 expressed by CJ7 promoter into the transposon gene was prepared.

As in Example 1-1, pDZTn was used as a vector for transformation and cj7 was used as a promoter. *Streptococcus mutans* ATCC 25175-derived SMUFR 0590 gene was amplified as a gene fragment of about 1.7 kb using pECCG117-Pcj7-gapN1 (Korean Patent No. 1182033) as a template and primers of SEQ ID NOS: 5 and 9 (Table 2). At this time, PCR reaction was performed by repeating 30 cycles of denaturation at 95° C. for 30 seconds, annealing at 55° C. for 30 seconds, and extension at 72° C. for 2 minutes. This PCR product was subjected to electrophoresis in a 0.8% agarose gel, and a band of a desired size was eluted and purified. The pDZTn vector was treated with XhoI, and then the PCR product obtained above was subjected to fusion cloning. The fusion cloning was performed using an In- Fusion® HD cloning kit (Clontech). The resulting plasmid was designated as pDZTn:P(CJ7)-gapN(S).

TABLE 2

| SEQ ID NO. | Primer | Sequence (5'-3') |
|---|---|---|
| 5 | CJ7-F | ggcccactagtctcgagGCCGGCATAGCCTACCGAT |
| 9 | gapN(S)-R | gccaaaacagcctcgagTTATTTGATATCAAATACGACGGATTTA |

1-3. Fermentation of Putrescine by Introduction of NADP-Dependent Glyceraldehyde-3-Phosphate Dehydrogenase into Putrescine-Producing Coryneform Strain <1-3-1> Introduction of NADP-Dependent Glyceraldehyde-3-Phosphate Dehydrogenase into Transposon Gene on Chromosome of ATCC 13032-Based Putrescine-Producing Microorganism The plasmid pDZTn:P(CJ7)-gapN(L) prepared in Example 1-1 or the plasmid pDZTn:P(CJ7)-gapN(S) prepared in Example 1-2 was introduced into *Corynebacterium glutamicum* KCCM11240P (Korean Patent Publication No. 2013-0003648), KCCM11240P P(CJ7)-NCg12522 (Korean Patent Publication No. 2014-0115244), or KCCM11520P (Korean Patent Publication No. 2014-0049766) by electroporation to obtain each transformant, and each transformant was spread on a BHIS plate medium (37 g/l of Braine heart infusion, 91 g/l of sorbitol, 2% agar) containing kanamycin (25 μg/ml) and X-gal (5-bromo-4-chloro-3-indolyl-β-D-galactoside), and cultured to form colonies. From the colonies thus formed, blue colonies were selected to select a strain introduced with the plasmid pDZTn:P(CJ7)-gapN(L) or pDZTn:P(CJ7)-gapN(S).

The selected strain was seeded in a CM medium (10 g/l of glucose, 10 g/l of polypeptone, 5 g/l of yeast extract, 5 g/l of beef extract, 2.5 g/l of sodium chloride (NaCl), 2 g/l of urea, pH 6.8), and cultured at 30° C. for 8 hours under shaking. Serial dilution from $10^{-4}$ to $10^{-10}$ was performed and then spread on a solid medium containing X-gal, and cultured to form colonies. From the colonies thus formed, white colonies formed at a relatively low ratio were selected to obtain a putrescine-producing *Corynebacterium glutamicum* introduced with Ldb1179 or SMUFR 0590 gene encoding gapN(L) or gapN(S), respectively. The *Corynebacterium glutamicum* variant strains thus prepared were designated as KCCM11240P Tn:P(CJ7)-gapN(L), KCCM11240P Tn:P(CJ7)-gapN(S), KCCM11240P P(CJ7)-NCg12522 Tn:P(CJ7)-gapN(L), KCCM11240P P(CJ7)-NCg12522 Tn:P(CJ7)-gapN(S), KCCM11520P Tn:P(CJ7)-gapN(L), and KCCM11520P Tn:P(CJ7)-gapN(S), respectively.

<1-3-2> Introduction of NADP-Dependent Glyceraldehyde-3-Phosphate Dehydrogenase into Transposon Gene on Chromosome of ATCC 13869-Based Putrescine-Producing Microorganism

*Corynebacterium glutamicum* ATCC13869-based putrescine-producing strains, DAB12-b (Korean Patent Publication No. 2013-0003648), DAB12-b P(CJ7)-NCg12522 (Korean Patent Publication No. 2014-0115244), and DAB12-b ΔNCg12523 (Korean Patent Publication No. 2014-0049766) were transformed with the prepared pDZTn:P(CJ7)-gapN(L) or pDZTn:P(CJ7)-gapN(S) in the same manner as in Example <1-3-1>. *Corynebacterium glutamicum* mutant strains prepared therefrom were designated as DAB12-b Tn:P(CJ7)-gapN(L), DAB12-b Tn:P(CJ7)-gapN(S), DAB12-b P(CJ7)-NCg12522 Tn:P(CJ7)-gapN(L), DAB12-b P(CJ7)-NCg12522 Tn:P(CJ7)-gapN(S), DAB12-b ΔNCg12523 Tn:P(CJ7)-gapN(L), and DAB12-b ΔNCg12523 Tn:P(CJ7)-gapN(S), respectively.

<1-3-3> Evaluation of Putrescine Productivity of NADP-Dependent Glyceraldehyde-3-Phosphate Dehydrogenase Gene-Introduced Coryne Putrescine-Producing Strain In order to examine the production of putrescine by introducing NADP-dependent glyceraldehyde-3-phosphate dehydrogenase gene into the putrescine-producing strain, putrescine productivity was compared between *Corynebacterium glutamicum* mutant strains prepared in Examples <1-3-1> and <1-3-2>.

In detail, 6 kinds of control groups (KCCM11240P, KCCM11240P P(CJ7)-NCg12522, KCCM11520P, DAB12-b, DAB12-b P(CJ7)-NCg12522, and DAB12-b ΔNCg12523) and 12 kinds of *Corynebacterium glutamicum* mutant strains (KCCM11240P Tn:P(CJ7)-gapN(L), KCCM11240P Tn:P(CJ7)-gapN(S), KCCM11240P P(CJ7)-NCg12522 Tn:P(CJ7)-gapN(L), KCCM11240P P(CJ7)-NCg12522 Tn:P(CJ7)-gapN(S), KCCM11520P Tn:P(CJ7)-gapN(L), KCCM11520P Tn:P(CJ7)-gapN(S), DAB12-b Tn:P(CJ7)-gapN(L), DAB12-b Tn:P(CJ7)-gapN(S), DAB12-b P(CJ7)-NCg12522 Tn:P(CJ7)-gapN(L), DAB12-b P(CJ7)-NCg12522 Tn:P(CJ7)-gapN(S), DAB12-b ΔNCg12523 Tn:P(CJ7)-gapN(L), and DAB12-b ΔNCg12523 Tn:P(CJ7)-gapN(S)) were spread on CM plate medium containing 1 mM arginine, respectively and cultured at 30° C. for 24 hours. A platinum loop of each strain thus cultured was inoculated into 25 mL of a production medium, and then sampled at 30° C. and 200 rpm for 50 hours. For total 98 hours, sampling was performed. At the time of culturing all the strains, 1 mM arginine was added to each medium.

<CM Plate Medium (pH 6.8)>

1% glucose, 1% polypeptone, 0.5% yeast extract, 0.5% beef extract, 0.25% sodium chloride (NaCl), 0.2% urea, 100 μl of 50% sodium hydroxide (NaOH), 2% agar, pH 6.8 (based on 1 L of distilled water).

<Production Medium (pH 7.0)>

8% glucose, 0.25% soybean protein, 0.50% corn steep solids, 4% ammonium sulfate ($(NH_4)_2SO_4$), 0.1% potassium phosphate ($KH_2PO_4$), 0.05% magnesium sulfate heptahydrate ($MgSO_4.7H_2O$), 0.15% urea, 100 μg of biotin, 3 mg of thiamine.HCl, 3 mg of calcium-pantothenic acid, 3 mg of nicotinamide, 5% calcium carbonate ($CaCO_3$) (based on 1 L of distilled water).

Concentrations of putrescine produced from the cultures which were sampled for 50 hours were measured, and the results are shown in Table 3 below.

TABLE 3

| Name of strain | Putrescine (g/L) | Productivity (g/l/min) |
|---|---|---|
| KCCM11240P | 5.8 | 6.96 |
| KCCM11240P Tn:P(CJ7)-gapN(L) | 6.4 | 7.68 |
| KCCM11240P Tn:P(CJ7)-gapN(S) | 6.3 | 7.56 |
| KCCM11240P P(CJ7)-NCgl2522 | 7.3 | 8.76 |
| KCCM11240P P(CJ7)-NCgl2522 Tn:P(CJ7)-gapN(L) | 10.6 | 12.72 |
| KCCM11240P P(CJ7)-NCgl2522 Tn:P(CJ7)-gapN(S) | 9.8 | 11.76 |
| KCCM11520P | 7.0 | 8.40 |
| KCCM11520P P(CJ7)-NCgl2522 Tn:P(CJ7)-gapN(L) | 9.8 | 11.76 |
| KCCM11520P P(CJ7)-NCgl2522 Tn:P(CJ7)-gapN(S) | 9.2 | 11.04 |
| DAB12-b | 6.5 | 7.80 |
| DAB12-b Tn:P(CJ7)-gapN(L) | 7.0 | 8.40 |
| DAB12-b Tn:P(CJ7)-gapN(S) | 6.9 | 8.28 |

TABLE 3-continued

| Name of strain | Putrescine (g/L) | Productivity (g/l/min) |
|---|---|---|
| DAB12-b P(CJ7)-NCgl2522 | 7.8 | 9.36 |
| DAB12-b P(CJ7)-NCgl2522 Tn:P(CJ7)-gapN(L) | 11.5 | 13.80 |
| DAB12-b P(CJ7)-NCgl2522 Tn:P(CJ7)-gapN(S) | 10.7 | 12.84 |
| DAB12-b ΔNCgl2523 | 7.5 | 9.00 |
| DAB12-b ΔNCgl2523 Tn:P(CJ7)-gapN(L) | 10.6 | 12.72 |
| DAB12-b ΔNCgl2523 Tn:P(CJ7)-gapN(S) | 10.1 | 12.12 |

As shown in Table 3, all of 12 kinds of *Corynebacterium glutamicum* mutant strains obtained by introducing *L. delbrueckii* subsp. *Bulgaricus* ATCC 11842-derived gapN(L) gene or *Streptococcus mutans* ATCC 25175-derived gapN (S) gene into *Corynebacterium glutamicum* ATCC 13032 or 13869-derived putrescine-producing strain showed increased putrescine productivity, as compared with the control group, indicating that putrescine productivity was increased by providing NADPH through NADP-dependent glyceraldehyde-3-phosphate dehydrogenase.

Further, 6 kinds of *L. delbrueckii* subsp. *Bulgaricus*-derived gapN(L)-introduced mutant strains, KCCM11240P Tn:P(CJ7)-gapN(L), KCCM11240P P(CJ7)-NCg12522 Tn:P(CJ7)-gapN(L), KCCM11520P Tn:P(CJ7)-gapN(L), DAB12-b Tn:P(CJ7)-gapN(L), DAB12-b P(CJ7)-NCg12522 Tn:P(CJ7)-gapN(L), and DAB12-b ΔNCg12523 Tn:P(CJ7)-gapN(L) showed high putrescine productivity, as compared with 6 kinds of *Streptococcus mutans* ATCC 25175-derived gapN(S)-introduced mutant strains, KCCM11240P Tn:P(CJ7)-gapN(S), KCCM11240P P(CJ7)-NCg12522 Tn:P(CJ7)-gapN(S), KCCM11520P Tn:P(CJ7)-gapN(S), DAB12-b Tn:P(CJ7)-gapN(S), DAB12-b P(CJ7)-NCg12522 Tn:P(CJ7)-gapN(S), and DAB12-b ΔNCg12523 Tn:P(CJ7)-gapN(S).

Concentrations of putrescine produced from the cultures which were sampled for 98 hours were measured, and the results are shown in Table 4 below.

TABLE 4

| Name of strain | Putrescine (g/L) | Productivity (g/L/min) |
|---|---|---|
| KCCM11240P | 12.3 | 7.52 |
| KCCM11240P Tn:P(cj7)-gapN(L) | 12.5 | 7.65 |
| KCCM11240P Tn:P(cj7)-gapN(S) | 12.3 | 7.52 |
| KCCM11240P P(CJ7)-NCgl2522 | 15.5 | 9.48 |
| KCCM11240P P(CJ7)-NCgl2522 Tn:P(cj7)-gapN(L) | 16.5 | 10.01 |
| KCCM11240P P(CJ7)-NCgl2522 Tn:P(cj7)-gapN(S) | 16.0 | 9.79 |
| KCCM11520P | 14.5 | 8.87 |
| KCCM11520P P(CJ7)-NCgl2522 Tn:P(cj7)-gapN(L) | 15.3 | 9.36 |
| KCCM11520P P(CJ7)-NCgl2522 Tn:P(cj7)-gapN(S) | 15.0 | 9.18 |
| DAB12-b | 13.1 | 8.02 |
| DAB12-b Tn:P(cj7)-gapN(L) | 13.4 | 8.20 |
| DAB12-b Tn:P(cj7)-gapN(S) | 13.3 | 8.14 |
| DAB12-b P(CJ7)-NCgl2522 | 15.9 | 9.73 |
| DAB12-b P(CJ7)-NCgl2522 Tn:P(cj7)-gapN(L) | 16.7 | 10.22 |
| DAB12-b P(CJ7)-NCgl2522 Tn:P(cj7)-gapN(S) | 16.4 | 10.04 |
| DAB12-b ΔNCgl2523 | 15.0 | 9.18 |
| DAB12-b ΔNCgl2523 Tn:P(cj7)-gapN(L) | 15.7 | 9.61 |
| DAB12-b ΔNCgl2523 Tn:P(cj7)-gapN(S) | 15.5 | 9.49 |

Similarly, in Table 4, KCCM11240P Tn:P(CJ7)-gapN(L), KCCM11240P Tn:P(CJ7)-gapN(S), DAB12-b Tn:P(CJ7)-gapN(L), and DAB12-b Tn:P(CJ7)-gapN(S) which are 4 kinds of KCCM11240P or DAB12-b-based gapN-enhanced mutant strains showed putrescine productivity equivalent to or higher than that of the control group, and KCCM11240P P(CJ7)-NCg12522 Tn:P(CJ7)-gapN(L), KCCM11240P P(CJ7)-NCg12522 Tn:P(CJ7)-gapN(S), KCCM11520P Tn:P(CJ7)-gapN(L), KCCM11520P Tn:P(CJ7)-gapN(S), DAB12-b P(CJ7)-NCg12522 Tn:P(CJ7)-gapN(L), DAB12-b P(CJ7)-NCg12522 Tn:P(CJ7)-gapN(S), DAB12-b ΔNCg12523 Tn:P(CJ7)-gapN(L), DAB12-b ΔNCg12523 Tn:P(CJ7)-gapN(S) which are 8 kinds of KCCM11240P P(CJ7)-NCg12522-, KCCM11520P-, DAB12-b P(CJ7)-NCg12522-, DAB12-b ΔNCg12523-based gapN-enhanced mutant strains having enhanced putrescine export ability showed much increased putrescine productivity.

Accordingly, it was confirmed that when the NADP-dependent glyceraldehyde-3-phosphate dehydrogenase gene was enhanced in *Corynebacterium glutamicum* ATCC 13032 or 13869-derived putrescine-producing strain, productivity and production were all increased, and when the putrescine export ability was enhanced together, the increase was further increased.

1-4: Comparison of NADP-Dependent Glyceraldehyde-3-Phosphate Dehydrogenase Activity in Putrescine Strains NADP-dependent glyceraldehyde-3-phosphate dehydrogenase activity of *L. delbrueckii* subsp. *Bulgaricus*-derived gapN(L) or *Streptococcus mutans*-derived gapN(S) was compared in Ldb1179 gene or SMUFR 0590 gene-introduced KCCM11240P Tn:P(CJ7)-gapN(L) or KCCM11240P Tn:P(CJ7)-gapN(S) strain. As a control group, KCCM11240P strain having no gapN gene was used. Each strain was cultured in a complex plate medium containing 1 mM arginine for about one day, and then cultured in a seed medium containing 1 mM arginine at an initial $OD_{600}$=0.2. The cells were recovered at $OD_{600}$=10.

<Seed Medium>

20 g of glucose, 10 g of peptone, 10 g of yeast extract, 5 g of urea, 4 g of $KH_2PO_4$, 8 g of $K_2HPO_4$, 0.5 g of $MgSO_4$ 7 $H_2O$, 100 µg of biotin, 1000 µg of thiamine-HCl (based on 1 L of process water)

A known method (A. Soukri et al., Protein Expression and Purification; 25; (2002) 519-529) was used to measure NADP-dependent glyceraldehyde-3-phosphate dehydrogenase activity, and the results are shown in Table 5 below.

TABLE 5

| Name of strain | gapN activity (%) |
|---|---|
| KCCM 11240P | 0 |
| KCCM 11240P Tn:P(CJ7)-gapN(L) | 154 |
| KCCM 11240P Tn:P(CJ7)-gapN(S) | 100 |

As shown in Table 5, when the NADP-dependent glyceraldehyde-3-phosphate dehydrogenase activity of *Streptococcus mutans*-derived gapN(S)-introduced KCCM 11240P Tn:P(CJ7)-gapN(S) was regarded as 100, the NADP-dependent glyceraldehyde-3-phosphate dehydrogenase activity of *L. delbrueckii* subsp. *Bulgaricus*-derived gapN(L)-introduced KCCM 11240P Tn:P(CJ7)-gapN(L) strain was 1.5 times higher, indicating that as the NADP-dependent glyceraldehyde-3-phosphate dehydrogenase activity was higher and the amount of NADPH provided was larger, putrescine productivity and production were increased.

Example 2: Putrescine Production Through Transketolase Enhancement

Putrescine production was examined by enhancing transketolase activity in putrescine-producing strains.

2-1: Replacement of Start Codon for Transketolase Enhancement

<2-1-1> Preparation of Vector for Replacing Start Codon TTG of Transketolase with ATG To enhance transketolase activity, a vector for replacing the start codon TTG of the gene encoding the same with ATG was prepared.

An amino acid sequence (SEQ ID NO: 10) and a nucleotide sequence (SEQ ID NO: 11) of *Corynebacterium glutamicum* ATCC 13032-derived transketolase-encoding NCg11512 gene were obtained from NIH GenBank.

In a specific Example of the present disclosure, a vector for transformation, pDZ was used. Two gene fragments of about 0.5 kb were amplified using the chromosome of *Corynebacterium glutamicum* ATCC 13032 strain as a template and primers of SEQ ID NOS: 12 and 13 and primers of SEQ ID NOS: 14 and 15 (Table 6). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. The pDZ vector was treated with XbaI, and then the PCR product obtained above was subjected to fusion cloning. The fusion cloning was performed using an In-Fusion® HD cloning kit (Clontech). The resulting plasmid was designated as pDZ-1'tkt(ATG).

TABLE 6

| SEQ ID NO. | Primer | Sequence (5'-3') |
|---|---|---|
| 12 | NCgl1512_5F | CCGGGGATCCTCTAGAGTAGA CGCTTGATTGGCGGAC |
| 13 | NCgl1512_5R | TCCTTCCTGGGTTAAACCGGG |
| 14 | NCgl1512_ATG_3F | gtttaacccaggaaggaaTGA CCACCTTGACGCTGTCAC |
| 15 | NCgl1512_3R | GCAGGTCGACTCTAGAGTCGAA TAGGCCACGCTCAC |

Further, through PCR reaction and sequencing based on the nucleotide sequence of *Corynebacterium glutamicum* ATCC 13032, an amino acid sequence (SEQ ID NO: 16) and a nucleotide sequence (SEQ ID NO: 17) of the gene having homology to NCg11512 encoding transketolase of *Corynebacterium glutamicum* ATCC 13869 were obtained.

Similarly, two gene fragments of about 0.5 kb were amplified using the chromosome of *Corynebacterium glutamicum* ATCC 13869 strain as a template and the same primers, and a vector was prepared in the same manner as above. The resulting plasmid was designated as pDZ-2'tkt (ATG).

<2-1-2> Replacement of Start Codon of Transketolase in Transposon Gene on Chromosome of ATCC 13032-Based Putrescine-Producing Strain

*Corynebacterium glutamicum* ATCC 13032-based putrescine-producing strain, KCCM11240P P(CJ7)-NCg12522 (Korean Patent Publication No. 2014-0115244) or KCCM11520P (Korean Patent Publication No. 2014-0049766) was transformed with the plasmid pDZ-1'tkt (ATG) prepared in Example 2-1-1 in the same manner as in Example <1-4-1> to prepare a strain in which the start codon of NCg11512 was replaced with ATG respectively. *Corynebacterium glutamicum* mutant strains selected therefrom were designated as KCCM11240P P(CJ7)-NCg12522 tkt (ATG) and KCCM11520P tkt(ATG), respectively.

<2-1-3> Replacement of Start Codon of Transketolase in Transposon Gene on Chromosome of ATCC 13869-Based Putrescine-Producing Strain

*Corynebacterium glutamicum* ATCC13869-based putrescine-producing strain, DAB12-b P(CJ7)-NCg12522 (Korean Patent Publication No. 2014-0115244) or DAB12-b ΔNCg12523 (Korean Patent Publication No. 2014-0049766) was transformed with the plasmid pDZ-2'tkt(ATG) prepared in Example 2-1-1 in the same manner as in Example <1-4-1> to prepare a strain in which the start codon of NCg11512 was replaced with ATG respectively. *Corynebacterium glutamicum* mutant strains selected therefrom were designated as DAB12-b P(CJ7)-NCg12522 tkt(ATG) and DAB12-b ΔNCg12523 tkt(ATG), respectively.

<2-1-4> Evaluation of Putrescine Productivity of Transketolase Start Codon-Replaced Coryne Putrescine-Producing Strain In order to examine the production of putrescine by increasing expression of transketolase-encoding gene tkt in the putrescine-producing strain, putrescine productivity was compared between *Corynebacterium glutamicum* mutant strains prepared in Examples 2-1-2 and 2-1-3 in the same manner as in Example 1-4-3.

TABLE 7

| Name of strain | Putrescine (g/L) | Productivity (g/l/min) |
|---|---|---|
| KCCM11240P P(CJ7)-NCgl2522 | 7.3 | 8.76 |
| KCCM11240P P(CJ7)-NCgl2522 tkt(ATG) | 8.3 | 9.96 |
| KCCM11520P | 7.0 | 8.40 |
| KCCM11520P P(CJ7)-NCgl2522 tkt(ATG) | 7.9 | 9.48 |
| DAB12-b P(CJ7)-NCgl2522 | 7.8 | 9.36 |
| DAB12-b P(CJ7)-NCgl2522 tkt(ATG) | 8.9 | 10.68 |
| DAB12-b ΔNCgl2523 | 7.5 | 9.00 |
| DAB12-b ΔNCgl2523 tkt(ATG) | 8.5 | 10.2 |

As shown in Table 7, in *Corynebacterium glutamicum* ATCC 13032 or 13869-derived putrescine-producing strain, all the mutant strains in which the start codon of tkt was replaced with ATG showed the increased putrescine productivity, as compared with the control group.

2-2: Promoter Replacement for Enhancement of Transketolase and Enhancement of Pentose Phosphate Pathway <2-2-1> Preparation of Transketolase Promoter-Replaced Vector To enhance activity of NCg11512 having transketolase activity, a vector for introducing CJ7 promoter before the start codon of the NCg11512 gene on the chromosome was prepared.

In a specific Example of the present disclosure, a vector for transformation, pDZ was used. Two gene fragments of about 0.5 kb were amplified using the chromosome of *Corynebacterium glutamicum* ATCC 13032 strain as a template and primers of SEQ ID NOS: 12 and 13 and primers of SEQ ID NOS: 19 and 15 (Table 8). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. CJ7 promoter region was obtained using a pair of primers of SEQ ID NOS: 18 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZ-P(CJ7)-1'tkt (ATG).

TABLE 8

| SEQ ID NO. | Primer | Sequence (5'-3') |
|---|---|---|
| 12 | NCgl1512_5F | CCGGGGATCCTCTAGAGTAGACGCTTGATTGGCGGAC |
| 13 | NCgl1512_5R | TCCTTCCTGGGTTAAACCGGG |
| 18 | NCgl1512-PC7-F | gtttaacccaggaaggaGCCGGCATAGCCTACCGAT |
| 6 | PC7-R | GATATCAGTGTTTCCTTTCGTTGG |
| 19 | NCgl1512-PC7-ATG-F | aaggaaacactgatatcaTGACCACCTTGACGCTGTCAC |
| 15 | NCgl1512_3R | GCAGGTCGACTCTAGAGTCGAATAGGCCACGCTCAC |

Similarly, three gene fragments were amplified using the chromosome of *Corynebacterium glutamicum* ATCC 13869 strain as a template and the same primers, and a vector was prepared in the same manner as above. The resulting plasmid was designated as pDZ-P(CJ7)-2'tkt(ATG).

<2-2-2> Replacement of Transketolase Promoter on Chromosome of ATCC 13032-Based Putrescine-Producing Strain

*Corynebacterium glutamicum* ATCC 13032-based putrescine-producing strain, KCCM11240P P(CJ7)-NCg12522 (Korean Patent Publication No. 2014-0115244) or KCCM11520P (Korean Patent Publication No. 2014-0049766) was transformed with the plasmid pDZ-P(CJ7)-1'tkt(ATG) prepared in Example 2-2-1 in the same manner as in Example <1-4-1> to prepare a strain in which CJ7 promoter was introduced before the start codon of NCg11512, respectively. *Corynebacterium glutamicum* mutant strains selected therefrom were designated as KCCM11240P P(CJ7)-NCg12522 P(CJ7)-tkt(ATG) and KCCM11520P P(CJ7)-tkt(ATG), respectively.

<2-2-3> Replacement of Transketolase Promoter on Chromosome of ATCC 13869-Based Putrescine-Producing Strain

*Corynebacterium glutamicum* ATCC13869-based putrescine-producing strain, DAB12-b P(CJ7)-NCg12522 (Korean Patent Publication No. 2014-0115244) or DAB12-b ΔNCg12523 (Korean Patent Publication No. 2014-0049766) was transformed with the plasmid pDZ-P(CJ7)-2'tkt(ATG) prepared in Example 2-2-1 in the same manner as in Example <1-4-1> to prepare a strain in which CJ7 promoter was introduced before the start codon of NCg11512, respectively. *Corynebacterium glutamicum* mutant strains selected therefrom were designated as DAB12-b P(CJ7)-NCg12522 P(CJ7)-tkt(ATG) and DAB12-b ΔNCg12523 P(CJ7)-tkt (ATG), respectively.

<2-2-4> Evaluation of Putrescine Productivity of Transketolase Promoter-Enhanced Coryne Putrescine-Producing Strain In order to examine the production of putrescine by replacing transketolase promoter in the putrescine-producing strain, putrescine productivity was compared between *Corynebacterium glutamicum* mutant strains prepared in Examples 2-2-2 and 2-2-3 in the same manner as in Example 1-4-3.

TABLE 9

| Name of strain | Putrescine (g/L) | Productivity (g/l/min) |
|---|---|---|
| KCCM11240P P(CJ7)-NCgl2522 | 7.3 | 8.76 |
| KCCM11240P P(CJ7)-NCgl2522 P(CJ7)-tkt(ATG) | 12.4 | 14.94 |
| KCCM11520P | 7.0 | 8.4 |
| KCCM11520P P(CJ7)-NCgl2522 P(CJ7)-tkt(ATG) | 11.8 | 14.22 |
| DAB12-b P(CJ7)-NCgl2522 | 7.8 | 9.36 |
| DAB12-b P(CJ7)-NCgl2522 P(CJ7)-tkt(ATG) | 13.4 | 16.08 |
| DAB12-b ΔNCgl2523 | 7.5 | 9.00 |
| DAB12-b ΔNCgl2523 P(CJ7)-tkt(ATG) | 12.5 | 15.06 |

As shown in Table 9, in *Corynebacterium glutamicum* ATCC 13032 or 13869-derived putrescine-producing strain, all the mutant strains in which the tkt promoter was replaced with CJ7 promoter showed the greatly increased putrescine productivity, as compared with the control group.

Example 3: Putrescine Production Through G6PD Enhancement

Putrescine production was examined by enhancing glucose-6-phosphate dehydrogenase activity in putrescine-producing strains.

3-1: Replacement of Promoter for G6PD Enhancement

<3-1-1> Preparation of Vector for Replacing Promoter of G6PD

To enhance G6PD activity, a vector for introducing CJ7 promoter before the start codon of the gene encoding the same on the chromosome was prepared. An amino acid sequence (SEQ ID NO: 20) and a nucleotide sequence (SEQ ID NO: 21) of *Corynebacterium glutamicum* ATCC 13032-derived G6PD-encoding NCg11514 gene were obtained from NIH GenBank.

In a specific Example of the present disclosure, a vector for transformation, pDZ was used. Two gene fragments of about 0.5 kb were amplified using the chromosome of *Corynebacterium glutamicum* ATCC 13032 strain as a template and primers of SEQ ID NOS: 22 and 23 and primers of SEQ ID NOS: 25 and 26 (Table 10). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. CJ7 promoter region was obtained using a pair of primers of SEQ ID NOS: 24 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZ-P(CJ7)-1'zwf.

TABLE 10

| SEQ ID NO. | Primer | Sequence (5'-3') |
|---|---|---|
| 22 | NCgl1514-5F | CCGGGGATCCTCTAGACTGAAGGTGCCAACACTCAGC |
| 23 | NCgl1514-5R | GATGGTAGTGTCACGATCCTTTC |
| 24 | PC7-F(1514) | gatcgtgacactaccatcGCCGGCATAGCCTACCGAT |

TABLE 10-continued

| SEQ ID NO. | Primer | Sequence (5'-3') |
|---|---|---|
| 6 | PC7-R | GATATCAGTGTTTCCTTTCGTTGG |
| 25 | NCgl1514-3F (C7-GTG) | aaggaaacactgatatcGTGAGCACAAACACG ACCCCC |
| 26 | NCgl1514-3R | GCAGGTCGACTCTAGACGGTGGATTCAGCCAT GCC |

Further, through PCR reaction and sequencing based on the nucleotide sequence of *Corynebacterium glutamicum* ATCC 13032, an amino acid sequence (SEQ ID NO: 27) and a nucleotide sequence (SEQ ID NO: 28) of the gene having homology to NCgl1514 encoding G6PD of *Corynebacterium glutamicum* ATCC 13869 were obtained from NIH GenBank.

Similarly, two gene fragments of about 0.5 kb were amplified using the chromosome of *Corynebacterium glutamicum* ATCC 13869 strain as a template and primers of SEQ ID NOS: 22 and 29 and primers of SEQ ID NOS: 25 and 26 (Table 11). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. Further, the CJ7 promoter region was obtained using a pair of primers of SEQ ID NOS: 30 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZ-P(CJ7)-2' zwf.

TABLE 11

| SEQ ID NO. | Primer | Sequence (5'-3') |
|---|---|---|
| 22 | NCgl1514-5F | CCGGGGATCCTCTAGACTGAAGGTGCCAACA CTCAGC |
| 29 | 2'NCgl1514-5R | GATGGTAGCGTCACGATCCTTTC |
| 30 | 2'PC7-F(1514) | GATCGTGACGCTACCATCGCCGGCATAGCCT ACCGAT |
| 6 | PC7-R | GATATCAGTGTTTCCTTTCGTTGG |
| 25 | NCgl1514-3F (C7-GTG) | AAGGAAACACTGATATCGTGAGCACAAACAC GACCCCC |
| 26 | NCgl1514-3R | GCAGGTCGACTCTAGACGGTGGATTCAGCCA TGCC |

<3-1-2> Replacement of Promoter of G6PD on Chromosome of ATCC 13032-Based Putrescine-Producing Strain

*Corynebacterium glutamicum* ATCC 13032-based putrescine-producing strain, KCCM11240P P(CJ7)-NCg12522 (Korean Patent Publication No. 2014-0115244) or KCCM11520P (Korean Patent Publication No. 2014-0049766) was transformed with the plasmid pDZ-P(CJ7)-1'zwf prepared in Example 3-1-1 in the same manner as in Example <1-4-1> to prepare a strain in which the CJ7 promoter was introduced before the start codon of NCg11514, respectively. *Corynebacterium glutamicum* mutant strains selected therefrom were designated as KCCM11240P P(CJ7)-NCg12522 P(CJ7)-zwf and KCCM11520P P(CJ7)-zwf, respectively.

<3-1-3> Replacement of Promoter of G6PD on Chromosome of ATCC 13869-Based Putrescine-Producing Strain

*Corynebacterium glutamicum* ATCC13869-based putrescine-producing strain, DAB12-b P(CJ7)-NCg12522 (Korean Patent Publication No. 2014-0115244) or DAB12-b ΔNCg12523 (Korean Patent Publication No. 2014-0049766) was transformed with the plasmid pDZ-P(CJ7)-2'zwf prepared in Example 3-1-1 in the same manner as in Example <1-4-1> to prepare a strain in which the CJ7 promoter was introduced before the start codon of NCg11512, respectively. *Corynebacterium glutamicum* mutant strains selected therefrom were designated as DAB12-b P(CJ7)-NCg12522 P(CJ7)-zwf and DAB12-b ΔNCg12523 P(CJ7)-zwf, respectively.

<3-1-4> Evaluation of Putrescine Productivity of G6PD Promoter-Enhanced Coryne Putrescine-Producing Strain In order to examine the production of putrescine by replacing the G6PD promoter in the putrescine-producing strain, putrescine productivity was compared between *Corynebacterium glutamicum* mutant strains prepared in Examples 3-1-2 and 3-1-3 in the same manner as in Example 1-4-3.

TABLE 12

| Name of strain | Putrescine (g/L) | Productivity (g/l/h) |
|---|---|---|
| KCCM11240P P(CJ7)-NCgl2522 | 7.3 | 8.76 |
| KCCM11240P P(CJ7)-NCgl2522 P(CJ7)-zwf | 7.9 | 9.48 |
| KCCM11520P | 7.0 | 8.40 |
| KCCM11520P P(CJ7)-NCgl2522 P(CJ7)-zwf | 7.5 | 9.00 |
| DAB12-b P(CJ7)-NCgl2522 | 7.8 | 9.36 |
| DAB12-b P(CJ7)-NCgl2522 P(CJ7)-zwf | 8.5 | 10.20 |
| DAB12-b ΔNCgl2523 | 7.5 | 9.00 |
| DAB12-b ΔNCgl2523 P(CJ7)-zwf | 8.0 | 9.60 |

As shown in Table 12, in *Corynebacterium glutamicum* ATCC 13032 or 13869-derived putrescine-producing strain, all the mutant strains in which the G6PD promoter was replaced with CJ7 promoter showed the increased putrescine productivity, as compared with the control group.

3-2: Co-Replacement of Promoter and Start Codon for G6PD Enhancement

<3-2-1> Preparation of G6PD Promoter and Start Codon-Co-Replaced Vector

To enhance G6PD activity, a vector for introducing CJ7 promoter before the start codon of the gene encoding the same on the chromosome and replacing the start codon GTG with ATG at the same time was prepared.

In a specific Example of the present disclosure, a vector for transformation, pDZ was used. Two gene fragments of about 0.5 kb were amplified using the chromosome of *Corynebacterium glutamicum* ATCC 13032 strain as a template and primers of SEQ ID NOS: 22 and 23 and primers of SEQ ID NOS: 31 and 26 (Table 13). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. CJ7 promoter region was obtained using a pair of primers of SEQ ID NOS: 24 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZ-P(CJ7)-1'zwf (ATG).

TABLE 13

| SEQ ID NO. | Primer | Sequence (5'-3') |
|---|---|---|
| 22 | NCgl1514-5F | CCGGGGATCCTCTAGACTGAAGGTGCCAACACTCAGC |
| 23 | NCgl1514-5R | GATGGTAGTGTCACGATCCTTTC |
| 24 | PC7-F(1514) | gatcgtgacactaccatcGCCGGCATAGCCTACCGAT |
| 6 | PC7-R | GATATCAGTGTTTCCTTTCGTTGG |
| 31 | NCgl1514-3F (C7-ATG) | aaggaaacactgatatcATGAGCACAAACACGACCCCC |
| 26 | NCgl1514-3R | GCAGGTCGACTCTAGACGGTGGATTCAGCCATGCC |

Similarly, two gene fragments of about 0.5 kb were amplified using the chromosome of *Corynebacterium glutamicum* ATCC 13869 strain as a template and primers of SEQ ID NOS: 22 and 29 and primers of SEQ ID NOS: 31 and 26 (Table 14). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. Further, the CJ7 promoter region was obtained using a pair of primers of SEQ ID NOS: 30 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZ-P (CJ7)-2'zwf (ATG).

TABLE 14

| SEQ ID NO. | Primer | Sequence (5'-3') |
|---|---|---|
| 22 | NCgl1514-5F | CCGGGGATCCTCTAGACTGAAGGTGCCAACACTCAGC |
| 29 | 2'NCgl1514-5R | GATGGTAGCGTCACGATCCTTTC |
| 30 | 2'PC7-F(1514) | gatcgtgacgctaccatcGCCGGCATAGCCTACCGAT |
| 6 | PC7-R | GATATCAGTGTTTCCTTTCGTTGG |
| 31 | NCgl1514-3F (C7-ATG) | aaggaaacactgatatcATGAGCACAAACACGACCCCC |
| 26 | NCgl1514-3R | GCAGGTCGACTCTAGACGGTGGATTCAGCCATGCC |

<3-2-2> Replacement of Promoter of G6PD on Chromosome of ATCC 13032-Based Putrescine-Producing Strain

*Corynebacterium glutamicum* ATCC 13032-based putrescine-producing strain, KCCM11240P P(CJ7)-NCg12522 (Korean Patent Publication No. 2014-0115244) or KCCM11520P (Korean Patent Publication No. 2014-0049766) was transformed with the plasmid pDZ-P(CJ7)-1'zwf(ATG) prepared in Example 3-2-1 in the same manner as in Example <1-4-1> to prepare a strain in which the CJ7 promoter was introduced before the start codon of NCg115124 and the start codon was replaced with ATG respectively. *Corynebacterium glutamicum* mutant strains selected therefrom were designated as KCCM11240P P(CJ7)-NCg12522 P(CJ7)-zwf(ATG) and KCCM11520P P(CJ7)-zwf(ATG), respectively.

<3-2-3> Replacement of Promoter of G6PD on Chromosome of ATCC 13869-Based Putrescine-Producing Strain

*Corynebacterium glutamicum* ATCC13869-based putrescine-producing strain, DAB12-b P(CJ7)-NCg12522 (Korean Patent Publication No. 2014-0115244) or DAB12-b ΔNCg12523 (Korean Patent Publication No. 2014-0049766) was transformed with the plasmid pDZ-P(CJ7)-2'zwf(ATG) prepared in Example 3-2-1 in the same manner as in Example <1-4-1> to prepare a strain in which the CJ7 promoter was introduced before the start codon of NCg11512, respectively. *Corynebacterium glutamicum* mutant strains selected therefrom were designated as DAB12-b P(CJ7)-NCg12522 P(CJ7)-zwf(ATG) and DAB12-b ΔNCg12523 P(CJ7)-zwf(ATG), respectively.

<3-2-4> Evaluation of Putrescine Productivity of G6PD Promoter-Enhanced and Start Codon ATG-Replaced Coryne Putrescine-Producing Strain In order to examine the production of putrescine by replacing the G6PD promoter with CJ7 promoter and replacing the start codon with ATG in the putrescine-producing strain, putrescine productivity was compared between *Corynebacterium glutamicum* mutant strains prepared in Examples 3-2-2 and 3-2-3 in the same manner as in Example 1-4-3.

TABLE 15

| Name of strain | Putrescine (g/L) | Productivity (g/l/min) |
|---|---|---|
| KCCM11240P P(CJ7)-NCgl2522 | 7.3 | 8.76 |
| KCCM11240P P(CJ7)-NCgl2522 P(CJ7)-zwf(ATG) | 7.9 | 9.48 |
| KCCM11520P | 7.0 | 8.40 |
| KCCM11520P P(CJ7)-NCgl2522 P(CJ7)-zwf(ATG) | 7.6 | 9.12 |
| DAB12-b P(CJ7)-NCgl2522 | 7.8 | 9.36 |
| DAB12-b P(CJ7)-NCgl2522 P(CJ7)-zwf(ATG) | 8.6 | 10.32 |
| DAB12-b ΔNCgl2523 | 7.5 | 9.00 |
| DAB12-b ΔNCgl2523 P(CJ7)-zwf(ATG) | 8.1 | 9.72 |

As shown in Table 15, in *Corynebacterium glutamicum* ATCC 13032 or 13869-derived putrescine-producing strain, all the mutant strains in which the zwf promoter was replaced with CJ7 promoter and the start codon was replaced with ATG showed the increased putrescine productivity, as compared with the control group.

Example 4: Putrescine Production Through 6PGD Enhancement

The putrescine production was examined by enhancing 6PGD (6-phosphogluconate dehydrogenase) activity in putrescine-producing strains.

4-1: Preparation of Vector for Introducing 6PGD into Transposon Gene on Chromosome of Coryneform Microorganism To enhance activity of NCgl1396 having 6PGD activity, a vector for introducing NCgl1396 expressed by CJ7 promoter into the transposon gene on the chromosome was prepared. An amino acid sequence (SEQ ID NO: 32) and a nucleotide sequence (SEQ ID NO: 33) of NCgl1396 encoding Gnd having *Corynebacterium glutamicum* ATCC 13032-derived 6PGD activity were obtained from NIH GenBank.

In a specific Example of the present disclosure, a vector for transformation, pDZTn was used in order to introduce the gene into the transposon gene on the chromosome using the transposon gene region of the microorganism of the genus *Corynebacterium*. A gene fragment of about 1.45 kb was amplified using the chromosome of *Corynebacterium glutamicum* ATCC 13032 strain as a template and primers of SEQ ID NOS: 34 and 35 (Table 16). At this time, PCR reaction was performed by repeating 30 cycles of denaturation at 95° C. for 30 seconds, annealing at 55° C. for 30 seconds, and extension at 72° C. for 1 minute and 30 seconds. This PCR product was subjected to electrophoresis in a 0.8% agarose gel, and a band of a desired size was eluted and purified. CJ7 promoter region was obtained using a pair of primers of SEQ ID NOS: 5 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZTn:P(CJ7)-1'gnd.

TABLE 16

| SEQ ID NO. | Primer | Sequence (5'-3') |
|---|---|---|
| 34 | NCgl1396-F | aaggaaacactgatatcATGACTAATGGAGATAATCTCGCAC |
| 35 | 1'NCgl1396-R | gccaaaacagcctcgagTTAAGCTTCAACCTCGGAGCG |
| 5 | CJ7-F | ggcccactagtctcgagGCCGGCATAGCCTACCGAT |
| 6 | CJ7-R | GATATCAGTGTTTCCTTTCGTTGG |

Further, through PCR reaction and sequencing based on the nucleotide sequence of *Corynebacterium glutamicum* ATCC 13032, an amino acid sequence (SEQ ID NO: 36) and a nucleotide sequence (SEQ ID NO: 37) of the gene having homology to NCgl1396 encoding Gnd of *Corynebacterium glutamicum* ATCC 13869 were obtained from NIH GenBank.

Similarly, a gene fragment of about 1.45 kb was amplified using the chromosome of *Corynebacterium glutamicum* ATCC 13869 strain as a template and primers of SEQ ID NOS: 34 and 38 (Table 17). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. CJ7 promoter region was obtained using a pair of primers of SEQ ID NOS: 5 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZTn:P(CJ7)-2'gnd.

TABLE 17

| SEQ ID NO. | Primer | Sequence (5'-3') |
|---|---|---|
| 34 | NCgl1396-F | aaggaaacactgatatcATGTCTGGAGGATTAGTTACAGC |
| 38 | 2'NCgl1396-R | gccaaaacagcctcgagTTAAGCTTCCACCTCGGAGC |
| 5 | CJ7-F | ggcccactagtctcgagGCCGGCATAGCCTACCGAT |
| 6 | CJ7-R | GATATCAGTGTTTCCTTTCGTTGG |

4-2: Introduction of 6PGD into Transposon Gene on Chromosome of ATCC 13032-Based Putrescine-Producing Strain

*Corynebacterium glutamicum* ATCC 13032-based putrescine-producing strain, KCCM11240P P(CJ7)-NCgl2522 (Korean Patent Publication No. 2014-0115244) or KCCM11520P (Korean Patent Publication No. 2014-0049766) was transformed with the plasmid pDZTn:P(CJ7)-1'gnd prepared in Example 4-1 in the same manner as in Example <1-4-1> to confirm whether NCgl1396 which is a Gnd-encoding gene was introduced into the transposon. *Corynebacterium glutamicum* mutant strains selected therefrom were designated as KCCM11240P P(CJ7)-NCgl2522 Tn:P(CJ7)-gnd and KCCM11520P Tn:P(CJ7)-gnd, respectively.

4-3: Introduction of 6PGD into Transposon Gene on Chromosome of ATCC 13869-Based Putrescine-Producing Strain

*Corynebacterium glutamicum* ATCC13869-based putrescine-producing strain, DAB12-b P(CJ7)-NCgl2522 (Korean Patent Publication No. 2014-0115244) or DAB12-b ΔNCgl2523 (Korean Patent Publication No. 2014-0049766) was transformed with the plasmid pDZTn:P(CJ7)-1'gnd prepared in Example 4-1 in the same manner as in Example <1-4-1> to confirm whether NCgl1396 which is a Gnd-encoding gene was introduced into the transposon. *Corynebacterium glutamicum* mutant strains selected therefrom were designated as DAB12-b P(CJ7)-NCgl2522 Tn:P(CJ7)-gnd and DAB12-b ΔNCgl2523 Tn:P(CJ7)-gnd, respectively.

4-4: Evaluation of Putrescine Productivity of 6PGD-Enhanced Coryne Putrescine-Producing Strain In order to examine the production of putrescine by introducing the 6PGD-encoding NCgl1396 into the transposon gene on the chromosome in the putrescine-producing strain, putrescine productivity was compared between *Corynebacterium glutamicum* mutant strains prepared in Examples 4-2 and 4-3.

In detail, 4 kinds of control groups (KCCM11240P P(CJ7)-NCgl2522, KCCM11520P, DAB12-b P(CJ7)-NCgl2522, and DAB12-b ΔNCgl2523) and 4 kinds of *Corynebacterium glutamicum* mutant strains (KCCM11240P P(CJ7)-NCgl2522 Tn:P(CJ7)-gnd, KCCM11520P Tn:P(CJ7)-gnd, DAB12-b P(CJ7)-NCgl2522 Tn:P(CJ7)-gnd, and DAB12-b ΔNCgl2523 Tn:P (CJ7)-gnd) were spread on CM plate medium containing 1 mM arginine, respectively and cultured at 30° C. for 24 hours. A platinum loop of each strain thus cultured was inoculated into 25 mL of a production medium, and then cultured under shaking at 30° C. and 200 rpm for 98 hours. At the time of culturing all the strains, 1 mM arginine was added to each medium.

<CM Plate Medium (pH 6.8)>

1% glucose, 1% polypeptone, 0.5% yeast extract, 0.5% beef extract, 0.25% sodium chloride (NaCl), 0.2% urea, 100 μl of 50% sodium hydroxide (NaOH), 2% agar, pH 6.8 (based on 1 L of distilled water)

<Production Medium (pH 7.0)>

8% glucose, 0.25% soybean protein, 0.50% corn steep solids, 4% ammonium sulfate ($(NH_4)_2SO_4$), 0.1% potassium phosphate ($KH_2PO_4$), 0.05% magnesium sulfate heptahydrate ($MgSO_4.7H_2O$), 0.15% urea, 100 μg of biotin, 3 mg of thiamine.HCl, 3 mg of calcium-pantothenic acid, 3 mg of nicotinamide, 5% calcium carbonate ($CaCO_3$) (based on 1 L of distilled water).

Concentrations of putrescine produced from the final products which were cultured for 98 hours were measured, and the results are shown in Table 18 below.

TABLE 18

| Name of strain | Putrescine (g/L) | Productivity (g/L/min) |
|---|---|---|
| KCCM11240P P(CJ7)-NCgl2522 | 15.5 | 9.48 |
| KCCM11240P P(CJ7)-NCgl2522 Tn:P(CJ7)-gnd | 15.9 | 9.73 |
| KCCM11520P | 14.5 | 8.87 |
| KCCM11520P P(CJ7)-NCgl2522 Tn:P(CJ7)-gnd | 15.2 | 9.30 |
| DAB12-b P(CJ7)-NCgl2522 | 15.9 | 9.73 |
| DAB12-b P(CJ7)-NCgl2522 Tn:P(CJ7)-gnd | 16.2 | 9.91 |
| DAB12-b ΔNCgl2523 | 15.0 | 9.18 |
| DAB12-b ΔNCgl2523 Tn:P(CJ7)-gnd | 15.5 | 9.49 |

As shown in Table 18, all of the mutant strains obtained by increasing the expression level of gnd in the *Corynebacterium glutamicum* ATCC 13032 or 13869-derived putrescine-producing strain showed slightly increased putrescine production, as compared with the control group.

Example 5: Putrescine Production Through NAD(P) Transhydrogenase Introduction

Putrescine production according to NADPH supply was examined by enhancing NAD(P) transhydrogenase activity in putrescine-producing *Corynebacterium glutamicum*.

5-1: Preparation of Vector for Introducing *E. coli* W3110-Derived NAD(P) Transhydrogenase into Transposon Gene on Chromosome of Coryneform Microorganism To enhance expression of Y75_p1579 and Y75_p1578 encoding PntAB having *E. coli* W3110-derived NAD(P) transhydrogenase activity, a vector for introducing Y75_p1579 and Y75p1578 gene expressed by CJ7 promoter into the transposon gene on the chromosome was prepared. *E. coli* W3110-derived NAD(P) transhydrogenase forms a complex of PntA and PntB. An amino acid sequence (SEQ ID NO: 39) and a nucleotide sequence (SEQ ID NO: 40) of PntA-encoding Y75p1579 gene and an amino acid sequence (SEQ ID NO: 41) and a nucleotide sequence (SEQ ID NO: 42) of PntB-encoding Y75 p1578 gene were obtained from NIH GenBank.

In a specific Example of the present disclosure, a vector for transformation, pDZTn was used in order to introduce the gene into the transposon gene on the chromosome using the transposon gene region of the microorganism of the genus *Corynebacterium*. A gene fragment of about 2.92 kb was amplified using the chromosome of *E. coli* W3110 strain as a template and primers of SEQ ID NOS: 43 and 44 (Table 19). At this time, PCR reaction was performed by repeating 30 cycles of denaturation at 95° C. for 30 seconds, annealing at 55° C. for 30 seconds, and extension at 72° C. for 3 minutes. This PCR product was subjected to electrophoresis in a 0.8% agarose gel, and a band of a desired size was eluted and purified. CJ7 promoter region was obtained using a pair of primers of SEQ ID NOS: 5 and 6 by repeating 30 cycles of denaturation at 95° C. for 30 seconds, annealing at 55° C. for 30 seconds, and extension at 72° C. for 30 seconds. The pDZTn vector was treated with XhoI, and then the PCR product obtained above was subjected to fusion cloning. The fusion cloning was performed using an In-Fusion® HD cloning kit (Clontech). The resulting plasmid was designated as pDZTn:P(CJ7)-pntAB.

TABLE 19

| SEQ ID NO. | Primer | Sequence (5'-3') |
|---|---|---|
| 43 | Y75_p1579-F | aaggaaacactgatatcATGCGAATTGGCATACCAAGAGAAC |
| 44 | Y75_p1578-RG | gccaaaacagcctcgagTTACAGAGCTTTCAGATTGCATCC |
| 5 | CJ7-F | ggcccactagtctcgagGCCGGCATAGCCTACCGAT |
| 6 | CJ7-R | GATATCAGTGTTTCCTTTCGTTGG |

5-2: Introduction of NAD(P) Transhydrogenase into Transposon Gene on Chromosome of ATCC 13032-Based Putrescine-Producing Strain

*Corynebacterium glutamicum* ATCC 13032-based putrescine-producing strain, KCCM11240P (Korean Patent Publication No. 2013-0003648) or KCCM11240P P(CJ7)-NCg12522 (Korean Patent Publication No. 2014-0115244) was transformed with the plasmid pDZTn:P(CJ7)-pntAB prepared in Example 5-1 in the same manner as in Example <1-4-1> to confirm whether Y75 p1579 and Y75 p1578 which are PntAB-encoding genes were introduced into the transposon. *Corynebacterium glutamicum* mutant strains selected therefrom were designated as KCCM11240P Tn:P(CJ7)-pntAB and KCCM11240P P(CJ7)-NCg12522 Tn:P(CJ7)-pntAB, respectively.

5-3: Introduction of NAD(P) Transhydrogenase into Transposon Gene on Chromosome of ATCC 13869-Based Putrescine-Producing Strain

*Corynebacterium glutamicum* ATCC13869-based putrescine-producing strain, DAB12-b (Korean Patent Publication No. 10-2013-0003648) or DAB12-b P(CJ7)-NCg12522 (Korean Patent Publication No. 2014-0115244) was transformed with the plasmid pDZTn:P(CJ7)-pntAB prepared in Example 5-1 in the same manner as in Example <1-4-1> to confirm whether Y75 p1579 and Y75 p1578 which are PntAB-encoding genes were introduced into the transposon. *Corynebacterium glutamicum* mutant strains selected therefrom were designated as DAB12-b Tn:P(CJ7)-pntAB and DAB12-b P(CJ7)-NCg12522 Tn:P(CJ7)-pntAB, respectively.

5-4: Evaluation of Putrescine Productivity of NAD(P) Transhydrogenase-Introduced Coryne Putrescine-Producing Strain In order to examine the production of putrescine by introducing the NAD(P) transhydrogenase gene in the putrescine-producing strain, putrescine productivity was compared between *Corynebacterium glutamicum* mutant strains prepared in Examples 5-2 and 5-3 in the same manner as in Example 1-4-3.

TABLE 20

| Name of strain | Putrescine (g/L) | Productivity (g/l/min) |
|---|---|---|
| KCCM11240P | 5.8 | 6.96 |
| KCCM11240P Tn:P(CJ7)-pntAB | 6.1 | 7.32 |
| KCCM11240P P(CJ7)-NCgl2522 | 7 | 8.76 |
| KCCM11240P P(CJ7)-NCgl2522 Tn:P(CJ7)-pntAB | 7.5 | 9.00 |
| DAB12-b | 6.5 | 7.80 |
| DAB12-b Tn:P(CJ7)-pntAB | 6.7 | 8.04 |
| DAB12-b P(CJ7)-NCgl2522 | 7.8 | 9.36 |
| DAB12-b P(CJ7)-NCgl2522 Tn:P(CJ7)-pntAB | 8.1 | 9.72 |

As shown in Table 20, in *Corynebacterium glutamicum* ATCC 13032 or 13869-derived putrescine-producing strain, all the mutant strains into which the *E. coli*-derived NADP transhydrogenase pntAB was introduced showed the slightly increased putrescine productivity, as compared with the control group.

Example 6: Putrescine Production Through Inactivation of Gluconate Kinase

Putrescine production was examined by attenuating gluconate kinase activity in the putrescine-producing strain.

Example 6-1: Preparation of Vector for Deletion of Gluconate Kinase Gene NCg12399 or NCg12905

<6-1-1> Preparation of Vector for NCg12399 Deletion

The chromosome of *Corynebacterium glutamicum* ATCC 13032 includes NCg12399 and NCg12905 genes having gluconate kinase activity. Of the two genes having gluconate kinase activity, a vector for NCg12399 gene deletion was prepared. An amino acid sequence (SEQ ID NO: 45) and a nucleotide sequence (SEQ ID NO: 46) of NCg12399 gene of *Corynebacterium glutamicum* ATCC 13032 strain were obtained from NIH GenBank.

In a specific Example of the present disclosure, a vector for transformation, pDZ was used. Two gene fragments of about 0.5 kb were amplified using the chromosome of *Corynebacterium glutamicum* ATCC 13032 strain as a template and primers of SEQ ID NOS: 47 and 48 and primers of SEQ ID NOS: 49 and 50 (Table 21). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. The pDZ vector was treated with XbaI, and then the PCR product obtained above was subjected to fusion cloning. The fusion cloning was performed using an In-Fusion® HD cloning kit (Clontech). The resulting plasmid was designated as pDZ-1'NCg12399(K/O).

TABLE 21

| SEQ ID NO. | Primer | Sequence (5'-3') |
|---|---|---|
| 47 | NCg12399-del-5F | CCGGGGATCCTCTAGAgcccacgctttgtatcaatgg |
| 48 | NCg12399-del-5R | GAAGTTCGTCGCCGTCTTTG |
| 49 | NCg12399-del-3F | GACGGCGACGAACTTCGGCCGCCCAATCTGCAG |
| 50 | NCg12399-del-3R | GCAGGTCGACTCTAGAGGGTGGGGTCTGCTTTGG |

Further, through PCR reaction and sequencing based on the nucleotide sequence of *Corynebacterium glutamicum* ATCC 13032, an amino acid sequence (SEQ ID NO: 51) and a nucleotide sequence (SEQ ID NO: 52) of the gene having homology to NCg12399 of *Corynebacterium glutamicum* ATCC 13869 were obtained from NIH GenBank.

Similarly, two gene fragments of about 0.5 kb were amplified using the chromosome of *Corynebacterium glutamicum* ATCC 13869 strain as a template and the same primers to prepare a vector in the same manner as above. The resulting plasmid was designated as pDZ-2'NCg12399 (K/O).

<6-1-2> Preparation of Vector for NCg12905 Deletion

A vector for deletion of NCg12905 gene which is another gene having gluconate kinase activity was prepared. An amino acid sequence (SEQ ID NO: 53) and a nucleotide sequence (SEQ ID NO: 54) of NCg12905 gene of *Corynebacterium glutamicum* ATCC 13032 strain were obtained from NIH GenBank.

In a specific Example of the present disclosure, a vector for transformation, pDZ was used. Two gene fragments of about 0.5 kb were amplified using the chromosome of *Corynebacterium glutamicum* ATCC 13032 strain as a template and primers of SEQ ID NOS: 55 and 56 and primers of SEQ ID NOS: 57 and 58 (Table 22). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. The pDZ vector was treated with XbaI, and then the PCR product obtained above was subjected to fusion cloning. The fusion cloning was performed using an In-Fusion® HD cloning kit (Clontech). The resulting plasmid was designated as pDZ-1'NCg12905(K/O).

TABLE 22

| SEQ ID NO. | Primer | Sequence (5'-3') |
|---|---|---|
| 55 | NCg12905-del-5F | CCGGGGATCCTCTAGACTGGGTCGTGGCATAAGAA |
| 56 | NCg12905-del-5R | GTGCCTTTGATTGGGCAGC |
| 57 | NCg12905-del-3F | GCCCAATCAAAGGCACGAATTCCTCGCGATGCTTTCC |
| 58 | NCg12905-del-3R | GCAGGTCGACTCTAGACTAGACCAACTTGAGGTAGAGG |

Further, through PCR reaction and sequencing based on the nucleotide sequence of *Corynebacterium glutamicum* ATCC 13032, an amino acid sequence (SEQ ID NO: 59) and a nucleotide sequence (SEQ ID NO: 60) of the gene having homology to NCg12905 of *Corynebacterium glutamicum* ATCC 13869 were obtained from NIH GenBank.

Similarly, two gene fragments of about 0.5 kb were amplified using the chromosome of *Corynebacterium glutamicum* ATCC 13869 strain as a template and the same primers to prepare a vector in the same manner as above. The resulting plasmid was designated as pDZ-2'NCg12905 (K/O).

6-2: Preparation and Evaluation of Strain Having Gluconate Kinase Gene NCg12399 or NCg12905 Deletion <6-2-1> Preparation of NCg12399-Deleted Strain of ATCC 13032-Based Putrescine-Producing Strain

*Corynebacterium glutamicum* ATCC 13032-based putrescine-producing strain, *Corynebacterium glutamicum* KCCM11240P (Korean Patent Publication No. 2013-0003648) was transformed with the plasmid pDZ-1'NCg12399(K/O) prepared in Example 6-1-1 in the same manner as in Example <1-4-1> to prepare a strain in which NCg12399 gene was deleted. *Corynebacterium glutamicum* mutant strain selected therefrom was designated as KCCM11240P ΔNCg12399.

<6-2-2> Preparation of NCg12399 and NCg12905-Co-Deleted Strain of ATCC 13032-Based Putrescine-Producing Strain KCCM11240P ΔNCg12399 prepared in Example 6-2-1 was transformed with the plasmid pDZ-1'NCg12905(K/O) prepared in Example 6-1-2 in the same manner as in Example <1-4-1> to prepare a strain in which both of the NCg12399 gene and the NCg12905 gene were deleted. *Corynebacterium glutamicum* mutant strain selected therefrom was designated as KCCM11240P ΔNCg12399 ΔNCg12905.

<6-2-3> Preparation of NCg12399-Deleted Strain of ATCC 13869-Based Putrescine-Producing Strain

*Corynebacterium glutamicum* ATCC 13032-based putrescine-producing strain, *Corynebacterium glutamicum* DAB12-b (Korean Patent Publication No. 2013-0003648) was transformed with the plasmid pDZ-1'NCg12399(K/O) prepared in Example 6-1-1 in the same manner as in Example <1-4-1> to prepare a strain in which NCg12399 gene was deleted. *Corynebacterium glutamicum* mutant strain selected therefrom was designated as DAB12-b ΔNCg12399.

<6-2-4> Preparation of NCg12399 and NCg12905-Co-Deleted Strain of ATCC 13869-Based Putrescine-Producing Strain KCCM11240P ΔNCg12399 prepared in Example 6-2-3 was transformed with the plasmid pDZ-2'NCg12905(K/O) prepared in Example 6-1-2 in the same manner as in Example <1-4-1> to prepare a strain in which both of the NCg12399 gene and the NCg12905 gene were deleted. *Corynebacterium glutamicum* mutant strain selected therefrom was designated as DAB12-b ΔNCg12399 ΔNCg12905.

<6-2-5> Evaluation of Putrescine Productivity of Gluconate Kinase Activity-Inactivated Strain In order to examine the production of putrescine by deleting gluconate kinase genes NCg12399 and NCg12905 in the putrescine-producing strain, putrescine productivity was compared between *Corynebacterium glutamicum* mutant strains prepared in Examples 6-2-1, 6-2-2, 6-2-3, and 6-2-4 in the same manner as in Example 1-4-3.

TABLE 23

| Name of strain | Putrescine (g/L) | Productivity (g/l/min) |
|---|---|---|
| KCCM11240P | 5.8 | 6.96 |
| KCCM11240P ΔNCgl2399 | 5.9 | 7.08 |
| KCCM11240P ΔNCgl2399 ΔNCgl2905 | 6.4 | 7.68 |
| DAB12-b | 6.5 | 7.80 |
| DAB12-b ΔNCgl2399 | 6.5 | 7.80 |
| DAB12-b ΔNCgl2399 ΔNCgl2905 | 7.1 | 8.52 |

As shown in Table 23, in *Corynebacterium glutamicum* ATCC 13032 or 13869-derived putrescine-producing strain, all the mutant strains in which both of the gluconate kinase genes NCg12399 and NCg12905 were deleted showed the increased putrescine productivity, as compared with the control group. Further, the strains in which both NCg12399 and NCg12905 were deleted showed the higher putrescine productivity than the strain in which NCg12399 alone was deleted.

Example 7: Putrescine Production Through Introduction of NADP-Dependent Glyceraldehyde-3-Phosphate Dehydrogenase and Enhancement of Transketolase Putrescine production was examined by enhancing both NADP-dependent glyceraldehyde-3-phosphate dehydrogenase activity and transketolase activity in the putrescine-producing strain.

7-1: Preparation of Start Codon-Replaced Combination Strain for Transketolase Enhancement in *Streptococcus mutans* ATCC 25175-Derived NADP-Dependent Glyceraldehyde-3-Phosphate Dehydrogenase-Introduced Putrescine-Producing Strain ATCC 13032-based putrescine-producing strain, KCCM11240P P(CJ7)-NCg12522 Tn:P(CJ7)-gapN(S) prepared in Example 1-4-1 was transformed with the plasmid pDZ-1'tkt(ATG) prepared in Example 2-1-1 in the same manner as in Example <1-4-1>. *Corynebacterium glutamicum* mutant strain prepared therefrom was designated as KCCM11240P P(CJ7)-NCg12522 Tn:P(cj7)-gapN(S) tkt (ATG).

Similarly, ATCC 13869-based putrescine-producing strain, DAB-b P(CJ7)-NCg12522 P(CJ7)-gapN(S) prepared in Example 1-4-2 was transformed with the plasmid pDZ-2'tkt(ATG) prepared in Example 2-1-1 in the same manner as in Example <1-4-1>. *Corynebacterium glutamicum* mutant strain prepared therefrom was designated as DAB-b P(CJ7)-NCg12522 Tn:P(cj7)-gapN(S) tkt(ATG).

7-2: Preparation of Promoter-Replaced Combination Strain for Transketolase Enhancement in *Streptococcus mutans* ATCC 25175-Derived NADP-Dependent Glyceraldehyde-3-Phosphate Dehydrogenase-Introduced Putrescine-Producing Strain ATCC 13032-based putrescine-producing strain, KCCM11240P P(CJ7)-NCg12522 Tn:P(CJ7)-gapN(S) prepared in Example 1-4-1 was transformed with the plasmid pDZ-P(CJ7)-1'tkt(ATG) prepared in Example 2-2-1 in the same manner as in Example <1-4-1>. *Corynebacterium glutamicum* mutant strain prepared therefrom was designated as KCCM11240P P(CJ7)-NCg12522 Tn:P(cj7)-gapN (S) P(CJ7)-tkt(ATG).

Similarly, ATCC 13869-based putrescine-producing strain, DAB-b P(CJ7)-NCg12522 P(CJ7)-gapN(S) prepared in Example 1-4-2 was transformed with the plasmid pDZ-P(CJ7)-2'tkt(ATG) prepared in Example 2-2-1 in the same manner as in Example <1-4-1>. *Corynebacterium glutamicum* mutant strain prepared therefrom was designated as DAB-b P(CJ7)-NCg12522 Tn:P(cj7)-gapN(S) P(CJ7)-tkt (ATG).

7-3: Evaluation of Putrescine Productivity of *Streptococcus mutans* ATCC 25175-Derived NADP-Dependent Glyceraldehyde-3-Phosphate Dehydrogenase Activity-Introduced and Transketolase Activity-Enhanced Combination Strain In order to examine putrescine production when the gapN gene having NADP-dependent glyceraldehyde-3-phosphate dehydrogenase activity is enhanced, and at the same time, the start codon TTG of transketolase NCg11512 is replaced with ATG or when the promoter of NCg11512 is replaced with CJ7, *Corynebacterium glutamicum* mutant strains prepared in Examples 7-1 and 7-2 were examined for putrescine productivity.

In detail, two control groups (KCCM11240P P(CJ7)-NCg12522 and DAB12-b P(CJ7)-NCg12522), two mutant strains in which *Streptococcus mutans* ATCC 25175-derived gapN was introduced (KCCM11240P P(CJ7)-NCg12522 Tn:P(CJ7)-gapN(S) and DAB12-b P(CJ7)-NCg12522 Tn:P (CJ7)-gapN(S)), *Corynebacterium glutamicum* mutant strains (KCCM11240P P(CJ7)-NCg12522 Tn:P(cj7)-gapN (S) tkt(ATG) and DAB12-b P(CJ7)-NCg12522 Tn:P(cj7)-gapN(S) tkt(ATG)) of two mutant strains in which *Streptococcus mutans* ATCC 25175-derived gapN was introduced and TTG which is the start codon of tkt was replaced with ATG and *Corynebacterium glutamicum* mutant strains (KCCM11240P P(CJ7)-NCg12522 Tn:P(cj7)-gapN(S) P(CJ7)-tkt(ATG) and DAB12-b P(CJ7)-NCg12522 Tn:P (cj7)-gapN(S) P(CJ7)-tkt(ATG)) of two mutant strains in which *Streptococcus mutans* ATCC 25175-derived gapN was introduced and the promoter of tkt was replaced with CJ7 were compared for putrescine productivity in the same manner as in Example 1-4-3.

TABLE 24

| Name of strain | Putrescine (g/L) | Productivity (g/l/min) |
|---|---|---|
| KCCM11240P P(CJ7)-NCgl2522 | 7 | 8.76 |
| KCCM11240P P(CJ7)-NCgl2522 Tn:P(cj7)-gapN(S) | 9.9 | 11.88 |
| KCCM11240P P(CJ7)-NCgl2522 Tn:P(cj7)-gapN(S) tkt(ATG) | 10.5 | 12.60 |
| KCCM11240P P(CJ7)-NCgl2522 Tn:P(cj7)-gapN(S) P(CJ7)-tkt(ATG) | 12.7 | 15.24 |
| DAB12-b P(CJ7)-NCgl2522 | 7.9 | 9.48 |
| DAB12-b P(CJ7)-NCgl2522 Tn:P(cj7)-gapN(S) | 10.7 | 12.84 |
| DAB12-b P(CJ7)-NCgl2522 Tn:P(cj7)-gapN(S) tkt(ATG) | 11.3 | 13.56 |
| DAB12-b P(CJ7)-NCgl2522 Tn:P(cj7)-gapN(S) P(CJ7)-tkt(ATG) | 13.6 | 16.32 |

As shown in Table 24, when NADP-dependent glyceraldehyde-3-phosphate dehydrogenase gapN was introduced and ATG which is the start codon of tkt was replaced with ATG or gapN was introduced and tkt promoter was replaced to increase the expression level in *Corynebacterium glutamicum* ATCC 13032 or 13869-derived putrescine-producing strain, putrescine productivity was increased, as compared with the strain in which gapN alone was enhanced.

Example 8: Putrescine Production Through Introduction of NADP-Dependent Glyceraldehyde-3-Phosphate Dehydrogenase and Enhancement of G6PD Putrescine production was examined by enhancing both NADP-dependent glyceraldehyde-3-phosphate dehydrogenase activity and G6PD activity in the putrescine-producing strain.

8-1: Preparation of CJ7 Promoter-Introduced Combination Strain for G6PD Enhancement in *Streptococcus mutans* ATCC 25175-Derived NADP-Dependent Glyceraldehyde-3-Phosphate Dehydrogenase-Introduced Putrescine-Producing Strain The ATCC 13032-based putrescine-producing strain, KCCM11240P P(CJ7)-NCg12522 Tn:P(CJ7)-gapN(S) prepared in Example 1-4-1 was transformed with the plasmid pDZ-P(CJ7)-1'zwf prepared in Example 3-1-1 in the same manner as in Example <1-4-1> to prepare a strain in which CJ7 promoter was introduced before the start codon of NCg11514. *Corynebacterium glutamicum* mutant strain selected therefrom was designated as KCCM11240P P(CJ7)-NCg12522 Tn:P(CJ7)-gapN(S) P(CJ7)-zwf.

Similarly, the ATCC 13869-based putrescine-producing strain, DAB-b P(CJ7)-NCg12522 P(CJ7)-gapN(S) prepared in Example 1-4-2 was transformed with the plasmid pDZ-P(CJ7)-2'zwf prepared in Example 3-1-1 in the same manner as in Example <1-4-1> to prepare a strain in which CJ7 promoter was introduced before the start codon of NCg11514. *Corynebacterium glutamicum* mutant strain prepared therefrom was designated as DAB-b P(CJ7)-NCg12522 Tn:P(CJ7)-gapN(S) P(CJ7)-zwf.

8-2: Evaluation of Putrescine Productivity of *Streptococcus mutans* ATCC 25175-Derived NADP-Dependent Glyceraldehyde-3-Phosphate Dehydrogenase Activity-Introduced and G6PD Activity-Enhanced Combination Strain In order to examine putrescine production when the gapN gene having NADP-dependent glyceraldehyde-3-phosphate dehydrogenase activity is enhanced, and at the same time, CJ7 promoter is introduced before the start codon of G6PD NCg11514, the *Corynebacterium glutamicum* mutant strain prepared in Example 8-1 was examined for putrescine productivity.

In detail, two control groups (KCCM11240P P(CJ7)-NCg12522 and DAB12-b P(CJ7)-NCg12522), two mutant strains in which *Streptococcus mutans* ATCC 25175-derived gapN was introduced (KCCM11240P P(CJ7)-NCg12522 Tn:P(CJ7)-gapN(S) and DAB12-b P(CJ7)-NCg12522 Tn:P (CJ7)-gapN(S)), and *Corynebacterium glutamicum* mutant strains ((KCCM11240P P(CJ7)-NCg12522 Tn:P(CJ7)-gapN (S) P(CJ7)-zwf and DAB12-b P(CJ7)-NCg12522 Tn:P (CJ7)-gapN(S) P(CJ7)-zwf) of two mutant strains in which *Streptococcus mutans* ATCC 25175-derived gapN was introduced and CJ7 promoter was introduced before NCg11514 were compared for putrescine productivity in the same manner as in Example 1-4-3.

TABLE 25

| Name of strain | Putrescine (g/L) | Productivity (g/l/min) |
|---|---|---|
| KCCM11240P P(CJ7)-NCgl2522 | 7.3 | 8.76 |
| KCCM11240P P(CJ7)-NCgl2522 Tn:P(CJ7)-gapN(S) | 9.9 | 11.88 |
| KCCM11240P P(CJ7)-NCgl2522 Tn:P(CJ7)-gapN(S) P(CJ7)-zwf | 10.0 | 12.00 |
| DAB12-b P(CJ7)-NCgl2522 | 7.8 | 9.48 |

TABLE 25-continued

| Name of strain | Putrescine (g/L) | Productivity (g/l/min) |
|---|---|---|
| DAB12-b P(CJ7)-NCgl2522 Tn:P(CJ7)-gapN(S) | 10.7 | 12.84 |
| DAB12-b P(CJ7)-NCgl2522 Tn:P(CJ7)-gapN(S) P(CJ7)-zwf | 10.9 | 13.08 |

As shown in Table 25, when NADP-dependent glyceraldehyde-3-phosphate dehydrogenase gapN was introduced and CJ7 promoter was introduced before the start codon of zwf in *Corynebacterium glutamicum* ATCC 13032 or 13869-derived putrescine-producing strain, putrescine productivity was slightly increased, as compared with the strain in which gapN alone was enhanced.

Example 9: Putrescine Production Through Introduction of NADP-Dependent Glyceraldehyde-3-Phosphate Dehydrogenase and Enhancement of Nicotinate Phosphoribosyltransferase In this Example, to activate the reaction of synthesizing NADPH from NADP and to enhance β-nicotinate D-ribonucleotide which is a precursor of NAD and NADP at the same time, the putrescine production was examined by enhancing both NADP-dependent glyceraldehyde-3-phosphate dehydrogenase activity and nicotinate phosphoribosyltransferase activity in the putrescine-producing strain. As the nicotinate phosphoribosyltransferase, *E. coli*-derived gene and *Corynebacterium glutamicum*-derived gene were applied, respectively.

9-1: Preparation of Vector for Introduction of *E. coli* W3110-Derived Nicotinate Phosphoribosyltransferase (EC.2.4.2.11) into Transposon Gene on Chromosome of Coryneform Microorganism A vector for introducing Y75_p0903 encoding pncB having *E. coli* W3110-derived nicotinate phosphoribosyltransferase activity into the transposon gene on the chromosome was prepared. An amino acid sequence (SEQ ID NO: 61) and a nucleotide sequence (SEQ ID NO: 62) of Y75_p0903 gene encoding pncB having *E. coli* W3110-derived nicotinate phosphoribosyltransferase activity were obtained from NIH GenBank.

In a specific Example of the present disclosure, a vector for transformation, pDZTn was used to introduce the gene into the chromosome using the transposon gene region of the microorganism of the genus *Corynebacterium*. A gene fragment of about 1.2 kb of Y75_p0903 gene was amplified using the chromosome of *E. coli* W3110 strain as a template and primers of SEQ ID NOS: 63 and 64 (Table 26). At this time, PCR reaction was performed by repeating 30 cycles of denaturation at 95° C. for 30 seconds, annealing at 55° C. for 30 seconds, and extension at 72° C. for 1 minute and 30 seconds. This PCR product was subjected to electrophoresis in a 0.8% agarose gel, and a band of a desired size was eluted and purified. Further, the CJ7 promoter region was subjected to PCR using a pair of primers of SEQ ID NOS: 5 and 6 under the same conditions to obtain a PCR product. At this time, PCR reaction was performed by repeating 30 cycles of denaturation at 95° C. for 30 seconds, annealing at 55° C. for 30 seconds, and extension at 72° C. for 30 seconds. The pDZTn vector was treated with XhoI, and then the PCR product obtained above was subjected to fusion cloning. The fusion cloning was performed using an In-Fusion® HD cloning kit (Clontech). The resulting plasmid was designated as pDZTn:P(CJ7)-pncB(Eco).

TABLE 26

| SEQ ID NO. | Primer | Sequence (5'-3') |
|---|---|---|
| 63 | pncB(Eco)-F | aaggaaacactgatatcATGACACAATTCGCTTCTCCTG |
| 64 | pncB(Eco)-R | gccaaaacagcctcgagTTAACTGGCTTTTTAATATGCGGAAG |
| 5 | CJ7-F | ggcccactagtctcgagGCCGGCATAGCCTACCGAT |
| 6 | CJ7-R | GATATCAGTGTTTCCTTTCGTTGG |

9-2: Preparation of Vector for Introduction of Nicotinate Phosphoribosyltransferase into Transposon Gene on Chromosome of Coryneform Microorganism A vector for introducing NCg12431 encoding PncB having *Corynebacterium glutamicum* ATCC 13032-derived nicotinate phosphoribosyltransferase activity into the chromosome was prepared. An amino acid sequence (SEQ ID NO: 65) and a nucleotide sequence (SEQ ID NO: 66) of *Corynebacterium glutamicum* ATCC 13032-derived NCg12431 gene were obtained from NIH GenBank. At this time, ATG instead of GTG was introduced as the start codon of NCg12431.

In a specific Example of the present disclosure, a vector for transformation, pDZTn was used to introduce the gene into the chromosome using the transposon gene region of the microorganism of the genus *Corynebacterium*. A gene fragment of about 1.3 kb was amplified using the chromosome of *Corynebacterium glutamicum* ATCC 13032 strain as a template and primers of SEQ ID NOS: 67 and 68 (Table 27). At this time, PCR reaction was performed by repeating 30 cycles of denaturation at 95° C. for 30 seconds, annealing at 55° C. for 30 seconds, and extension at 72° C. for 1 minute and 30 seconds. This PCR product was subjected to electrophoresis in a 0.8% agarose gel, and a band of a desired size was eluted and purified. Further, the CJ7 promoter region was obtained using a pair of primers of SEQ ID NOS: 5 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZTn:P(CJ7)-1'pncB.

TABLE 27

| SEQ ID NO. | Primer | Sequence (5'-3') |
|---|---|---|
| 67 | 1'NCgl2431-F | aaggaaacactgatatcATGAATACCAATCCGTCTGAATTCTCC |
| 68 | 1'NCgl2431-R | gccaaaacagcctcgagCTAAGCGGCCGGCGGGAA |
| 5 | CJ7-F | ggcccactagtctcgagGCCGGCATAGCCTACCGAT |
| 6 | CJ7-R | GATATCAGTGTTTCCTTTCGTTGG |

Further, through PCR reaction and sequencing based on the nucleotide sequence of *Corynebacterium glutamicum* ATCC 13032, an amino acid sequence (SEQ ID NO: 69) and a nucleotide sequence (SEQ ID NO: 70) of the gene having homology to NCg12431 of *Corynebacterium glutamicum* ATCC 13869 were obtained.

Similarly, a gene fragment of about 1.45 kb was amplified using the chromosome of *Corynebacterium glutamicum* ATCC 13869 strain as a template and primers of SEQ ID NOS: 71 and 72 (Table 28). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. Further, the CJ7 promoter region was obtained using a pair of primers of SEQ ID NOS: 5 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZTn:P(CJ7)-2'pncB.

TABLE 28

| SEQ ID NO. | Primer | Sequence (5'-3') |
|---|---|---|
| 71 | 2'NCgl2431-F | aaggaaacactgatatcATGAATACCAATCCTTCTGAATTCTCC |
| 72 | 2'NCgl2431-R | gccaaaacagcctcgagCTAAGCGACCGGCGGGAATC |
| 5 | CJ7-F | ggcccactagtctcgagGCCGGCATAGCCTACCGAT |
| 6 | CJ7-R | GATATCAGTGTTTCCTTTCGTTGG |

9-3: Putrescine Fermentation Through Enhancement of Nicotinate Phosphoribosyltransferase in NADP-Dependent Glyceraldehyde-3-Phosphate Dehydrogenase-Introduced Coryne-Based Putrescine-Producing Strain <9-3-1> Preparation of Nicotinate Phosphoribosyltransferase-Enhanced Strain in *Streptococcus mutans* ATCC 25175-Derived NADP-Dependent Glyceraldehyde-3-Phosphate Dehydrogenase-Introduced Coryne-Based Putrescine-Producing Strain The ATCC 13032-based putrescine-producing strain, KCCM11240P P(CJ7)-NCg12522 Tn:P(CJ7)-gapN(S) prepared in Example 1-4-1 was transformed with the plasmid pDZTn:P(CJ7)-pncB(Eco) prepared in Example 9-1 or the plasmid pDZTn:P(CJ7)-1'pncB prepared in Example 9-2 in the same manner as in <1-4-1> to prepare a strain in which the *E. coli* W3110-derived pncB-encoding Y75 p0903 gene or *Corynebacterium glutamicum* ATCC 13032-derived pncB-encoding NCg12431 gene was introduced into the transposon. The *Corynebacterium glutamicum* mutant strains selected therefrom were designated as KCCM11240P P(CJ7)-NCg12522 Tn:P(CJ7)-gapN(S) Tn:P(CJ7)-pncB (Eco) and KCCM11240P P(CJ7)-NCg12522 Tn:P(CJ7)-gapN(S) Tn:P(CJ7)-1'NCg12431, respectively.

Similarly, the ATCC 13869-based putrescine-producing strain, DAB-b P(CJ7)-NCg12522 P(CJ7)-gapN(S) prepared in Example 1-4-2 was transformed with the plasmid pDZTn:P(CJ7)-pncB(Eco) prepared in Example 9-1 or the plasmid pDZTn:P(CJ7)-2'pncB prepared in Example 9-2 in the same manner as in <1-4-1> to prepare a strain in which the *E. coli* W3110-derived pncB-encoding Y75_p0903 gene or *Corynebacterium glutamicum* ATCC 13869-derived pncB-encoding NCg12431 gene was introduced into the transposon. The *Corynebacterium glutamicum* mutant strains selected therefrom were designated as DAB-b P(CJ7)-NCg12522 Tn:P(CJ7)-gapN(S) Tn:P(CJ7)-pncB (Eco) and DAB-b P(CJ7)-NCg12522 Tn:P(CJ7)-gapN(S) Tn:P(CJ7)-2'NCg12431, respectively.

<9-3-2> Evaluation of Putrescine Productivity of *Streptococcus mutans* ATCC 25175-Derived NADP-Dependent Glyceraldehyde-3-Phosphate Dehydrogenase Activity-Introduced and Nicotinate Phosphoribosyltransferase Activity-Enhanced Combination Strain In order to examine putrescine production when *E. coli* W3110-derived PncB-encoding Y75p0903 gene or *Corynebacterium glutamicum*-derived PncB-encoding NCg12431 gene is enhanced, the *Corynebacterium glutamicum* mutant strain prepared in Example 9-1 was examined for putrescine productivity.

In detail, two control groups (KCCM11240P P(CJ7)-NCg12522 and DAB12-b P(CJ7)-NCg12522), two mutant strains in which *Streptococcus mutans* ATCC 25175-derived gapN was introduced (KCCM11240P P(CJ7)-NCg12522 Tn:P(CJ7)-gapN(S), DAB12-b P(CJ7)-NCg12522 Tn:P (CJ7)-gapN(S)), and *Corynebacterium glutamicum* mutant strains (KCCM11240P P(CJ7)-NCg12522 Tn:P(CJ7)-gapN (S) Tn:P(CJ7)-pncB(Eco), KCCM11240P P(CJ7)-NCg12522 Tn:P(CJ7)-gapN(S) Tn:P(CJ7)-1'NCg12431, DAB12-b P(CJ7)-NCg12522 Tn:P(CJ7)-gapN(S) Tn:P (CJ7)-pncB(Eco), DAB12-b P(CJ7)-NCg12522 Tn:P(CJ7)-gapN(S) Tn:P(CJ7)-2'NCg12431) of 4 kinds of mutant strains in which *Streptococcus mutans* ATCC 25175-derived gapN was introduced, and *E. coli* W3110-derived pncB-encoding Y75p0903 gene or *Corynebacterium glutamicum*-derived pncB-encoding NCg12431 gene was introduced were compared for putrescine productivity in the same manner as in Example 1-4-3.

TABLE 29

| Name of strain | Putrescine (g/L) | Productivity (g/l/min) |
|---|---|---|
| KCCM11240P P(CJ7)-NCgl2522 | 7.3 | 8.76 |
| KCCM11240P P(CJ7)-NCgl2522 Tn:P(CJ7)-gapN(S) | 9.9 | 11.88 |
| KCCM11240P P(CJ7)-NCgl2522 Tn:P(CJ7)-gapN(S) Tn:P(CJ7)-pncB(Eco) | 10.0 | 12.00 |
| KCCM11240P P(CJ7)-NCgl2522 Tn:P(CJ7)-gapN(S) Tn:P(CJ7)-1'NCgl2431 | 10.2 | 12.24 |
| DAB12-b P(CJ7)-NCgl2522 | 7.8 | 9.48 |
| DAB12-b P(CJ7)-NCgl2522 Tn:P(CJ7)-gapN(S) | 10.7 | 12.84 |
| DAB12-b P(CJ7)-NCgl2522 Tn:P(CJ7)-gapN(S) Tn:P(CJ7)-pncB(Eco) | 10.9 | 13.08 |
| DAB12-b P(CJ7)-NCgl2522 Tn:P(CJ7)-gapN(S) Tn:P(CJ7)-2'NCgl2431 | 11.1 | 13.32 |

As shown in Table 29, it was confirmed that when NADP-dependent glyceraldehyde-3-phosphate dehydrogenase gapN was introduced and *E. coli* W3110-derived pncB-encoding Y75_p0903 gene or *Corynebacterium glutamicum*-derived pncB-encoding NCg12431 was enhanced in *Corynebacterium glutamicum* ATCC 13032 or 13869-derived putrescine-producing strain, putrescine productivity was increased. It was also confirmed that putrescine productivity was more increased by the enhancement of Coryne-derived pncB than the introduction of *E. coli*-derived pncB.

Example 10: Putrescine Production Through Introduction of NADP-Dependent Glyceraldehyde-3-Phosphate Dehydrogenase and Deletion of $NAD^+$ Diphosphatase Putrescine production was examined by enhancing both NADP-dependent glyceraldehyde-3-phosphate dehydrogenase activity and $NAD^+$ diphosphatase activity in the putrescine-producing strain.

10-1: Preparation of $NAD^+$ Diphosphatase Gene NCg10744-Deleted Vector

An amino acid sequence (SEQ ID NO: 73) and a nucleotide sequence (SEQ ID NO: 74) of NCg10744 gene having $NAD^+$ diphosphatase activity were obtained from NIH GenBank. To attenuate $NAD^+$ diphosphatase activity, a vector for NCg10744 gene deletion was prepared.

In a specific Example of the present disclosure, a vector for transformation, pDZ was used. Two gene fragments of about 0.5 kb were amplified using the chromosome of *Corynebacterium glutamicum* ATCC 13032 strain as a template and primers of SEQ ID NOS: 75 and 76 and primers of SEQ ID NOS: 77 and 78 (Table 30). At this time, PCR reaction was performed by repeating 30 cycles of denaturation at 95° C. for 30 seconds, annealing at 55° C. for 30 seconds, and extension at 72° C. for 30 seconds. This PCR product was subjected to electrophoresis in a 0.8% agarose gel, and a band of a desired size was eluted and purified. The pDZ vector was treated with XbaI, and then the PCR product obtained above was subjected to fusion cloning. The fusion cloning was performed using an In-Fusion® HD cloning kit (Clontech). The resulting plasmid was designated as pDZ-1'NCg10744(K/O).

TABLE 30

| SEQ ID NO. | Primer | Sequence (5'-3') |
|---|---|---|
| 75 | 0744-del-5F | CCGGGGATCCTCTAGAGCAGATGTGTTGCGTCTAGC |
| 76 | 0744-del-5R | TTGTCATTTACCTCCTCGCTAAATAC |
| 77 | 0744-del-3F | CGAGGAGGTAAATGACAAGGAAGATGAGTTGCCTCAAGG |
| 78 | 0744-del-3R | GCAGGTCGACTCTAGACAGATTACCCGCCACCTGAG |

Further, through PCR reaction and sequencing based on the nucleotide sequence of *Corynebacterium glutamicum* ATCC 13032, an amino acid sequence (SEQ ID NO: 79) and a nucleotide sequence (SEQ ID NO: 80) of the gene having homology to NCg10744 of *Corynebacterium glutamicum* ATCC 13869 were obtained.

Similarly, two gene fragments of about 0.5 kb were amplified using the chromosome of *Corynebacterium glutamicum* ATCC 13869 strain as a template and the same primers to prepare a vector in the same manner as above. The resulting plasmid was designated as pDZ-2'NCg10744 (K/O).

10-2: Preparation and Evaluation of $NAD^+$ Diphosphatase Gene NCg10744-Deleted Strain <10-2-1> Preparation of $NAD^+$ Diphosphatase-Deleted Strain in *Streptococcus mutans* ATCC 25175-Derived NADP-Dependent Glyceraldehyde-3-Phosphate Dehydrogenase-Introduced Coryne-Based Putrescine-Producing Strain The ATCC 13032-based putrescine-producing strain, KCCM11240P P(CJ7)-NCg12522 Tn:P(CJ7)-gapN(S) prepared in Example 1-4-1 was transformed with the plasmid pDZ-1'NCg10744(K/O) prepared in Example 10-1 in the same manner as in <1-4-1> to prepare a strain in which NCg10744 gene was deleted. The *Corynebacterium glutamicum* mutant strains selected therefrom were designated as KCCM11240P P(CJ7)-NCg12522 Tn:P(CJ7)-gapN(S) ΔNCg10744 and KCCM11240P P(CJ7)-NCg12522 Tn:P(CJ7)-gapN(S) ΔNCg10744, respectively.

Similarly, the ATCC 13869-based putrescine-producing strain, DAB-b P(CJ7)-NCg12522 P(CJ7)-gapN(S) prepared in Example 1-4-2 was transformed with the plasmid pDZ-2'NCg10744(K/O) prepared in Example 10-1 in the same manner as in <1-4-1> to prepare a strain in which NCg10744 gene was deleted. The *Corynebacterium glutamicum* mutant strains selected therefrom were designated as DAB-b P(CJ7)-NCg12522 Tn:P(CJ7)-gapN(S) ΔNCg10744, DAB-b P(CJ7)-NCg12522 Tn:P(CJ7)-gapN(S) ΔNCg10744, respectively.

<10-2-2> Evaluation of Putrescine Productivity of *Streptococcus mutans* ATCC 25175-Derived NADP-Dependent Glyceraldehyde-3-Phosphate Dehydrogenase Activity-Introduced and $NAD^+$ Diphosphatase Activity-Inactivated Strain In order to examine putrescine production when $NAD^+$ diphosphatase gene NCg10744 is deleted in the putrescine-producing strain, the *Corynebacterium glutamicum* mutant strain prepared in Example 10-2-1 was examined for putrescine productivity in the same manner as in Example 1-4-3.

TABLE 31

| Name of strain | Putrescine (g/L) | Productivity (g/l/min) |
|---|---|---|
| KCCM11240P P(CJ7)-NCgl2522 | 7.3 | 8.76 |
| KCCM11240P P(CJ7)-NCgl2522 Tn:P(CJ7)-gapN(S) | 9.9 | 11.88 |
| KCCM11240P P(CJ7)-NCgl2522 Tn:P(CJ7)-gapN(S) ΔNCgl0744 | 10.1 | 12.12 |
| DAB12-b P(CJ7)-NCgl2522 | 7.8 | 9.48 |
| DAB12-b P(CJ7)-NCgl2522 Tn:P(CJ7)-gapN(S) | 10.7 | 12.84 |
| DAB12-b P(CJ7)-NCgl2522 Tn:P(CJ7)-gapN(S) ΔNCgl0744 | 11.0 | 13.20 |

As shown in Table 31, it was confirmed that when NADP-dependent glyceraldehyde-3-phosphate dehydrogenase gapN was introduced and $NAD^+$ diphosphatase-encoding NCg10744 was deleted in *Corynebacterium glutamicum* ATCC 13032 or 13869-derived putrescine-producing strain, putrescine productivity was slightly increased.

Example 11: Putrescine Production Through Introduction of NADP-Dependent Glyceraldehyde-3-Phosphate Dehydrogenase and Enhancement of $NAD^+$ Kinase Putrescine production was examined by enhancing both NADP-dependent glyceraldehyde-3-phosphate dehydrogenase activity and $NAD^+$ kinase activity in the putrescine-producing strain.

11-1: Preparation of Vector for Introduction of NAD+ Kinase into Transposon Gene on Chromosome of Coryneform Microorganism To enhance activity of NCg11358 having NAD+ kinase activity, a vector for introducing NCg11358 expressed by CJ7 promoter into the transposon gene on the chromosome was prepared. An amino acid sequence (SEQ ID NO: 81) and a nucleotide sequence (SEQ ID NO: 82) of *Corynebacterium glutamicum* ATCC 13032-derived NCg11358 gene were obtained from NIH GenBank.

In a specific Example of the present disclosure, a vector for transformation, pDZTn was used to introduce the gene into the transposon gene on the chromosome using the transposon gene region of the microorganism of the genus *Corynebacterium*. A gene fragment of about 0.96 kb was amplified using the chromosome of *Corynebacterium glutamicum* ATCC 13032 strain as a template and primers of SEQ ID NOS: 83 and 84 (Table 32). At this time, PCR reaction was performed by repeating 30 cycles of denaturation at 95° C. for 30 seconds, annealing at 55° C. for 30 seconds, and extension at 72° C. for 1 minute. This PCR product was subjected to electrophoresis in a 0.8% agarose gel, and a band of a desired size was eluted and purified. CJ7 promoter region was obtained using a pair of primers of SEQ ID NOS: 5 and 6 by repeating 30 cycles of denaturation at 95° C. for 30 seconds, annealing at 55° C. for 30 seconds, and extension at 72° C. for 30 seconds. The pDZ vector was treated with XbaI, and then the PCR product obtained above was subjected to fusion cloning. The fusion cloning was performed using an In-Fusion® HD cloning kit (Clontech). The resulting plasmid was designated as pDZTn:P(CJ7)-1'ppnk.

TABLE 32

| SEQ ID NO. | Primer | Sequence (5'-3') |
|---|---|---|
| 83 | NCgl1358-F | AAGGAAACACTGATATC_ATGACTGCACCCACG AACGC |
| 84 | NCgl1358-R | GCCAAAACAGCCTCGAG TTACCCCGCTGACCT GGG |
| 5 | CJ7-F | GGCCCACTAGTCTCGAG GCCGGCATAGCCTAC CGAT |
| 6 | CJ7-R | GATATCAGTGTTTCCTTTCGTTGG |

Further, through PCR reaction and sequencing based on the nucleotide sequence of *Corynebacterium glutamicum* ATCC 13032, an amino acid sequence (SEQ ID NO: 85) and a nucleotide sequence (SEQ ID NO: 86) of the gene having homology to ppnK-encoding NCg11358 of *Corynebacterium glutamicum* ATCC 13869 were obtained.

Similarly, a gene fragment of about 0.96 kb was amplified using the chromosome of *Corynebacterium glutamicum* ATCC 13869 strain as a template and the same primers. At this time, PCR reaction and cloning method were the same as above, and the resulting plasmid was designated as pDZTn:P(CJ7)-2'ppnk.

11-2: Putrescine Fermentation Through Enhancement of NAD+ Kinase in NADP-Dependent Glyceraldehyde-3-Phosphate Dehydrogenase-Introduced Coryne-Based Putrescine-Producing Strain <11-2-1> Preparation of NAD Kinase-Enhanced Strain in *Streptococcus mutans* ATCC 25175-Derived NADP-Dependent Glyceraldehyde-3-Phosphate Dehydrogenase-Introduced Coryne-Based Putrescine-Producing Strain The ATCC 13032-based putrescine-producing strain, KCCM11240P P(CJ7)-NCg12522 Tn:P(CJ7)-gapN(S) prepared in Example 1-4-1 was transformed with the plasmid pDZTn:P(CJ7)-1'ppnk prepared in Example 11-1 in the same manner as in <1-4-1> to prepare a strain in which NCg11358 gene was introduced into the transposon. The *Corynebacterium glutamicum* mutant strain selected therefrom was designated as KCCM11240P P(CJ7)-NCg12522 Tn:P(CJ7)-gapN(S) Tn:P(CJ7)-1'ppnk.

Similarly, the ATCC 13869-based putrescine-producing strain, DAB-b P(CJ7)-NCg12522 P(CJ7)-gapN(S) prepared in Example 1-4-2 was transformed with the plasmid pDZTn:P(CJ7)-2'ppnk prepared in Example 11-1 in the same manner as in <1-4-1> to prepare a strain in which NCg11358 gene was introduced into the transposon. The *Corynebacterium glutamicum* mutant strain selected therefrom was designated as DAB-b P(CJ7)-NCg12522 Tn:P(CJ7)-gapN (S) Tn:P(CJ7)-2'ppnK.

<11-2-2> Evaluation of Putrescine Productivity of *Streptococcus mutans* ATCC 25175-Derived NADP-Dependent Glyceraldehyde-3-Phosphate Dehydrogenase Activity-Introduced and NAD+ Kinase Activity-Enhanced Strain In order to examine putrescine production when NCg11358 having NAD+ kinase activity was introduced in the form of being expressed by CJ7 promoter into the transposon gene on the chromosome in order to facilitate supply of NADP as a precursor of *Corynebacterium glutamicum* NADPH, the *Corynebacterium glutamicum* mutant strain prepared in Example 11-2-1 was examined for putrescine productivity.

In detail, two control groups (KCCM11240P P(CJ7)-NCg12522 and DAB12-b P(CJ7)-NCg12522), two mutant strains in which *Streptococcus mutans* ATCC 25175-derived gapN was introduced (KCCM11240P P(CJ7)-NCg12522 Tn:P(CJ7)-gapN(S), DAB12-b P(CJ7)-NCg12522 Tn:P (CJ7)-gapN(S)), and *Corynebacterium glutamicum* mutant strains (KCCM11240P P(CJ7)-NCg12522 Tn:P(CJ7)-gapN (S) Tn:P(CJ7)-1'ppnK and DAB12-b P(CJ7)-NCg12522 Tn:P(CJ7)-gapN(S) Tn:P(CJ7)-2'ppnK) of 4 kinds of mutant strains in which *Streptococcus mutans* ATCC 25175-derived gapN was introduced and *Corynebacterium glutamicum*-derived ppnK was introduced were compared for putrescine productivity from the final products which were cultured for 98 hours in the same manner as in Example 1-4-3.

TABLE 33

| Name of strain | Putrescine (g/L) | Productivity (g/L/min) |
|---|---|---|
| KCCM11240P P(CJ7)-NCgl2522 | 15.5 | 9.48 |
| KCCM11240P P(CJ7)-NCgl2522 Tn:P(CJ7)-gapN(S) | 16.1 | 9.85 |
| KCCM11240P P(CJ7)-NCgl2522 Tn:P(CJ7)-gapN(S) Tn:P(CJ7)-1'ppnK | 16.7 | 10.22 |
| DAB12-b P(CJ7)-NCgl2522 | 15.9 | 9.73 |
| DAB12-b P(CJ7)-NCgl2522 Tn:P(CJ7)-gapN(S) | 16.5 | 10.01 |
| DAB12-b P(CJ7)-NCgl2522 Tn:P(CJ7)-gapN(S) Tn:P(CJ7)-2'ppnK | 16.9 | 10.34 |

As shown in Table 33, it was confirmed that when NADP-dependent glyceraldehyde-3-phosphate dehydrogenase gapN was introduced and NCg11358 encoding *Corynebacterium glutamicum*-derived NAD+ kinase ppnK was enhanced in *Corynebacterium glutamicum* ATCC 13032 or 13869-derived putrescine-producing strain, putrescine productivity was slightly increased.

In the present disclosure, it was confirmed that the *Corynebacterium glutamicum* strain, in which Ldb1179 was introduced into the transposon of the putrescine-producing microorganism of the genus *Corynebacterium* having deletion of the acetyl putrescine synthetic pathway to enhance NADP-dependent glyceraldehyde-3-phosphate dehydrogenase activity, is able to produce putrescine with high yield and high productivity, and the strain was designated as KCCM11240P Tn:P(CJ7)-gapN(L), CC01-0811, and then deposited at the Korean Culture Center of Microorganisms (KCCM) which is the international depository authority under the Budapest Treaty on Jun. 29, 2017 with the Accession No. KCCM12052P.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

[Deposit Number]

Deposit authority: Korean Culture Center of Microorganisms (overseas)

Accession Number: KCCM12052P

Date of deposit: 2017 Jun. 29.

The invention claimed is:

1. A putrescine-producing microorganism of the genus *Corynebacterium*, wherein NADPH (reduced nicotinamide adenine dinucleotide phosphate) productivity is increased, as compared with a non-modified microorganism, by enhancing an activity of NADP-dependent glyceraldehyde-3-phosphate dehydrogenase.

2. The putrescine-producing microorganism of the genus *Corynebacterium* of claim 1, wherein the microorganism has (1) further enhancement of activities of one or more from the group consisting of transketolase, glucose-6-phosphate dehydrogenase, 6-phosphogluconate dehydrogenase, NAD(P) transhydrogenase, nicotinate phosphoribosyltransferase, and NAD+ kinase, (2) further inactivation of activities of one or more from the group consisting of gluconate kinase and NAD+ diphosphatase, or (3) a further combination of (1) and (2), thereby showing increased NADPH productivity, as compared with a non-modified microorganism.

3. The putrescine-producing microorganism of the genus *Corynebacterium* of claim 1, wherein activity of ornithine decarboxylase is further introduced.

4. The putrescine-producing microorganism of the genus *Corynebacterium* of claim 1, wherein activity of putrescine acetyltransferase is further attenuated.

5. The putrescine-producing microorganism of the genus *Corynebacterium* of claim 1, wherein activity of putrescine export protein is further enhanced.

6. The putrescine-producing microorganism of the genus *Corynebacterium* of claim 1, wherein the microorganism is *Corynebacterium glutamicum*.

7. A method of producing putrescine, the method comprising the steps of:

(i) culturing the putrescine-producing microorganism of claim 1 in a medium; and (ii) collecting putrescine from the cultured microorganism or medium.

8. A method of producing putrescine, the method comprising the steps of:

(i) culturing the putrescine-producing microorganism of claim 2 in a medium; and (ii) collecting putrescine from the cultured microorganism or medium.

9. A method of producing putrescine, the method comprising the steps of:

(i) culturing the putrescine-producing microorganism of claim 3 in a medium; and (ii) collecting putrescine from the cultured microorganism or medium.

10. A method of producing putrescine, the method comprising the steps of:

(i) culturing the putrescine-producing microorganism of claim 4 in a medium; and (ii) collecting putrescine from the cultured microorganism or medium.

11. A method of producing putrescine, the method comprising the steps of:

(i) culturing the putrescine-producing microorganism of claim 5 in a medium; and (ii) collecting putrescine from the cultured microorganism or medium.

12. A method of producing putrescine, the method comprising the steps of:

(i) culturing the putrescine-producing microorganism of claim 6 in a medium; and (ii) collecting putrescine from the cultured microorganism or medium.

* * * * *